(12) United States Patent
Kim et al.

(10) Patent No.: US 9,601,699 B2
(45) Date of Patent: Mar. 21, 2017

(54) CHRYSENE-BASED COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Kwang-Hyun Kim, Yongin (KR); Young-Kook Kim, Yongin (KR); Eun-Young Lee, Yongin (KR)

(73) Assignee: SAMSUNG DISPLAY CO., LTD., Yongin, Gyeonggi-Do (KR)

(*) Notice: Subject to any disclaimer, the term of this patent is extended or adjusted under 35 U.S.C. 154(b) by 373 days.

(21) Appl. No.: 14/255,225

(22) Filed: Apr. 17, 2014

(65) Prior Publication Data
US 2015/0115232 A1  Apr. 30, 2015

(30) Foreign Application Priority Data
Oct. 31, 2013  (KR) .......................... 10-2013-0131518

(51) Int. Cl.
*H01L 51/00* (2006.01)
*C07D 401/14* (2006.01)
(Continued)

(52) U.S. Cl.
CPC ........ *H01L 51/0054* (2013.01); *C07D 209/56* (2013.01); *C07D 401/04* (2013.01);
(Continued)

(58) Field of Classification Search
None
See application file for complete search history.

(56) References Cited

U.S. PATENT DOCUMENTS 5,645,948 A  7/1997 Shi et al.
6,465,115 B2  10/2002 Shi et al.
(Continued)

FOREIGN PATENT DOCUMENTS

JP  10-017860 A  1/1998
JP  11-087067 A  3/1999
(Continued)

OTHER PUBLICATIONS

"A Novel Conjugated Polymer Based on 4H-benzo[def]carbazole backbone for OLED", 2009 Fall Assembly and Symposium, vol. 34, No. 2, 2009, Oct. 8-9, 2009.
(Continued)

*Primary Examiner* — J. L. Yang
(74) *Attorney, Agent, or Firm* — Lee & Morse, P.C.

(57) ABSTRACT

A chrysene-based compound and an organic light-emitting device including the same, the chrysene-based compound being represented by Formula 1, below:

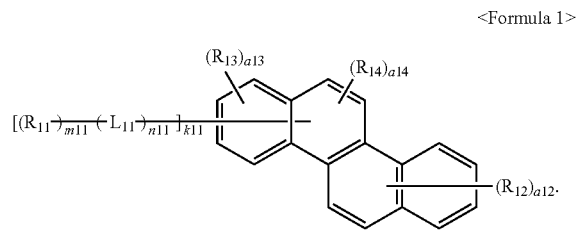

20 Claims, 1 Drawing Sheet

(51) Int. Cl.
- *C07D 401/04* (2006.01)
- *C07D 401/10* (2006.01)
- *C07D 403/10* (2006.01)
- *C07D 209/56* (2006.01)
- *H01L 51/50* (2006.01)

(52) U.S. Cl.
CPC ......... *C07D 401/10* (2013.01); *C07D 401/14* (2013.01); *C07D 403/10* (2013.01); *H01L 51/0052* (2013.01); *H01L 51/0058* (2013.01); *H01L 51/0067* (2013.01); *H01L 51/0072* (2013.01); *H01L 51/006* (2013.01); *H01L 51/0059* (2013.01); *H01L 51/0081* (2013.01); *H01L 51/5072* (2013.01)

(56) References Cited

U.S. PATENT DOCUMENTS

| | | | |
|---|---|---|---|
| 6,596,415 | B2 | 7/2003 | Shi et al. |
| 2003/0165715 | A1 | 9/2003 | Yoon et al. |
| 2012/0256172 | A1 | 10/2012 | Ito et al. |
| 2015/0014656 | A1* | 1/2015 | Lim ................. C07B 59/002 257/40 |

FOREIGN PATENT DOCUMENTS

| | | |
|---|---|---|
| JP | 2010-195708 A | 9/2010 |
| KR | 10-0691543 B1 | 3/2007 |
| KR | 10-2012-0051598 A | 5/2012 |
| KR | 2012-0104087 A | 9/2012 |

OTHER PUBLICATIONS

Shigehiro Yamaguchi, et al., "Diphenylamino-Substituted 2,5-Diarylsiloles for Single-Layer Organic Electroluminescent Devices", Chemistry Letters 2001, The Chemical Society of Japan, pp. 98-99.

Advanced Materials 10, 1998, p. 1136.

Y.T. Tao, et al., Sharp green electroluminescence from 1H-pyrazolo[3,4-b]quinolone-based light-emitting diodes, Appl. Phys.Lett, vol. 77, No. 11, pp. 2000,1575-1577.

Chihaya Adachi, et al., "Confinement of charge carriers and molecular excitons within 5nmthick emitter layer of organic electroluminescent devices with a double heterostructure", Appl.Phys.Lett. 57, No. 6, 2000, pp. 531-533.

C.W. Tang, et al., Organic electroluminescent diodes, Appl.Phys. Lett, 51, 1987, pp. 913-915.

Youichi Sakamoto, et al., "Synthesis, Characterization, and Electron-Transport Property of Perflourinated Phenylene Dendrimers", J. Am. Chem. Soc. 2000, pp. 1832-1833.

* cited by examiner

10

| 190 |
|-----|
| 150 |
| 110 |

CHRYSENE-BASED COMPOUND AND ORGANIC LIGHT-EMITTING DEVICE INCLUDING THE SAME

CROSS-REFERENCE TO RELATED APPLICATION

Korean Patent Application No. 10-2013-0131518, filed on Oct. 31, 2013, in the Korean Intellectual Property Office, and entitled: "Chrysene-Based Compounds And Organic Light-Emitting Devices Comprising The Same," is incorporated by reference herein in its entirety.

BACKGROUND

1. Field

Embodiments relate to a chrysene-based compound and an organic light-emitting device including the same.

2. Description of the Related Art

Organic light-emitting devices (OLEDs), which are self-emitting devices, may have advantages such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially disposed in this order on a substrate. Holes injected from the first electrode move to the emission layer via the hole transport region, while electrons injected from the second electrode move to the emission layer via the electron transport region. Carriers such as the holes and electrons recombine in the emission layer to generate exitons. When the exitons drop from an excited state to a ground state, light is emitted.

SUMMARY

Embodiments are directed to a chrysene-based compound and an organic light-emitting device including the same.

One or more embodiments include a chrysene-based compound, and an organic light-emitting device including the same.

Additional aspects will be set forth in part in the description which follows and, in part, will be apparent from the description, or may be learned by practice of the presented embodiments.

According to one or more embodiments, there is provided chrysene-based compound represented by Formula 1:

<Formula 1>

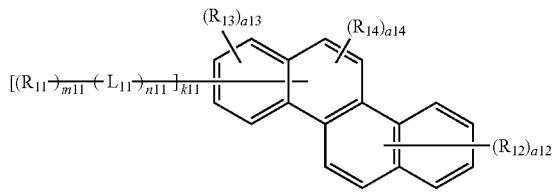

wherein, in Formula 1, $L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_6$arylene group, a substituted or unsubstituted $C_1$-$C_{60}$ heteroarylene group, and a substituted or unsubstituted non-aromatic condensed, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$arylene group, the substituted $C_1$-$C_{60}$ heteroarylene group, and the substituted non-aromatic condensed polycyclic group is selected from a deuterium atom, a halogen atom, a hydroxyl group, a cyano group, a nitro group, an amino group, an amidino group a hydrazine group, a hydrazone group, a carboxylic acid group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, n11 is an integer selected from 0 to 3, $R_{11}$ is a group represented by one of Formulae 2-1 and 2-2, k11 is an integer selected from 1 to 4, $R_{12}$ to $R_{14}$ are each independently selected from a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, a12 is an integer selected from 1 to 5, a13 and a14 are each independently an integer selected from 0 to 3,

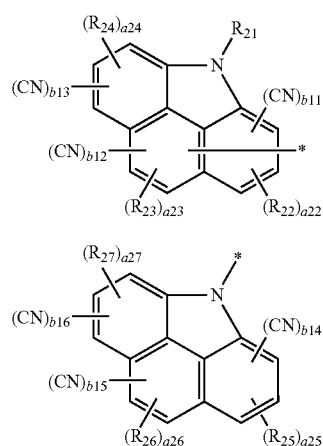

<Formula 2-1>

<Formula 2-2> wherein, in Formulae 2-1 and 2-2, $R_{21}$ to $R_{27}$ are each independently selected from a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, a22 to a27 are each independently an integer selected from 0 to 3, b11 to b16 are each independently selected from an integer from 0 to 2, wherein a sum of b11, b12, and b13 is 1 or greater, and a sum of b14, b15, and b16 is 1 or greater, and

* is a binding site to $L_{11}$ or a chrysene in Formula 1.

According to one or more embodiments, an organic light-emitting device includes: a first electrode; a second electrode disposed opposite to the first electrode; and an organic layer disposed between the first electrode and the second electrode and including an organic layer, wherein the organic layer includes any of the chrysene-based compounds of Formula 1 above.

BRIEF DESCRIPTION OF THE DRAWING

Features will be apparent to those of skill in the art by describing in detail exemplary embodiments with reference to the attached drawing in which:

FIG. 1 illustrates a schematic cross-sectional view of a structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an embodiment, there is provided a chrysene-based compound represented by Formula 1 below:

<Formula 1>

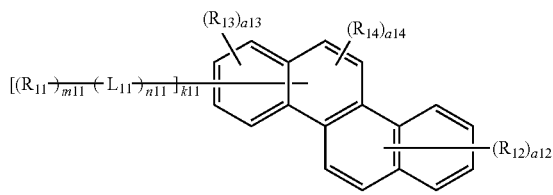

In Formula 1, $L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, and a substituted or unsubstituted non-aromatic condensed polycyclic group, and at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, and the substituted non-aromatic condensed polycyclic group is selected from a deuterium atom, a halogen atom, a hydroxyl group, a cyano group, a nitro group, an amino group, an amidino group a hydrazine group, a hydrazone group, a carboxylic acid group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$-aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group.

In some embodiments, $L_{11}$ in Formula 1 may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronerylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenyenel group, a perylenylene group, a pentaphenylene group, a hexacenylene group, a pentacenylene group, a rubicenylene group, a coronerylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolyene group, and a dibenzosilolylene group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thienyl group, a furanyl group, a silolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothienyl group, a benzosilolyl group, an isobenzothiazolyl group, a benzooxazolyl group, an isobenzooxazolyl group, a triazolyl group, a tetrazol group, an oxadiazolyl group, a triazinyl group, a dibenzofuranyl group, a dibenzothienyl group, a benzocarbazolyl group, a dibenzocarbazolyl group, and a dibenzosilolyl group, but is not limited thereto.

In some other embodiments, $L_{11}$ in Formula 1 may be a group represented by one of Formulae 3-1 to 3-32, but is not limited thereto:

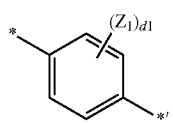

3-1

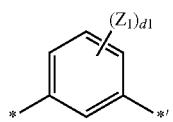

3-2

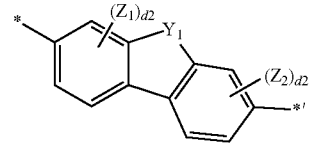

3-3

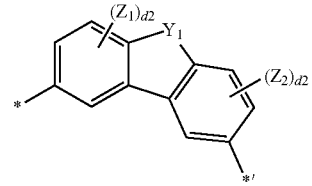

3-4

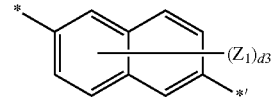

3-5

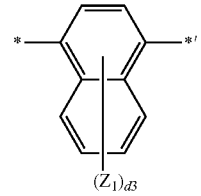

3-6

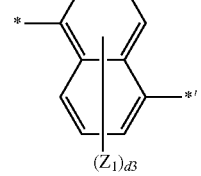

3-7

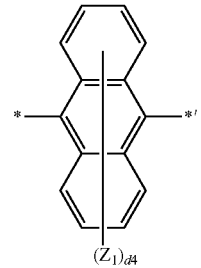

3-8

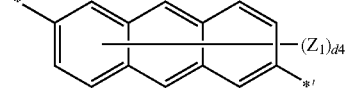

3-9

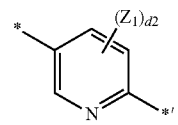

3-10

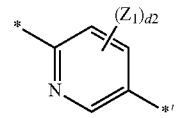

3-11

-continued
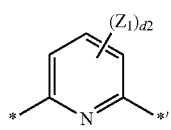
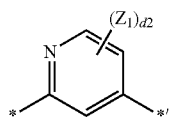
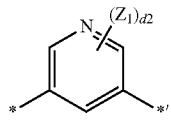
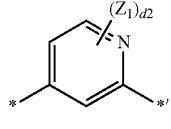
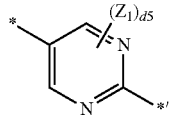
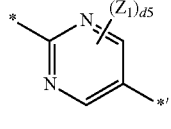
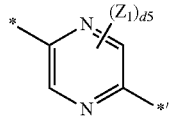
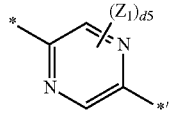
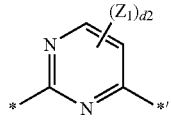
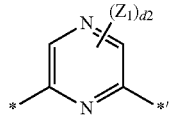
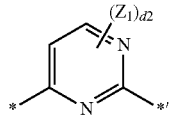
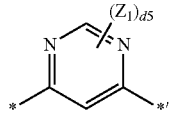
3-12
3-13
3-14
3-15
3-16
3-17
3-18
3-19
3-20
3-21
3-22
3-23
-continued
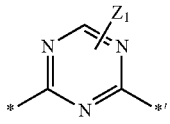
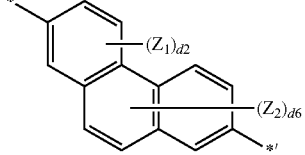
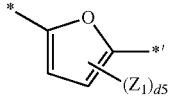
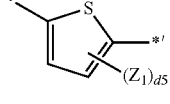
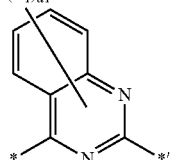
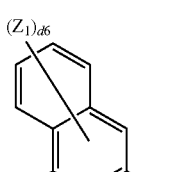
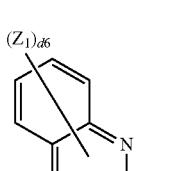
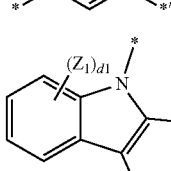
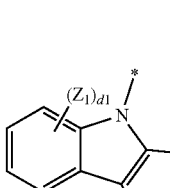
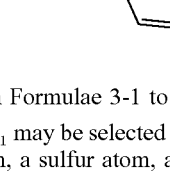
3-24
3-25
3-26
3-27
3-28
3-29
3-30
3-31
3-32
In Formulae 3-1 to 3-32,
$Y_1$ may be selected from $C(Q_{31})(Q_{32})$, $N(Q_{33})$, an oxygen atom, a sulfur atom, and $Si(Q_{34})(Q_{35})$, $Q_{31}$ to $Q_{35}$ may be each independently selected from a hydrogen, a deuterium, $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $Z_1$ and $Z_2$ may be each independently selected from a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1 to 4, d2 may be an integer selected from 1 to 3, d3 may be an integer selected from 1 to 6, d4 may be an integer selected from 1 to 8, d5 may be an integer selected from 1 or 2, and d6 may be an integer selected from 1 to 5.

In some other embodiments, $L_{11}$ in Formula 1 may be each independently a group represented by Formulae 4-1 to 4-23, but is not limited thereto:

4-1
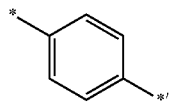

4-2
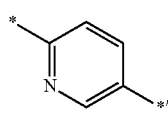

4-3
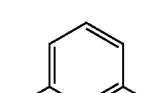

4-4
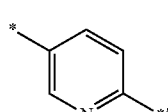

4-5
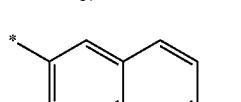

4-6
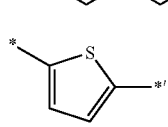

4-7
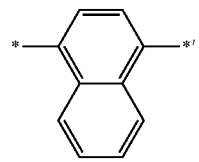

4-8
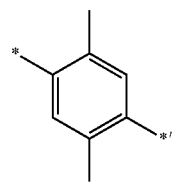

4-9
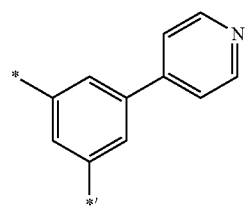

4-10
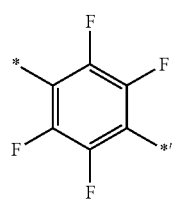

4-11
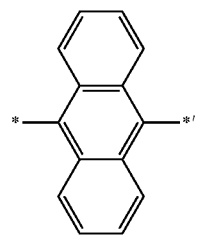

4-12
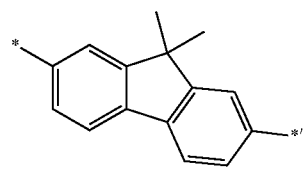

4-13
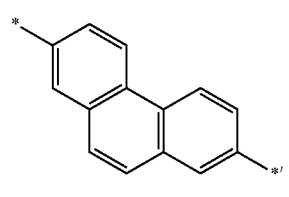

4-14
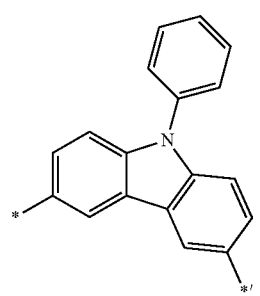

-continued

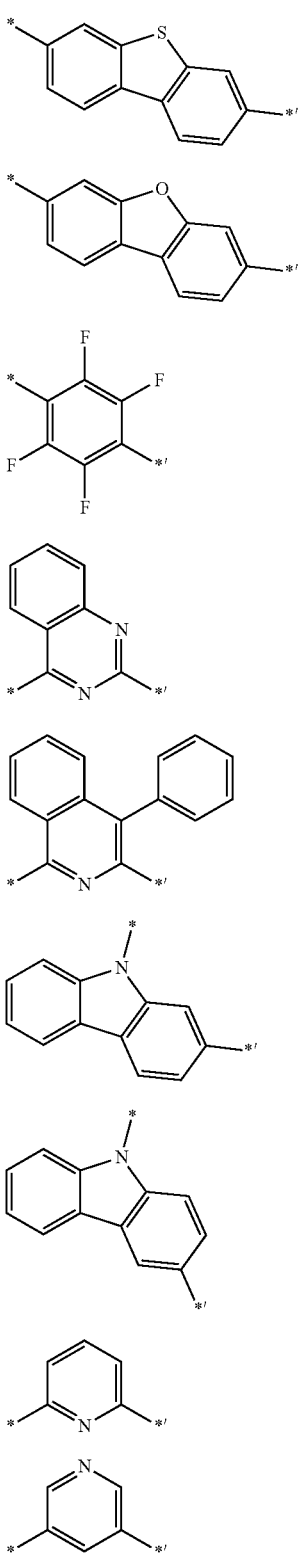

4-15
4-16
4-17
4-18
4-19
4-20
4-21
4-22
4-23

In Formula 1, n11, which indicates the number of $L_{11}$s, may be selected from 0, 1, 2, and 3, for example, may be 0 or 1, but is not limited thereto. In Formula 1, when n11 is 0, -$(L_{11})_{n11}$- may be a single bond. When n11 is 2 or greater, a plurality of $L_{11}$s may be identical to or different from each other.

In Formula 1, $R_{11}$ may be a group represented by one of Formulae 2-1 and 2-2:

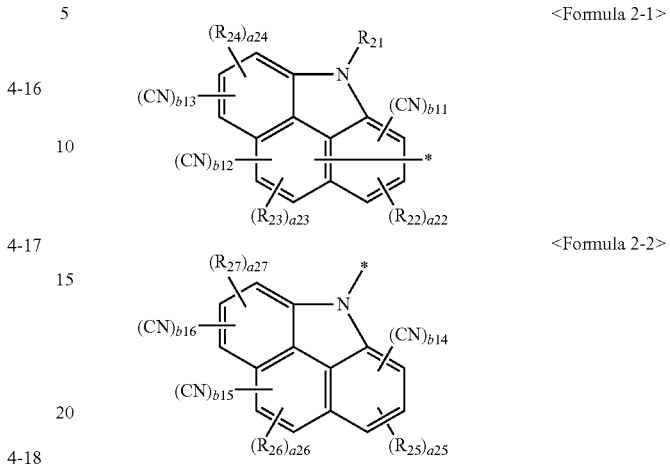

<Formula 2-1>

<Formula 2-2>

In Formulae 2-1 and 2-2, $R_{21}$ to $R_{27}$ may be each independently selected from:

a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, a22 to a27 may be each independently an integer selected from 0 to 3, b11 to b16 may be each independently an integer selected from 0 to 3, wherein a sum of b11, b12, and b13 may be 1 or greater, and a sum of b14, b15, and b16 may be 1 or greater, and

* may be a binding site to $L_{11}$ or a chrysene group in Formula 1.

In some other embodiments, $R_{11}$ in Formula 1 may be a group represented by one of Formulae 2-1a and 2-2a:

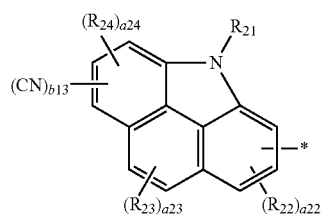

<Formula 2-1a>

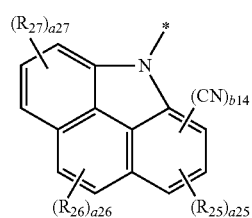

<Formula 2-2a>

In Formulae 2-1a and 2-2a, $R_{21}$ to $R_{27}$ may be each independently selected from:

a hydrogen, a deuterium, a halogen atom, a hydroxyl group, a cyano group, a nitro group, a $C_1$-$C_{60}$ alkyl group, and a $C_1$-$C_{60}$ alkoxy group;

a $C_1$-$C_{60}$ alkyl group and a $C_1$-$C_{60}$ alkoxy group, each substituted with at least one of a deuterium atom, a halogen atom, a hydroxyl group, a cyano group, a nitro group, a $C_6$-$C_{60}$ aryl group, a $C_2$-$C_{60}$ heteroaryl group, and a non-aromatic condensed polycyclic group;

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group, a22 to a27 are each independently an integer selected from 0 to 3, b13 and b14 are each independently an integer selected from 1 and 2, and

* is a binding site to $L_{11}$ or the chrysene group in Formula 1.

In some other embodiments, in Formula 1, $R_{11}$ may be a group represented by Formula 2-1b:

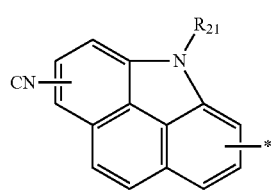

<Formula 2-1b>

In Formula 2-1b, $R_{21}$ may be selected from:

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group, and

* is a binding site to $L_{11}$ or the chrysene group in Formula 1.

For example, in Formulae 2-1, 2-2, 2-1a, and 2-2a, $R_{21}$ may be selected from:

a hydrogen, a deuterium, a methyl group, an ethyl group, a tert-butyl group, a methoxy group, an ethoxy group, and a tert-butoxy group;

a methyl group, an ethyl group, a tert-butyl group, a methoxy group, an ethoxy group, and a tert-butoxy group, each substituted with at least one of a deuterium atom, a halogen atom, a cyano group, a nitro group, a phenyl group, a naphthyl group, a pyridinyl group, a fluorenyl group, and a carbazolyl group;

a phenyl group, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group, but is not limited thereto.

In some other embodiments, in Formulae 2-1, 2-2, 2-1a, 2-2a, and 2-1b, $R_{21}$ may be selected from:

a phenyl group, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group, but is not limited thereto.

For example, in Formulae 2-1, 2-2, 2-1a, and 2-2a, $R_{22}$ to $R_{27}$ may be each independently selected from a hydrogen, a deuterium, a halogen atom, a cyano group, a nitro group, a methyl group, an ethyl group, a tert-butyl group, a methoxy group, an ethoxy group, and a tert-butoxy group;

a methyl group, an ethyl group, a tert-butyl group, a methoxy group, an ethoxy group, and a tert-butoxy group, each substituted with at least one of a deuterium atom, a halogen atom, a cyano group, a nitro group, a phenyl group, a naphthyl group, a pyridinyl group, a fluorenyl group, and a carbazolyl group;

a phenyl group, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group, but is not limited thereto.

In Formula 1, m11, which indicates the number of $R_{11}$s, may be an integer selected from 1 to 3, for example, may be 1, but is not limited thereto. When ml 1 is 2 or greater, a plurality of $R_{11}$s may be identical to or different from each other.

In Formula 1, $R_{12}$ to $R_{14}$ may be each independently selected from:

a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group.

In some embodiments, in Formula 1, $R_{12}$ to $R_{14}$ may be each independently selected from:

a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

In some other embodiments, in Formula 1, $R_{12}$ to $R_{14}$ may be each independently selected from:

a hydrogen, a deuterium, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group;

a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group; and a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one substituent selected from a deuterium, a halogen atom, a cyano group, a nitro group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

In some other embodiments, in Formula 1, $R_{12}$ may be selected from a hydrogen, a deuterium, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and groups represented by Formulae 5-1 to 5-38, but is not limited thereto:

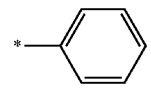

5-1

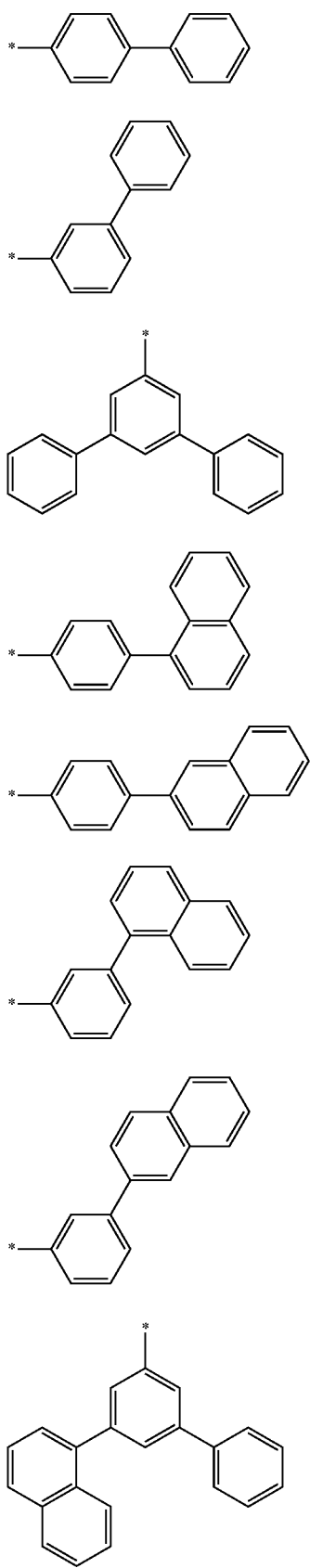
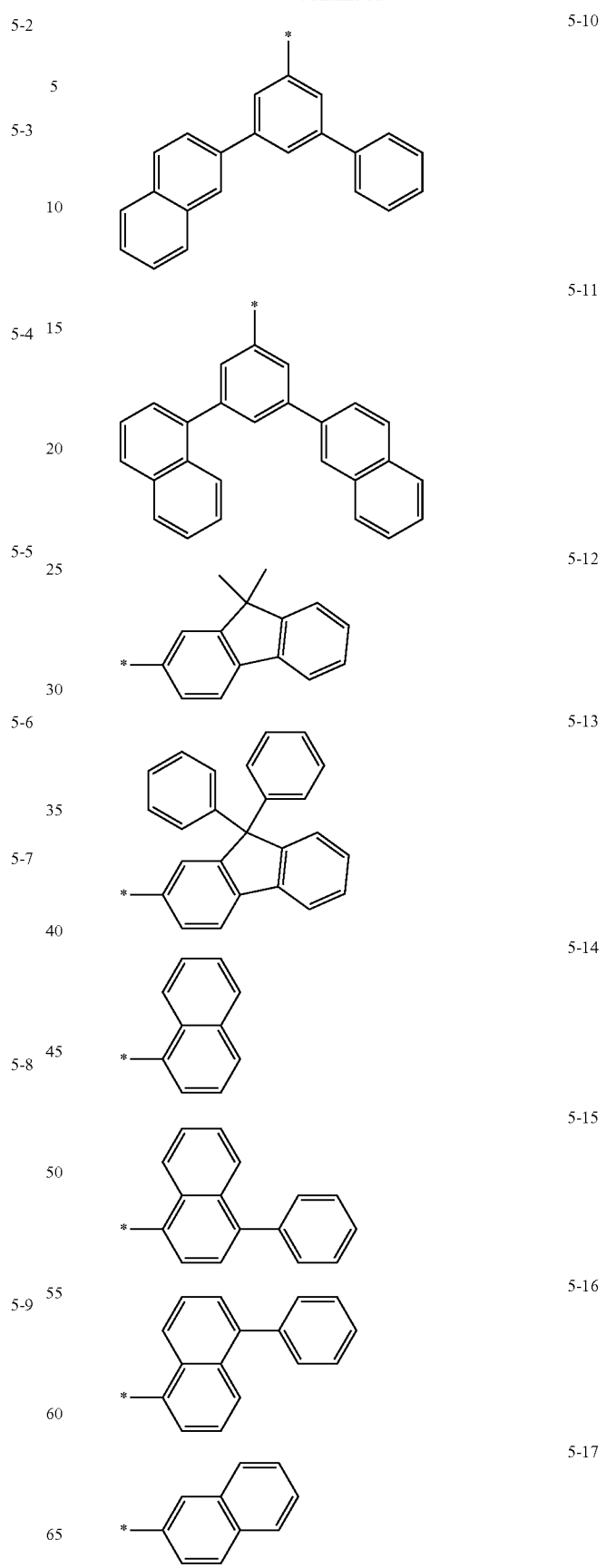

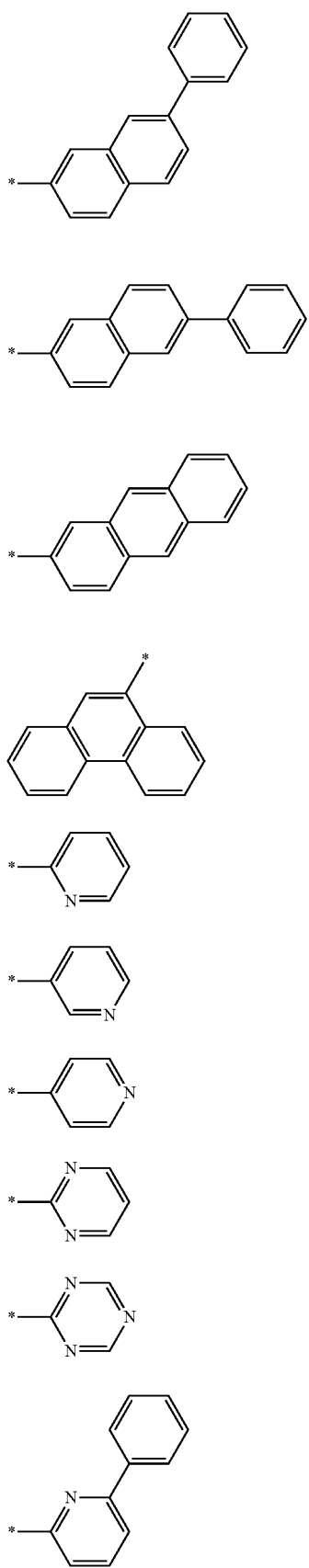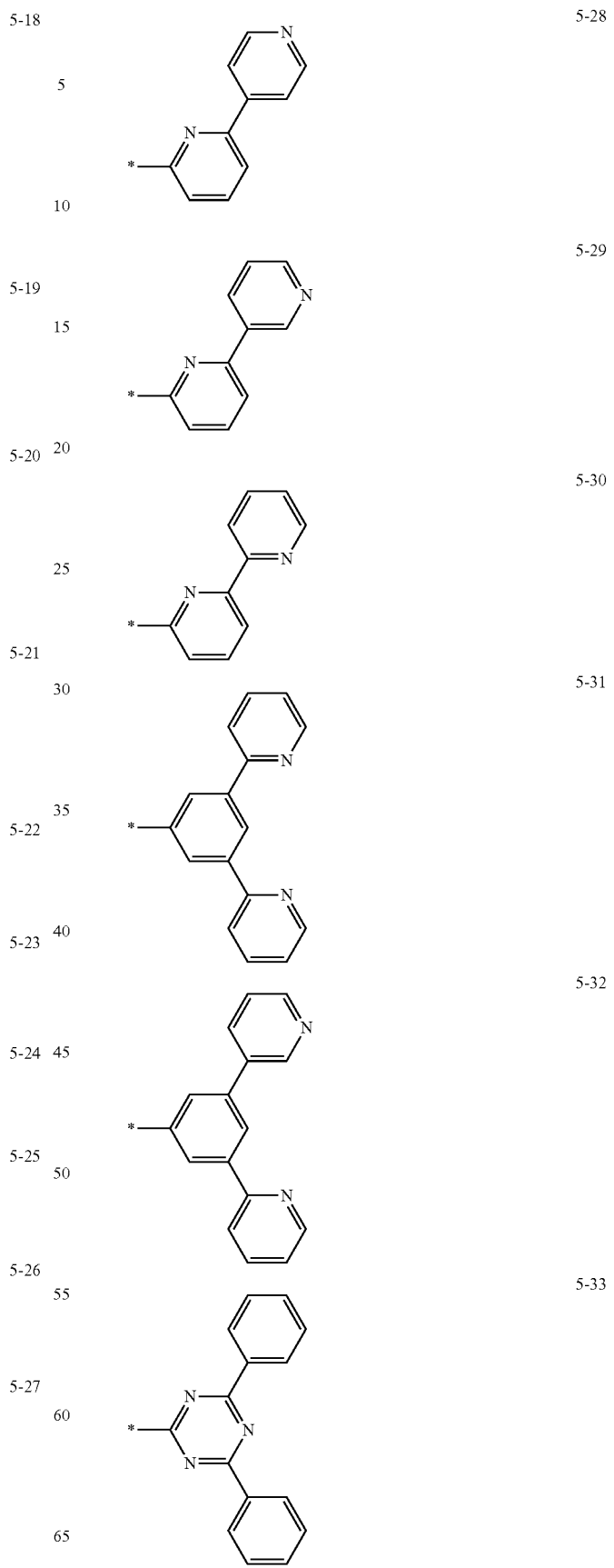

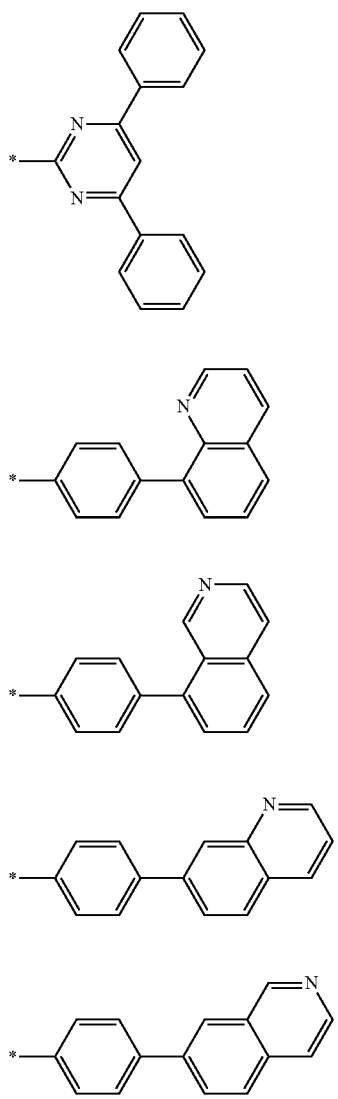

5-34

5-35

5-36

5-37

5-38

In some embodiments, in Formula 1, $R_{13}$ and $R_{14}$ may be each independently selected from a hydrogen, a deuterium, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group, but is not limited thereto.

In Formula 1, a12, which indicates the number of $R_{12}$s, may be an integer selected from 0 to 3. When a12 is 2 or greater, a plurality of $R_{12}$s may be identical to or different from each other. For example, a12 may be 1, but is not limited thereto.

In Formula 1, a13, which indicates the number of $R_{13}$s, may be an integer selected from 0 to 3. When a12 is 2 or greater, a plurality of $R_{13}$s may be identical to or different from each other.

In Formula 1, a14, which indicates the number of $R_{14}$s, may be an integer selected from 0 to 3. When a14 is 2 or greater, a plurality of $R_{14}$s may be identical to or different from each other.

In some embodiments, the chrysene-based compound of Formula 1 may be a group represented by Formula 1-1 below, but is not limited thereto:

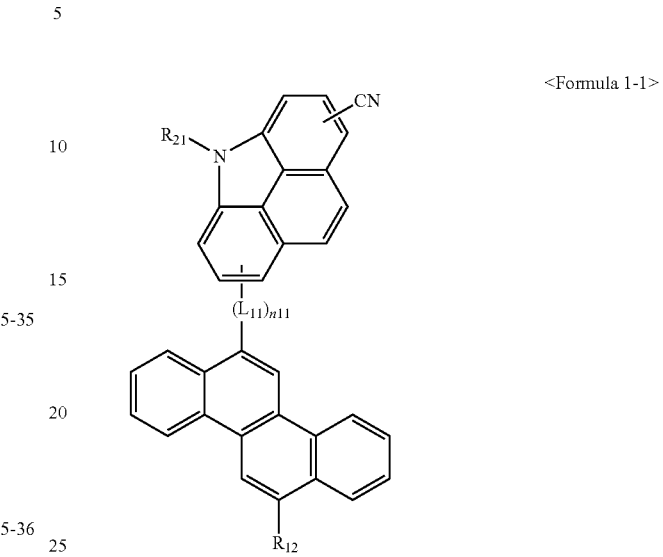

<Formula 1-1> wherein $L_{11}$, n11, $R_{12}$, and $R_{21}$ in Formula 1-1 may be the same as those described above herein in conjunction with other formulae, e.g., Formula 1.

For example, the chrysene-based compound of Formula 1 may be a compound represented by Formula 1-1, wherein $L_{11}$ in Formula 1-1 may be a group represented by one of Formulae 4-1 to 4-23.

In some other embodiments, the chrysene-based compound of Formula 1 may be a compound represented by Formula 1-1, wherein n11 in Formula 1-1 may be 0 or 1.

In still other embodiments, the chrysene-based compound of Formula 1 may be a compound represented by Formula 1-1, wherein $R_{12}$ in Formula 1-1 may be selected from a hydrogen, a deuterium, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and groups represented by Formulae 5-1 to 5-34.

In yet other embodiments, the chrysene-based compound of Formula 1 may be a compound represented by Formula 1-1, wherein $R_{21}$ in Formula 1-1 may be selected from:

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group.

For example, the chrysene-based compound of Formula 1 may be at least one of Compounds 1 to 74, but is not limited thereto:

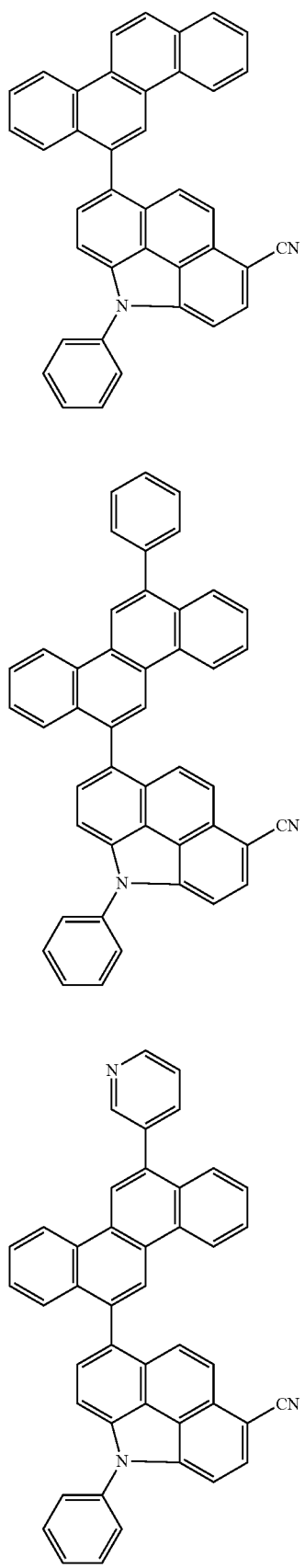
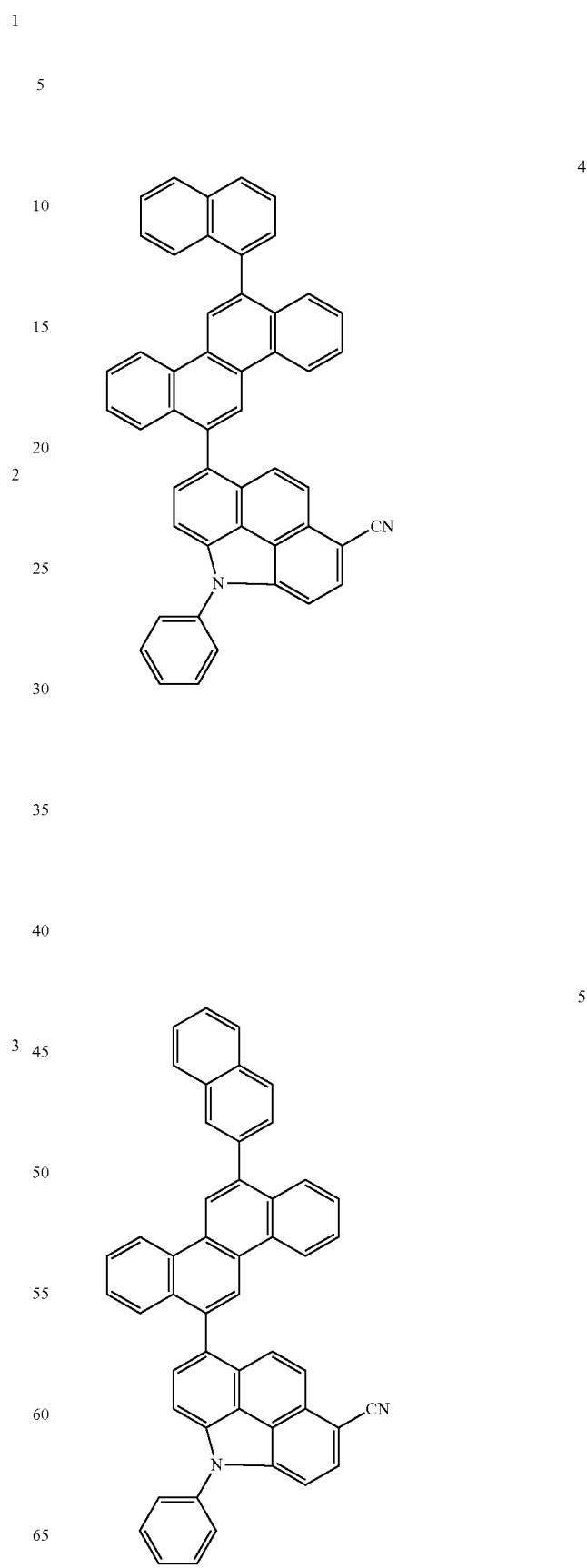

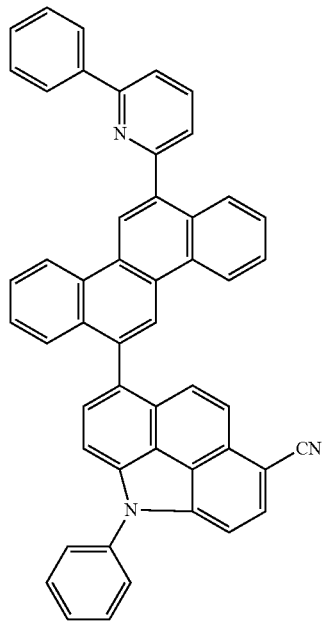
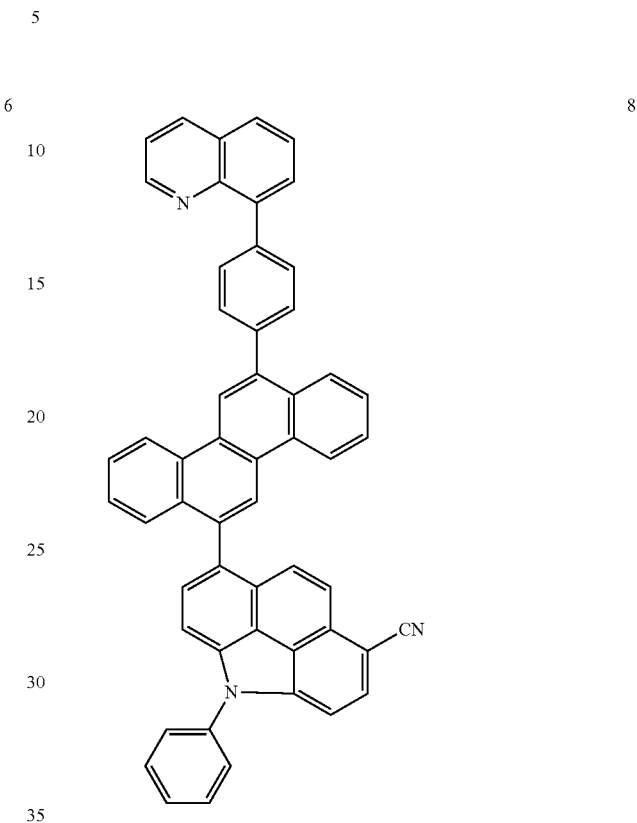
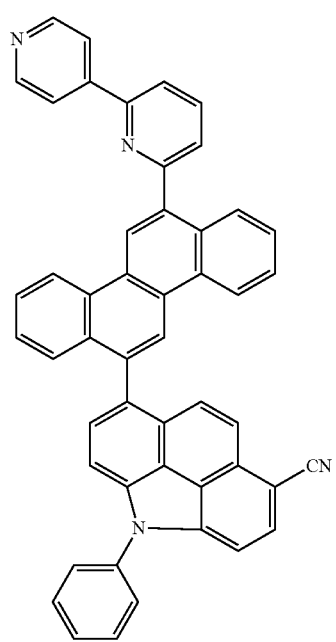
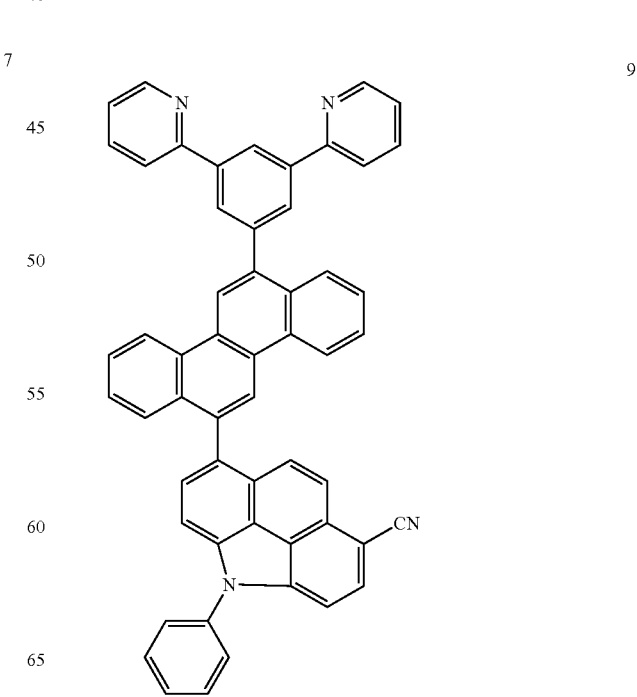

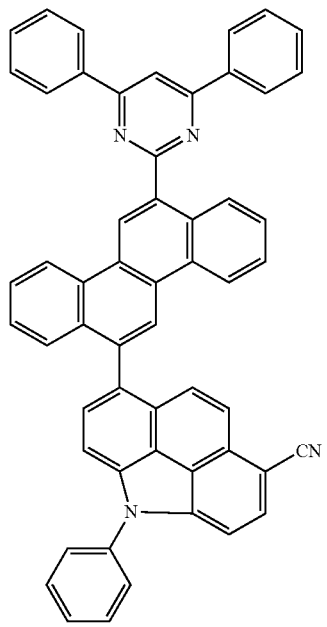
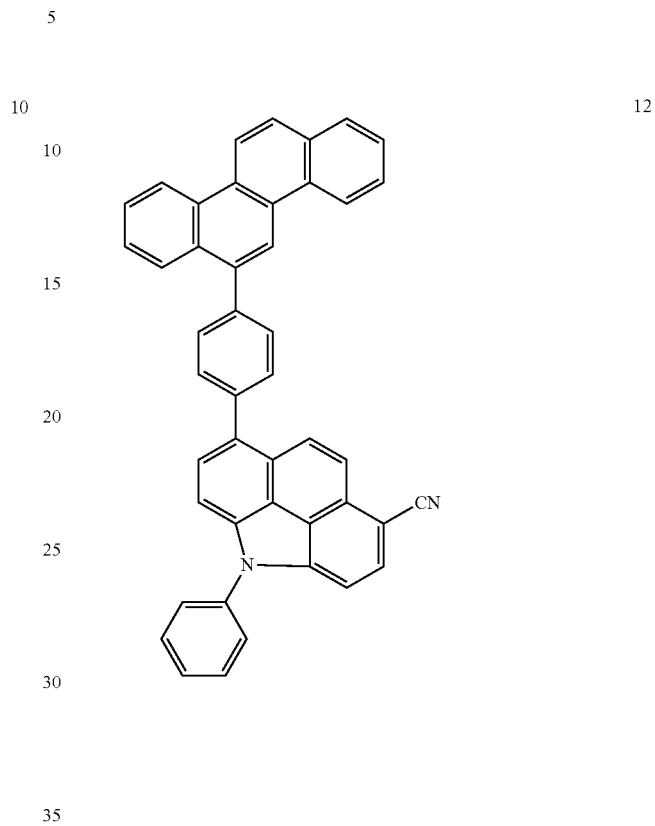
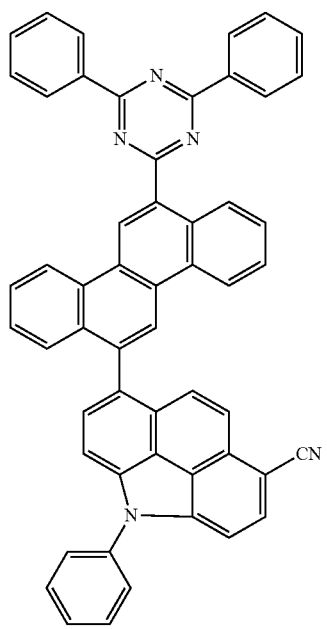
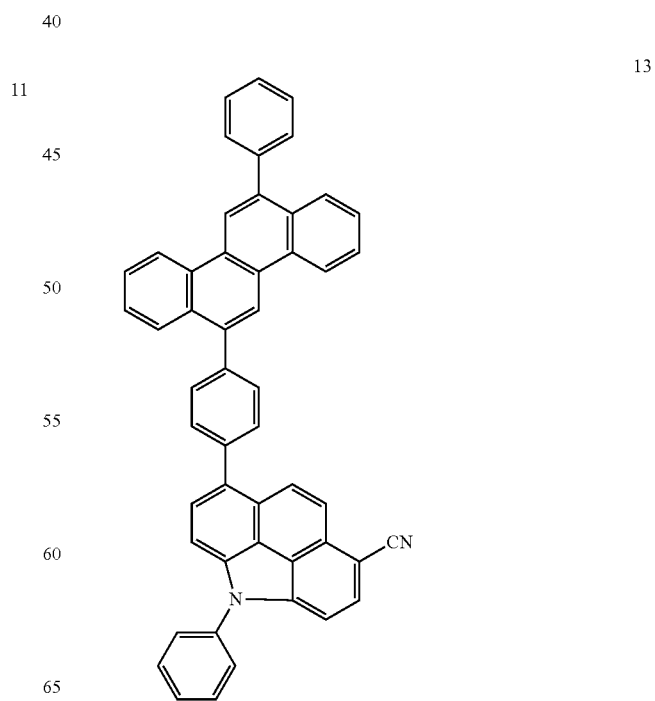

31
-continued
32
-continued
14
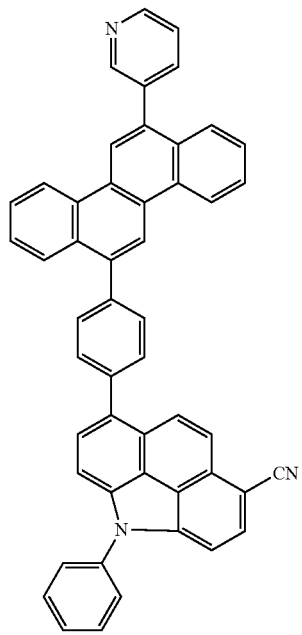
5
10
15
20
25
30
35
40
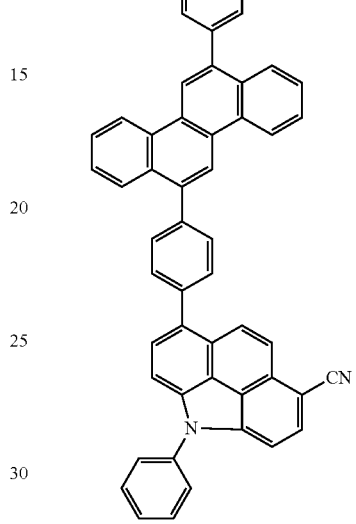
15
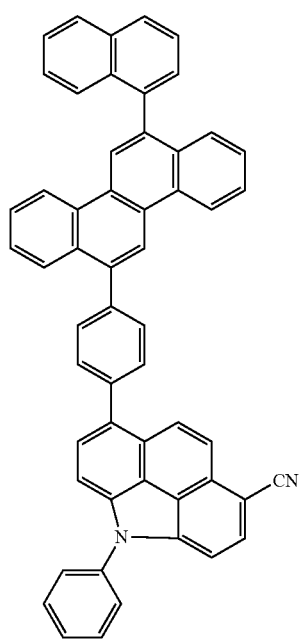
45
50
55
60
65
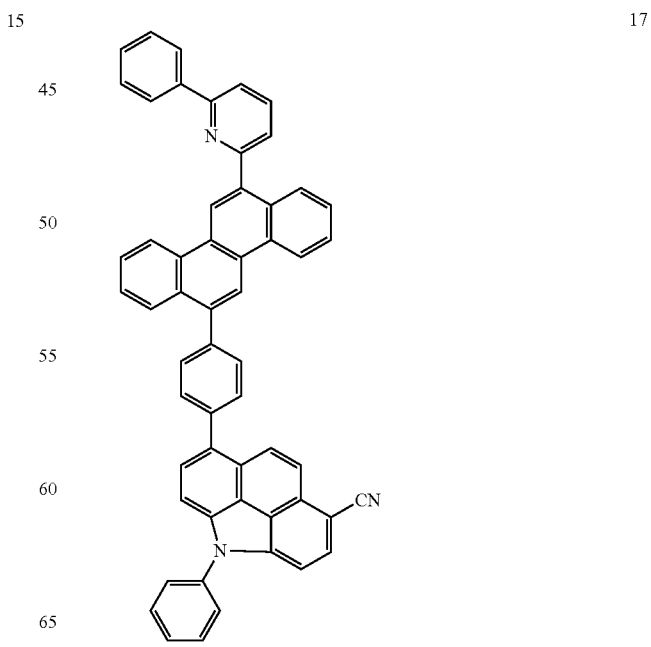

-continued
18
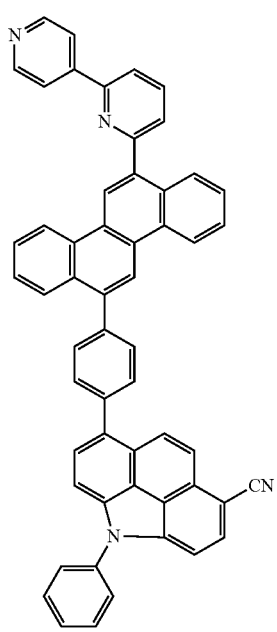
19
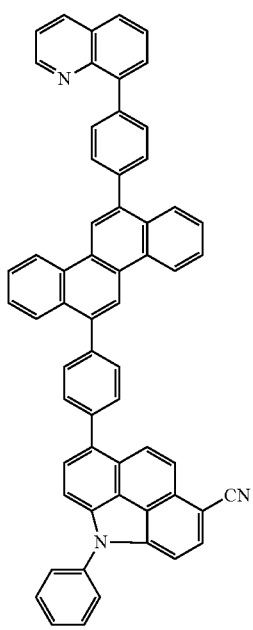
-continued
20
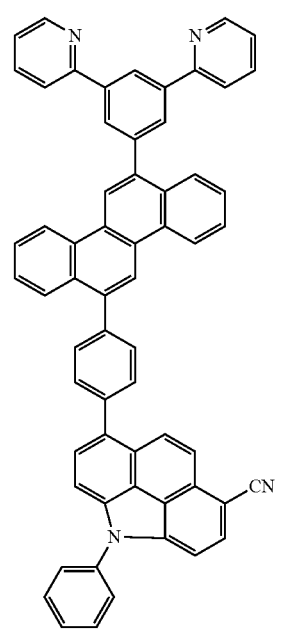
21
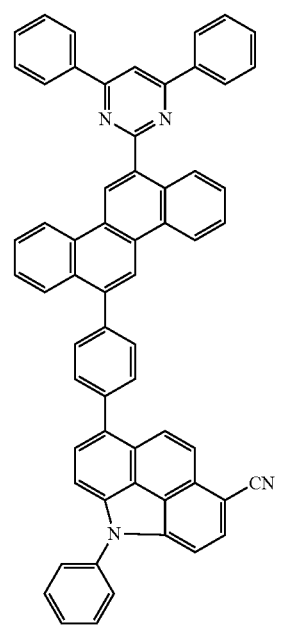

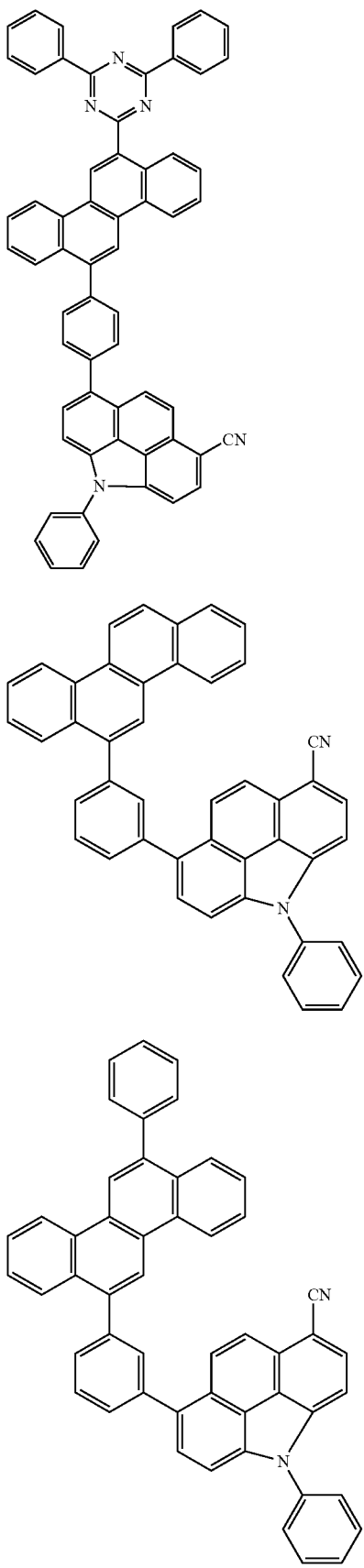
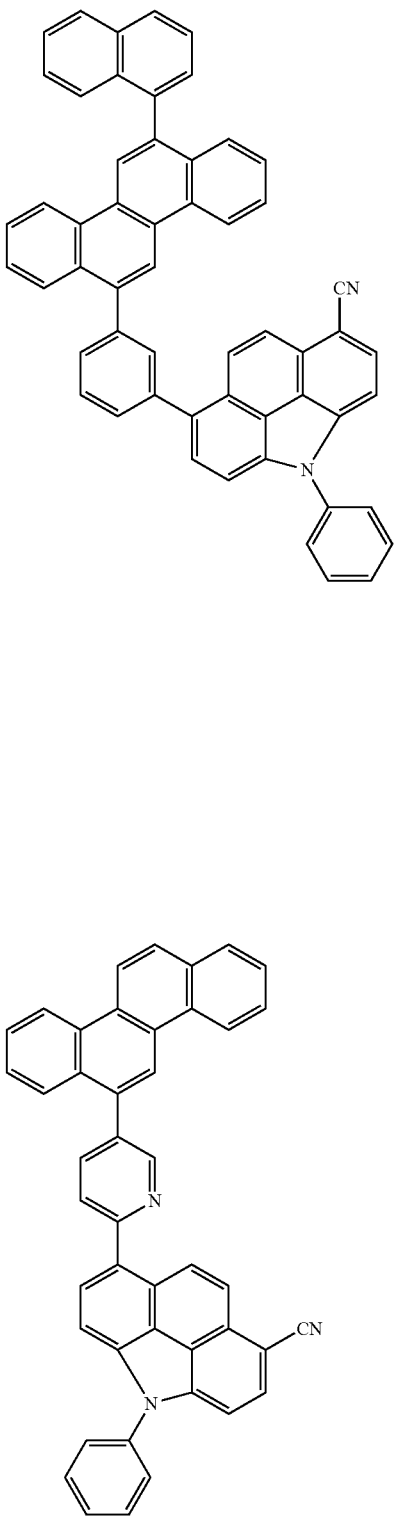

27
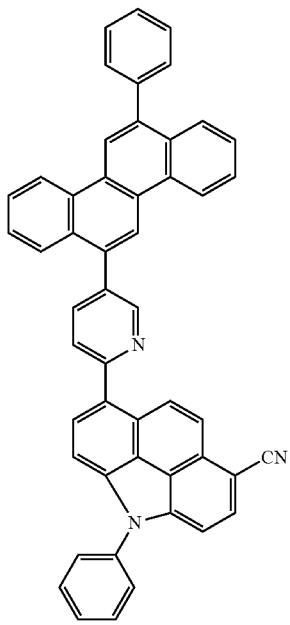
28
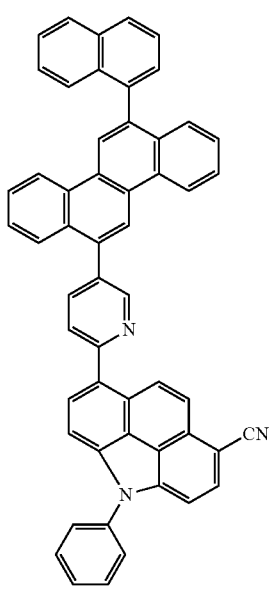
29
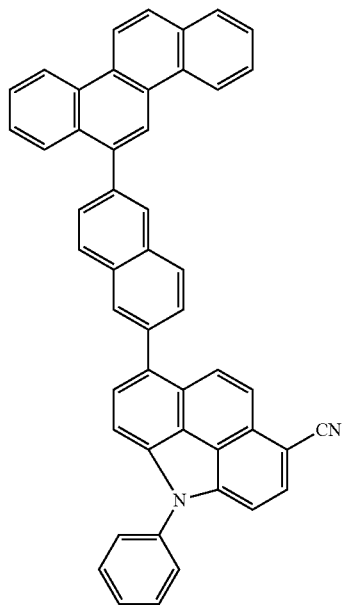
30
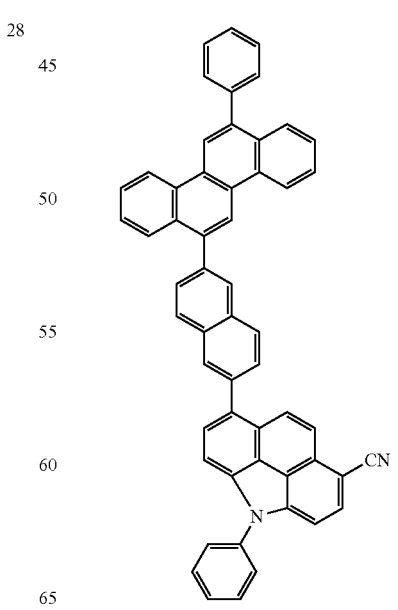

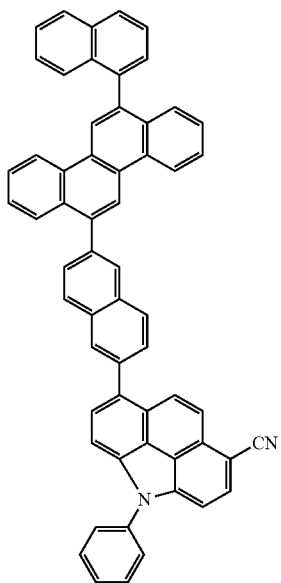
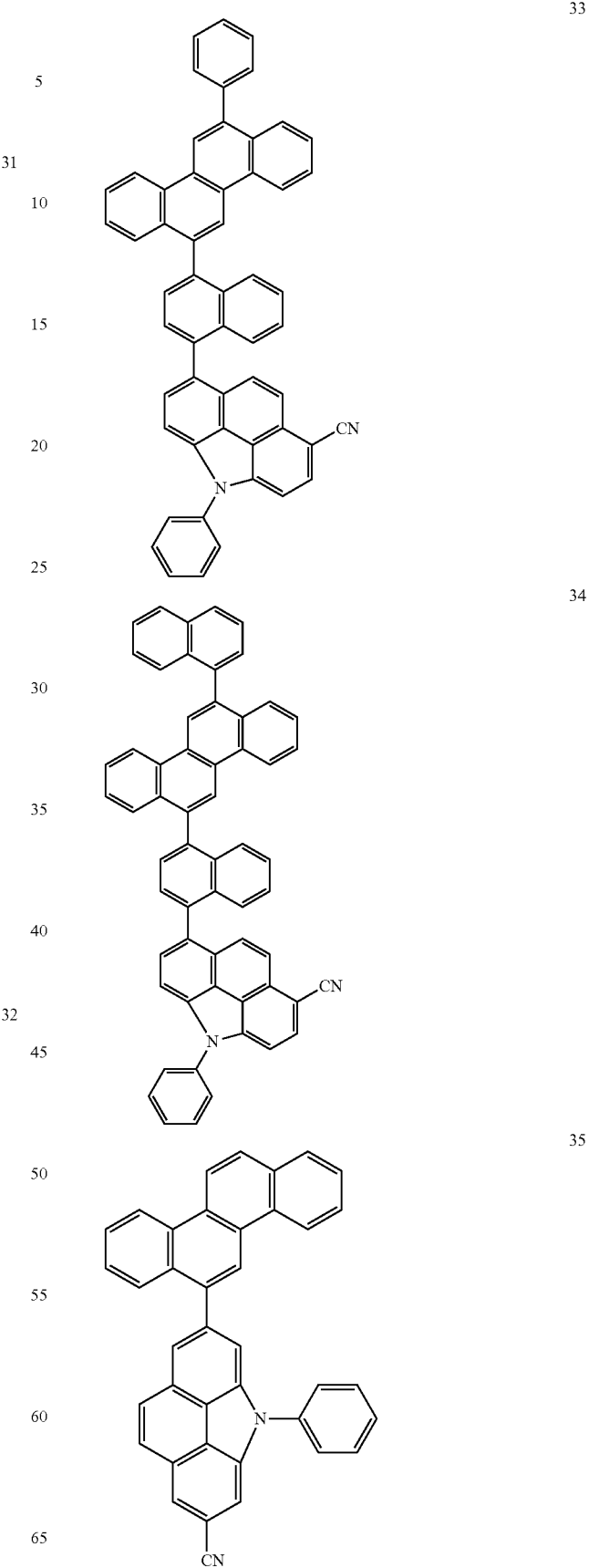

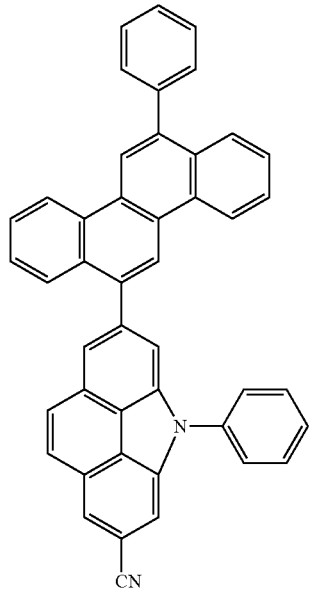

40
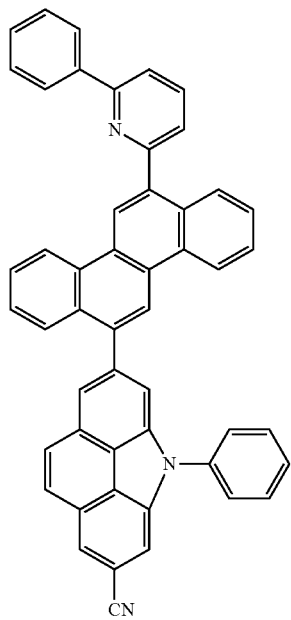
41
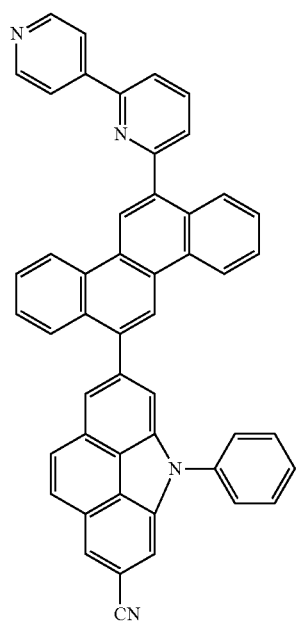
42
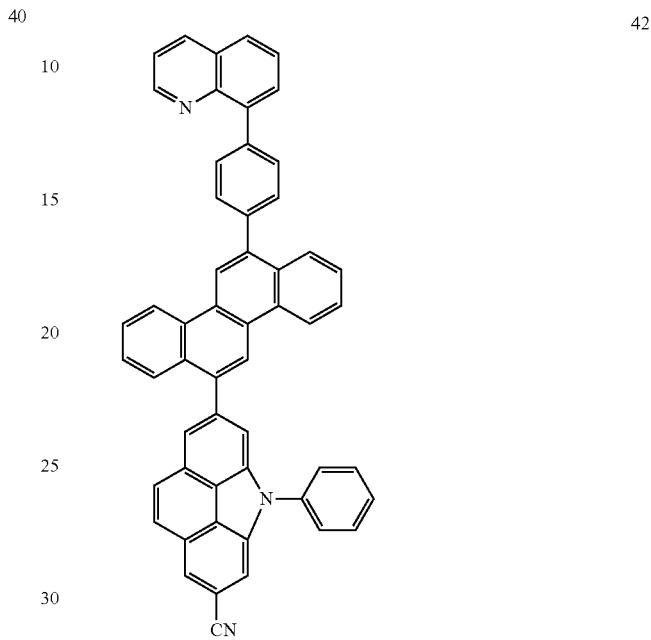
43
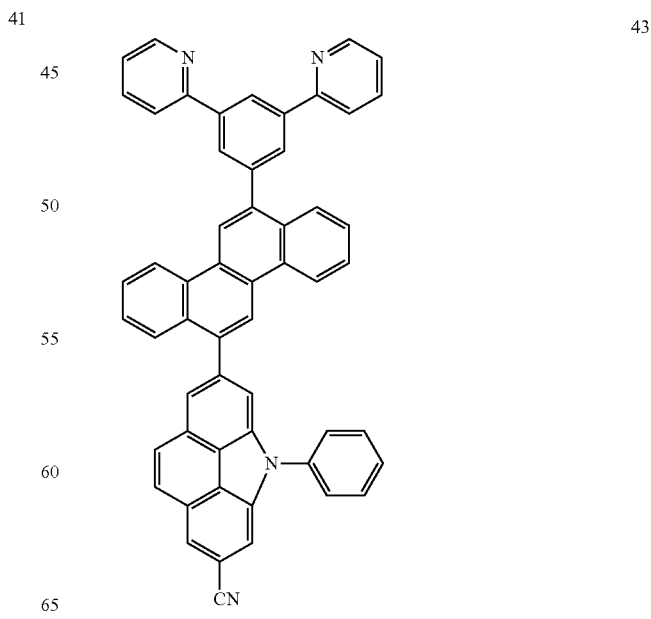

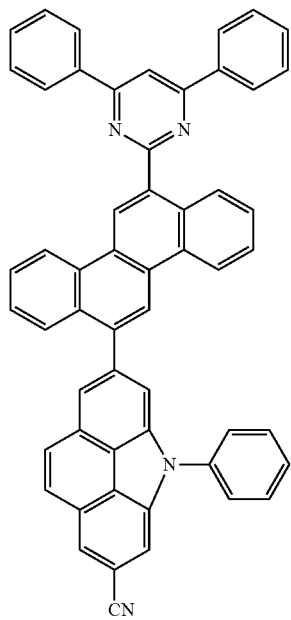
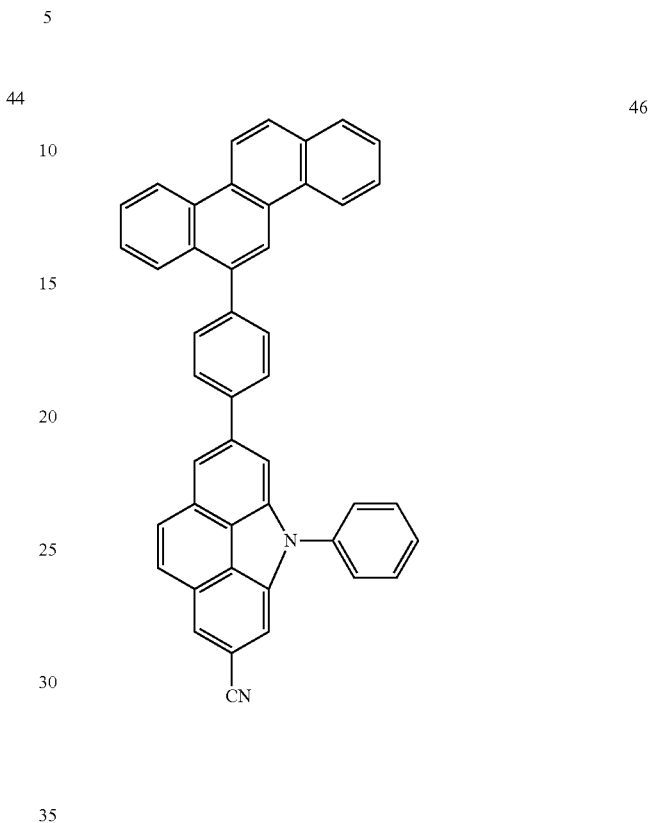
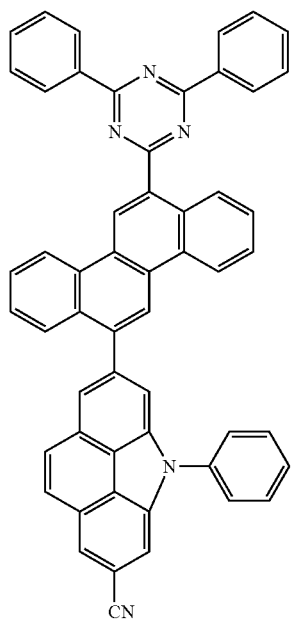
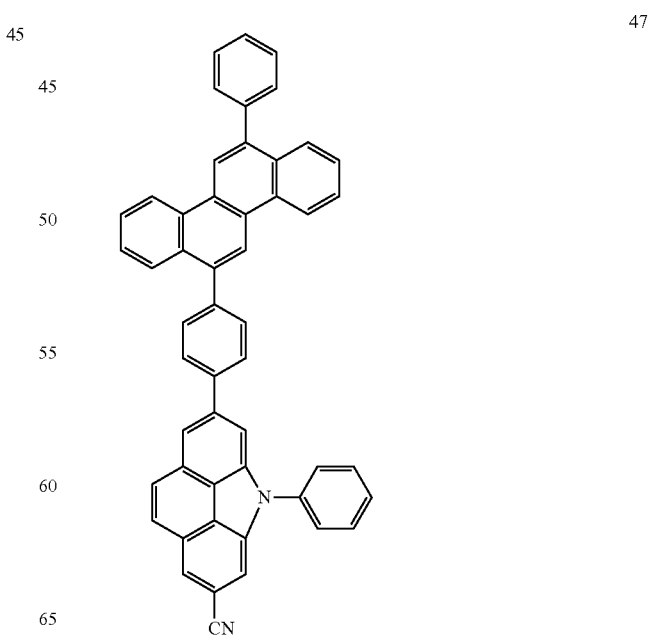

47
48
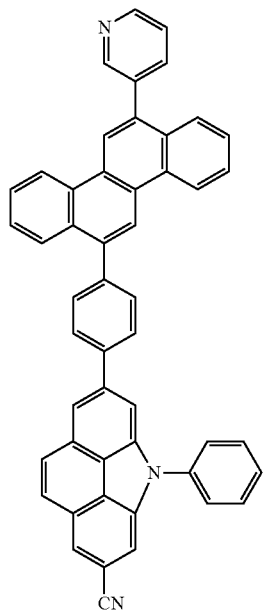
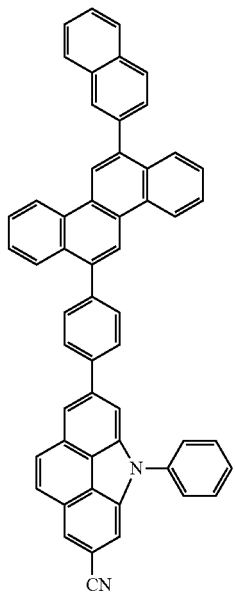
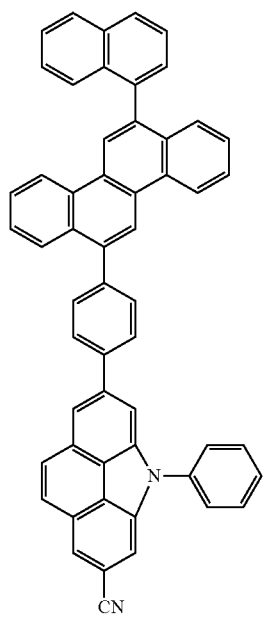
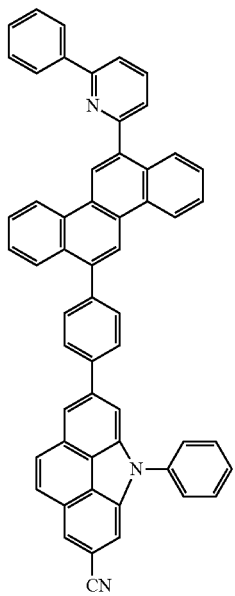

51
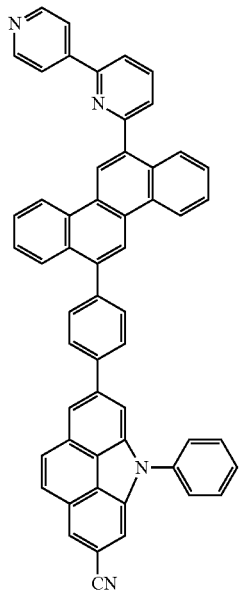
52
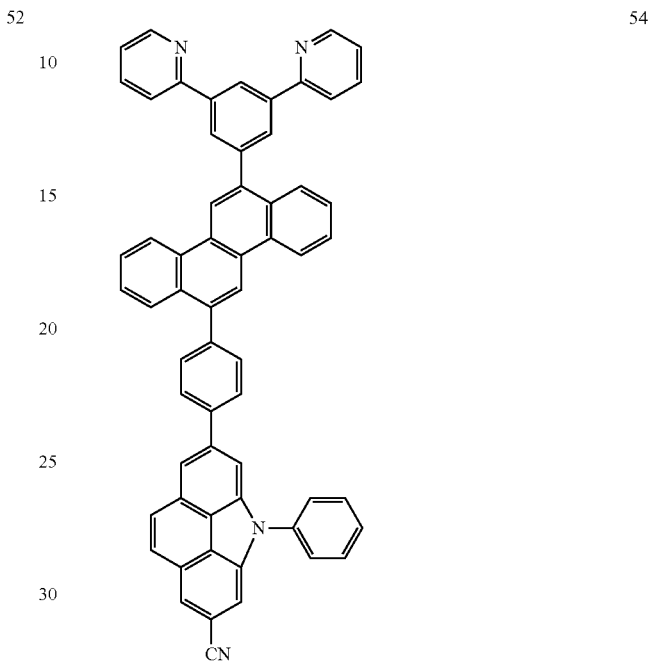
53
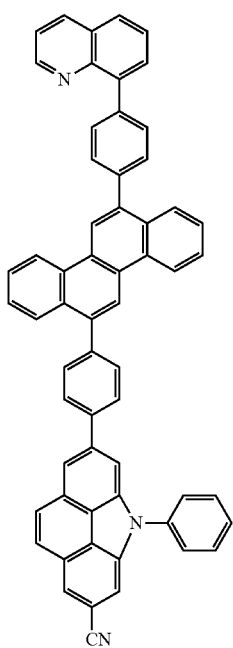
54
55
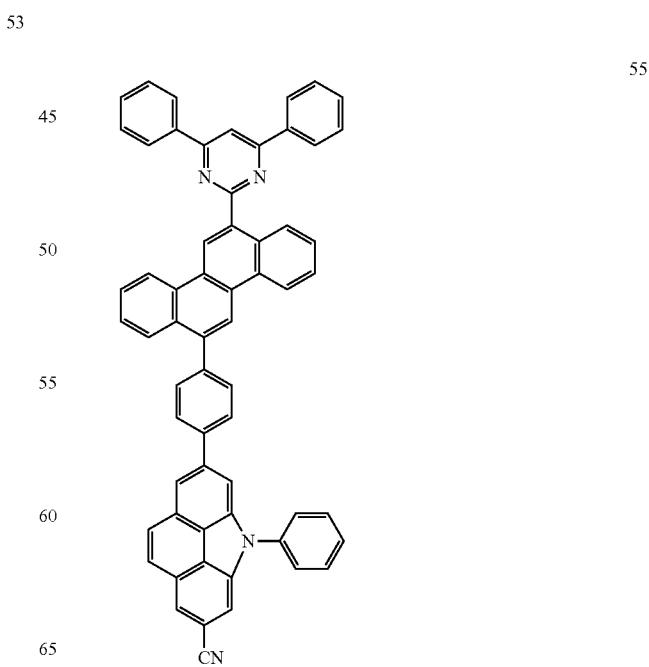

51
-continued
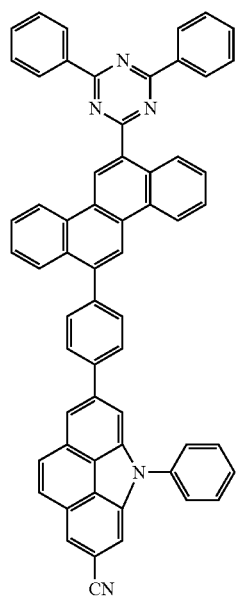
52
-continued
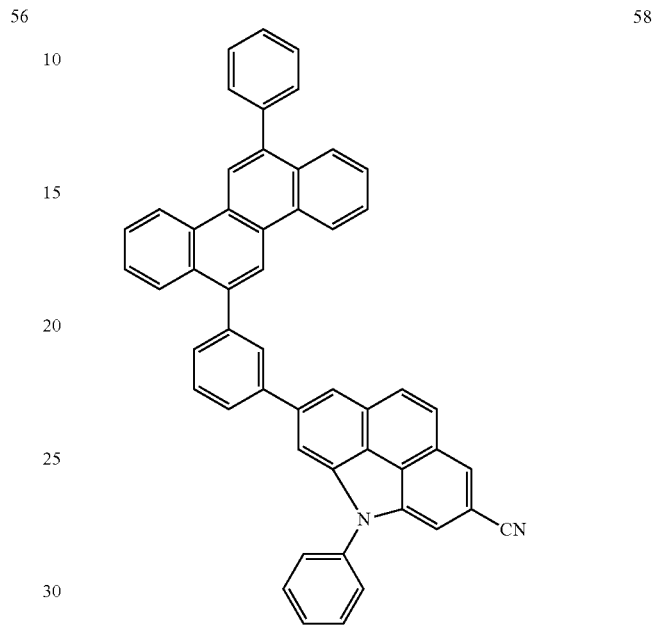
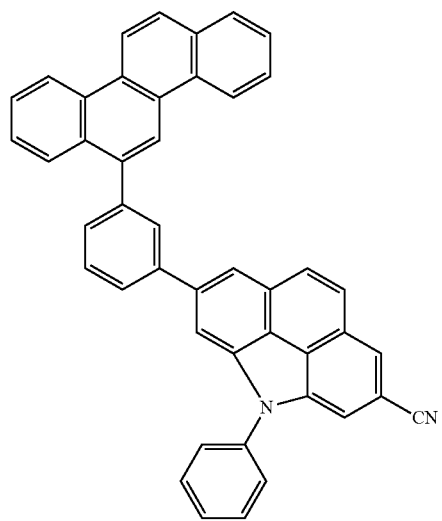
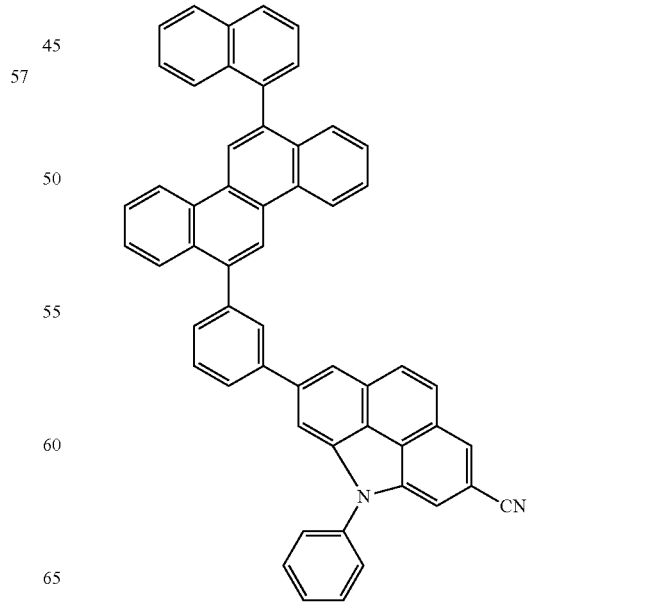

53
-continued
54
-continued
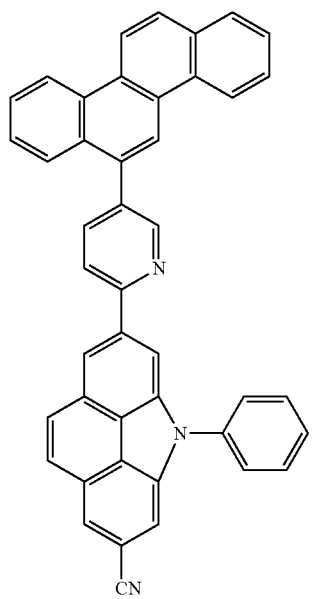
60
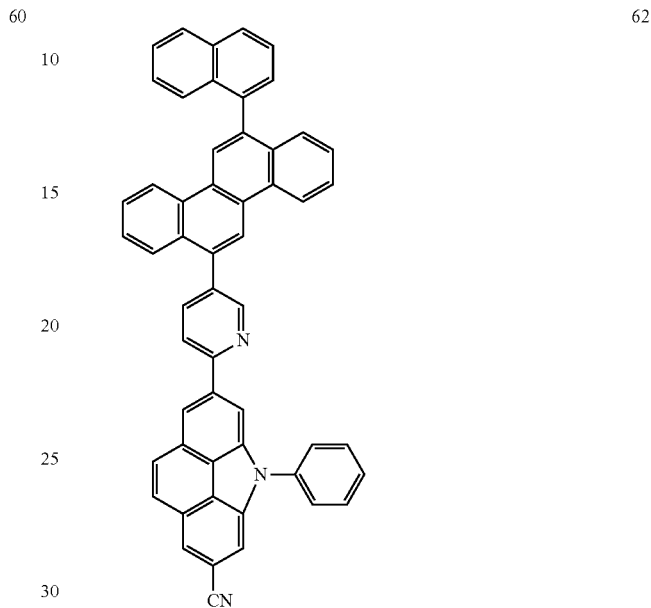
62
61
63
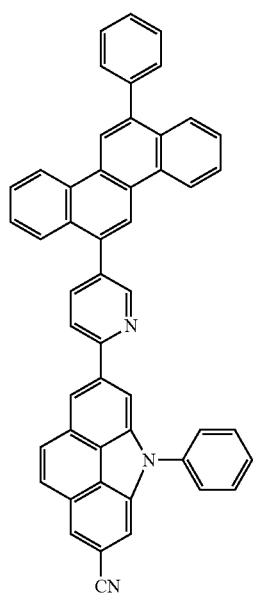
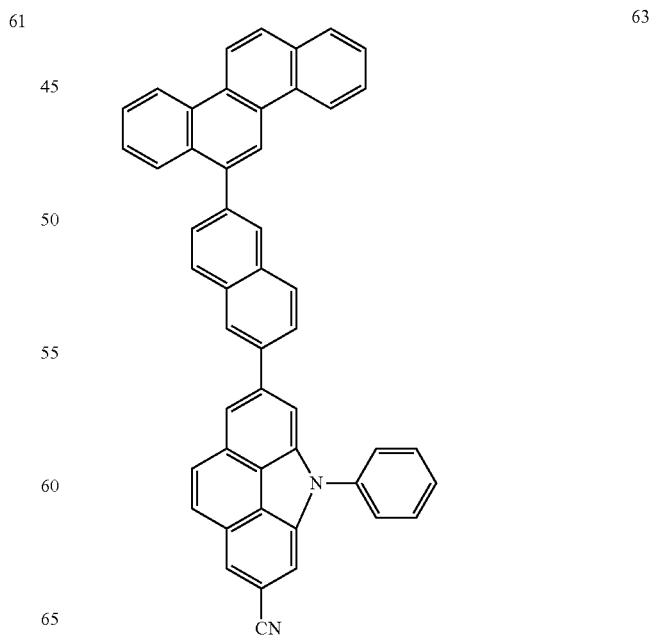

64
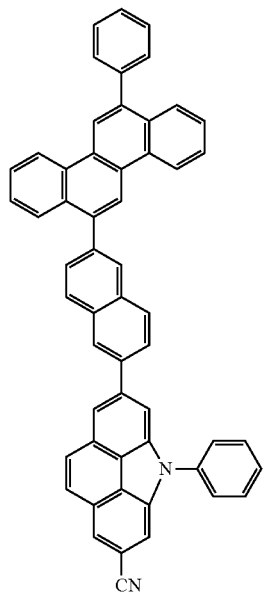
66
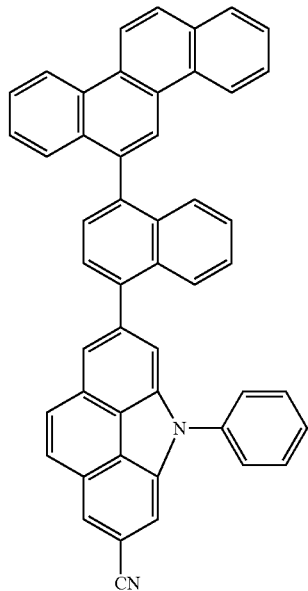
65
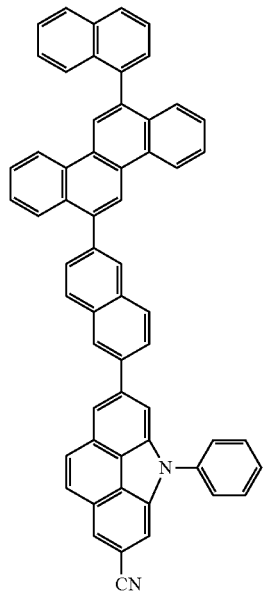
67
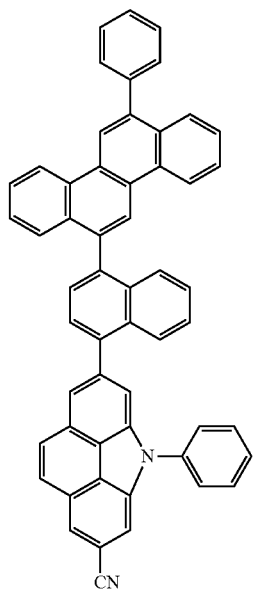

57
-continued
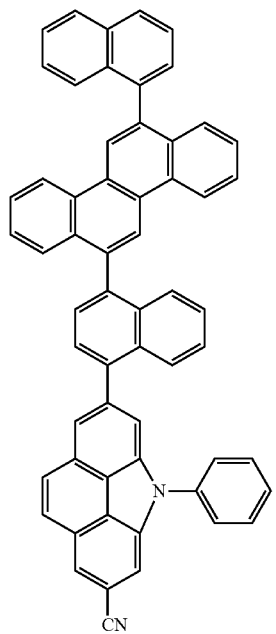
68
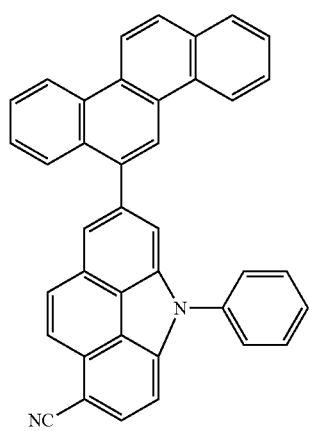
69
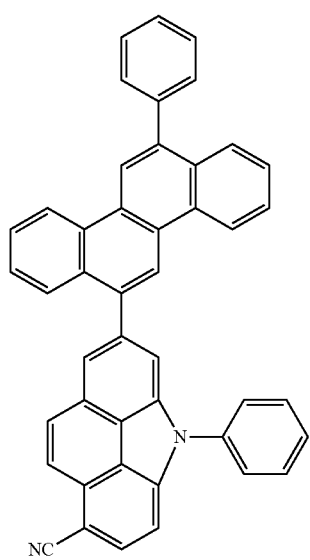
70
58
-continued
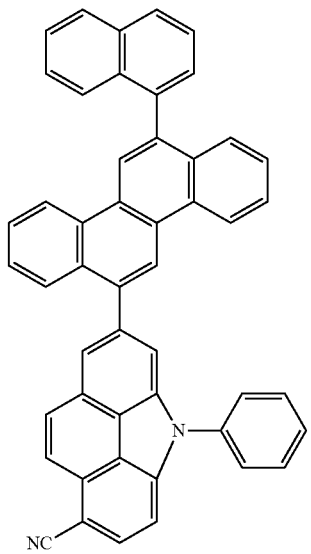
71
72

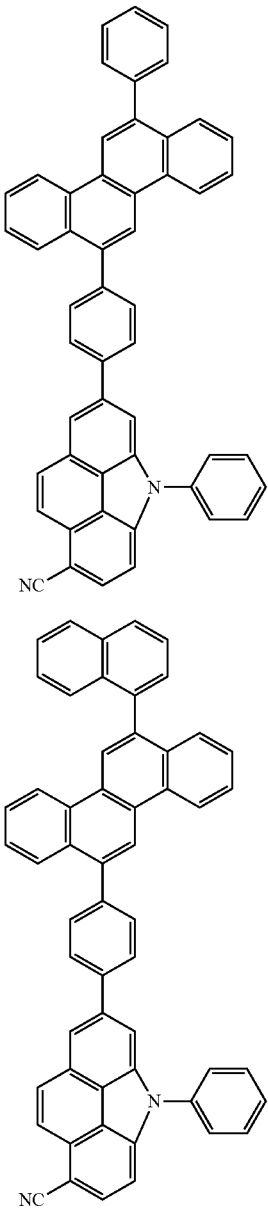

The chrysene-based compound of Formula 1 includes both electron-rich chrysene and a benzocarbazole substituted with electron-deficient CN, and thus may form an electron dipole in the molecule thereof. Accordingly, migration of electrons in the chrysene-based compound of Formula 1 may be facilitated. Furthermore, the chrysene-based compound of Formula 1 may facilitate electron transfer to a host or dopant in the EML.

The chrysene-based compound of Formula 1 above includes a benzocarbazole, and thus may have a high glass transition temperature (Tg). Therefore, an organic light-emitting device including the chrysene-based compound of Formula 1 may have improved thermal stability and improved lifetime.

Therefore, an organic light-emitting device including any of the chrysene-based compounds represented by Formula 1 above may have a high efficiency, a high luminance, and a long lifetime.

The chrysene-based compound of Formula 1 may be synthesized using a suitable organic synthesis method. Methods of synthesizing the chrysene-based compounds of Formula 1 may be understood based on the examples that will be described below.

The chrysene-based compound of Formula 1 above may be used between a pair of electrodes of an organic light-emitting device. For example, the chrysene-based compound of Formula 1 may be in an electron transport region, such as, in an electron transport layer.

According to another embodiment, an organic light-emitting device includes a first electrode, a second electrode disposed opposite to the first electrode, and an organic layer disposed between the first electrode and the second electrode and including an emission layer, wherein the organic layer includes at least one of the chrysene-based compounds of Formula 1 described above.

As used herein, "(for example, the organic layer) including at least one chrysene-based compound means that "(the organic layer) including one of the chrysene-based compounds of Formula 1 above, or at least two different chrysene-based compounds of Formula 1 above".

In some embodiments, the organic layer may include only Compound 1 above as a chrysene-based compound. In this regard, Compound 1 may be present in the electron transport layer of the organic light-emitting device. In some embodiments, the organic layer may include Compounds 1 and 2 as chrysene-based compounds. In this regard, Compounds 1 and 2 may be present both in the same layer (for example, in the electron transport region) or may be present in different layers (for example, in the emission layer and the electron transport region, respectively).

The organic layer may further include a hole transport region disposed between the first electrode and the emission layer, and the hole transport region may include at least one of a hole injection layer, a hole transport layer, a buffer layer, and an electron blocking layer The organic layer may further include an electron transport region disposed between the emission layer and the second electrode, and the electron transport region may include at least one of a hole blocking layer, an electron transport layer, and an electron injection layer. The electron transport region may include the chrysene-based compound represented by Formula 1 above. For example, the electron transport region may include an electron transport layer, and the electron transport layer may include the chrysene-based compound represented by Formula 1 above.

As used herein, the term "organic layer" refers to a single layer and/or a plurality of layers disposed between the first and second electrodes of the organic light-emitting device. A material in the "organic layer" is not limited to an organic material.

Hereinafter, a structure of an organic light-emitting device according to an embodiment and a method of manufacturing the same will now be described with reference to FIG. 1.

FIG. 1 illustrates a schematic sectional view of an organic light-emitting device 10 according to an embodiment. Referring to FIG. 1, the organic light-emitting device 10 includes a first electrode 110, an organic layer 150, and a second electrode 190.

A substrate (not shown) may be disposed under the first electrode 110 or on the second electrode 190 in FIG. 1. The substrate may be a glass or transparent plastic substrate with good mechanical strength, thermal stability, transparency, surface smoothness, ease of handling, and water resistance.

For example, the first electrode 110 may be formed by depositing or sputtering a first electrode-forming material on the substrate 11. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but is not limited thereto.

The organic layer 150 may be disposed on the first electrode 110. The organic layer 150 may include an emission layer (EML).

The organic layer 150 may further include a hole transport region disposed between the first electrode and the EML. The organic layer 150 may further include an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL). However, embodiments are not limited thereto.

The hole transport region may have a single-layered structure including a single material, a single-layered structure including a plurality of materials, or a multi-layered structure including a plurality of layers including different materials.

In some embodiments, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above. However, embodiments are not limited thereto.

When the hole transport region includes a HIL, the HIL may be formed on the first electrode 110 by using any of a variety of methods, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 5 pm and a heat treatment temperature of about 800° C. to about 200° C.

When the hole transport region includes a HTL, the HTL may be formed on the first electrode 110 or the HIL by using any of a variety of methods, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly will not be described in detail.

In some embodiments, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA). polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula

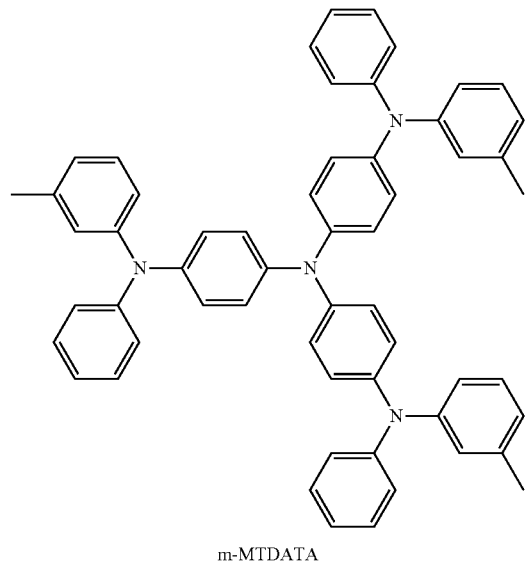

m-MTDATA

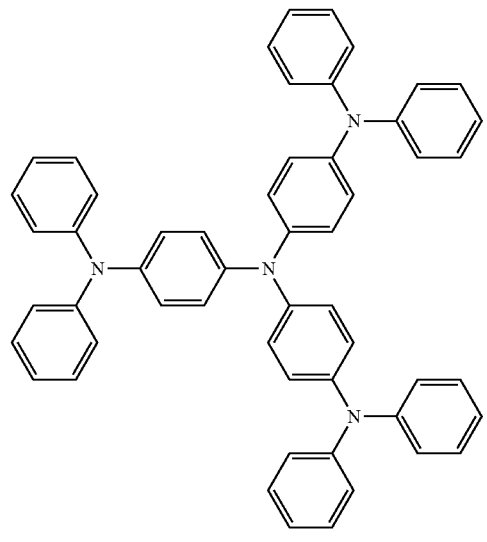

TDATA

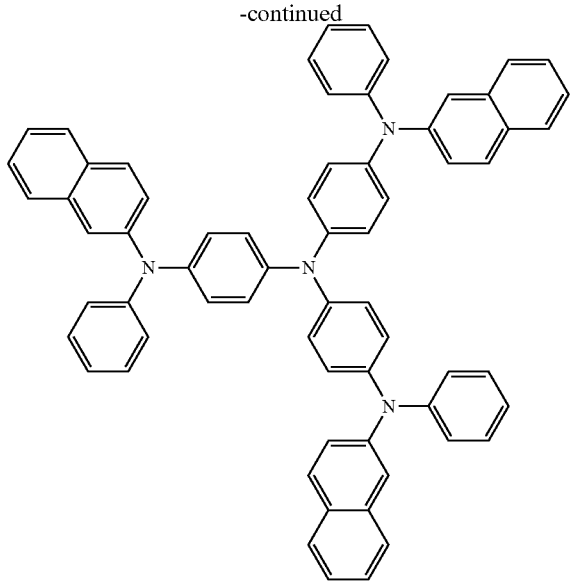

2-TNATA

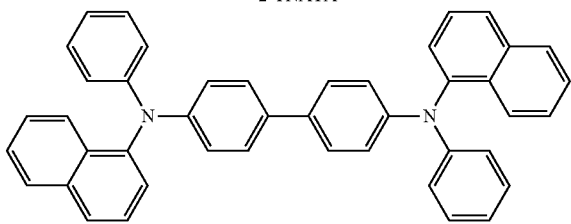

NPB

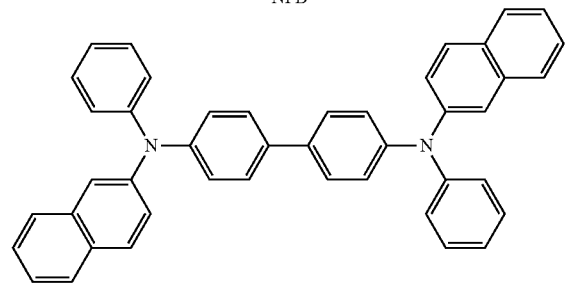

β-NPB

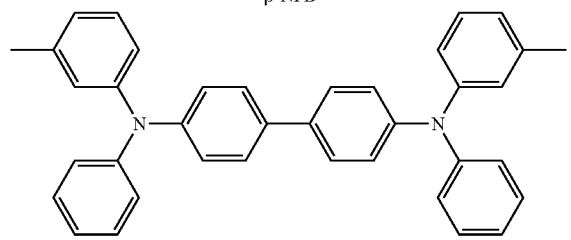

TPD

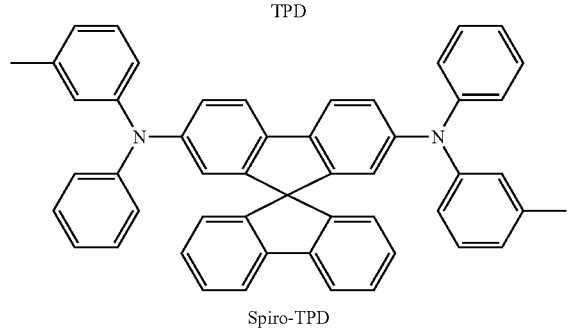

Spiro-TPD

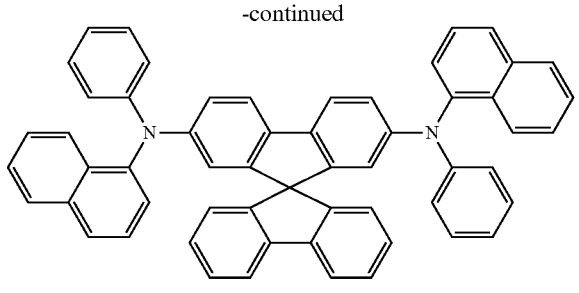

Spiro-NPB

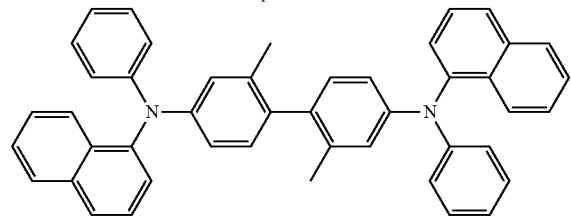

α-NPB

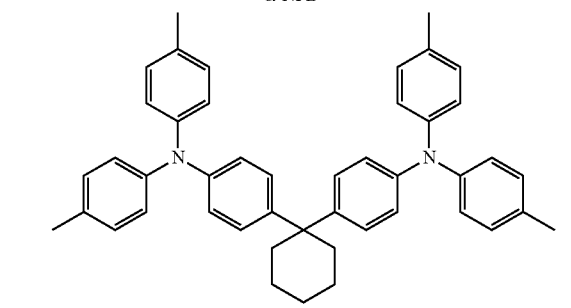

TAPC

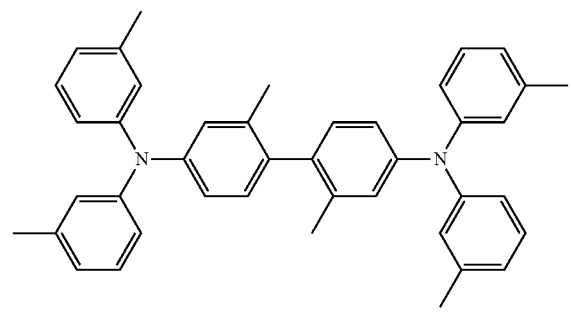

HMTPD

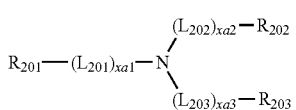

<Formula 201>

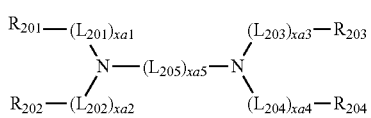

<Formula 202>

In Formulae 201 and 202, $L_{201}$ to $L_{205}$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, and a substituted or unsubstituted divalent non-aromatic condensed polycyclic group, at least one substituent of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$arylene group, the substituted $C_2$-$C_{60}$ heteroarylene group, and the substituted divalent non-aromatic condensed polycyclic group may be selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, —N($Q_{201}$)($Q_{202}$), —Si($Q_{203}$)($Q_{204}$)($Q_{205}$), and —B($Q_{206}$)($Q_{207}$);

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, —N($Q_{211}$)($Q_{212}$), —Si($Q_{213}$)($Q_{214}$)($Q_{215}$), and —B($Q_{216}$)($Q_{217}$); and —N($Q_{221}$)($Q_{222}$), —Si($Q_{223}$)($Q_{224}$)($Q_{225}$), and —B($Q_{226}$)($Q_{227}$), xa1 to xa4 may be each independently selected from 0, 1, 2, and 3, xa5 may be selected from 1, 2, 3, 4, and 5, $R_{201}$ to $R_{205}$ may be each independently selected from a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, —N($Q_{231}$)($Q_{232}$), —Si($Q_{233}$)($Q_{234}$)($Q_{235}$), and —B($Q_{236}$)($Q_{237}$);

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, —N($Q_{241}$)($Q_{242}$), —Si($Q_{243}$)($Q_{244}$)($Q_{245}$), and —B($Q_{246}$)($Q_{247}$), and $Q_{201}$ to $Q_{207}$, $Q_{211}$ to $Q_{217}$, $Q_{221}$ to $Q_{227}$, $Q_{231}$ to $Q_{237}$, and $Q_{241}$ to $Q_{247}$ may be each independently selected from a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group.

In Formulae 201 and 202, $L_{201}$ to $L_{205}$ may be defined as described above herein in conjunction with $L_1$, and $R_{201}$ to $R_{205}$ may be defined as described above herein in conjunction with $R_{11}$.

For example, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2, xa5 may be 1, 2, or 3, $R_{201}$ to $R_{205}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

The compound of Formula 201 may be a compound represented by Formula 201A below:

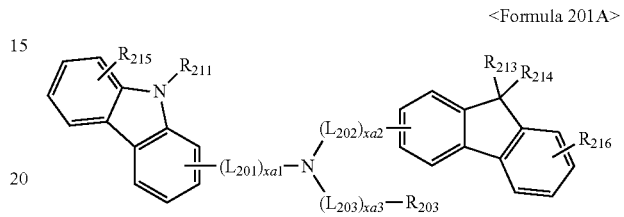

<Formula 201A>

For example, the compound of Formula 201 may be a compound represented by Formula 201A-1, but is not limited thereto:

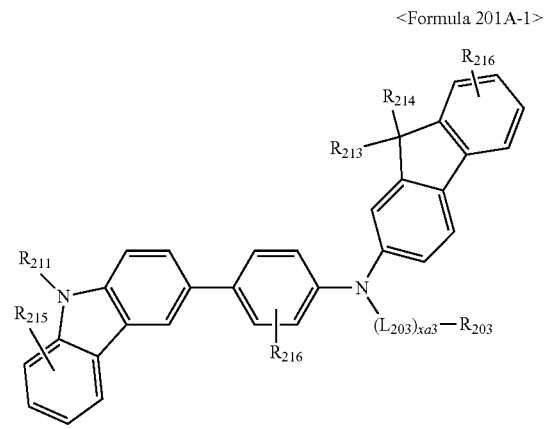

<Formula 201A-1>

The compound of Formula 202 may be a compound represented by Formula 202A, but is not limited thereto:

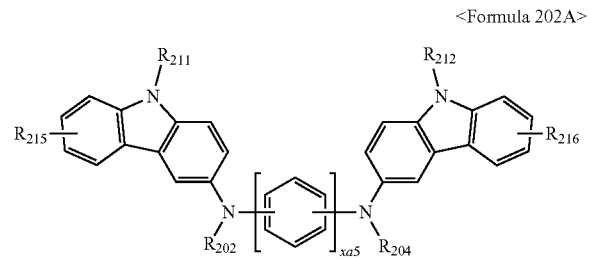

<Formula 202A>

In Formulae 201A, 201A-1, and 202A, $L_{201}$ to $L_{203}$, xa1 to xa3, xa5, and $R_{202}$ to $R_{204}$ may be the same as those described above herein, $R_{211}$ may be defined as described above herein in conjunction with $R_{203}$, $R_{213}$ to $R_{216}$ may be each independently selected from a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 may be each independently 0 or 1, $R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{213}$ and $R_{214}$ may be each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{215}$ and $R_{216}$ may be each independently selected from:

a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 may be 1 or 2.

In Formulae 201A and 201A-1, $R_{213}$ and $R_{214}$ may be linked to each other to form a saturated or unsaturated ring.

The compound of Formula 201 and the compound of Formula 202 may each independently be selected from Compounds Compound HT1 to HT20, but are not limited thereto.

HT1

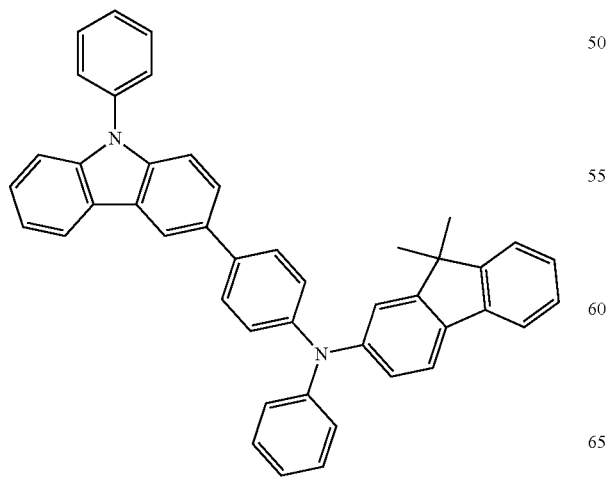

HT2

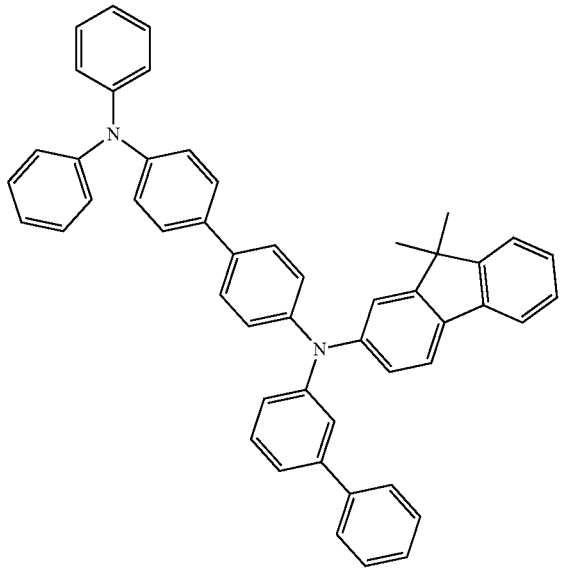

HT3

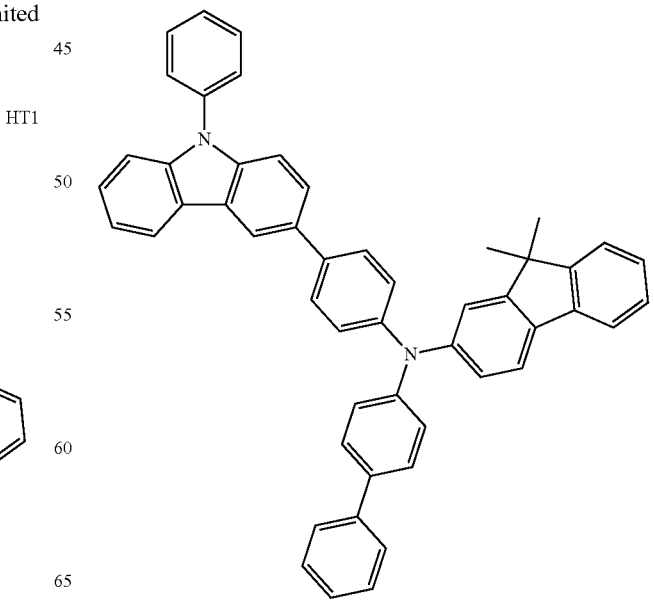

HT4
HT5
HT6
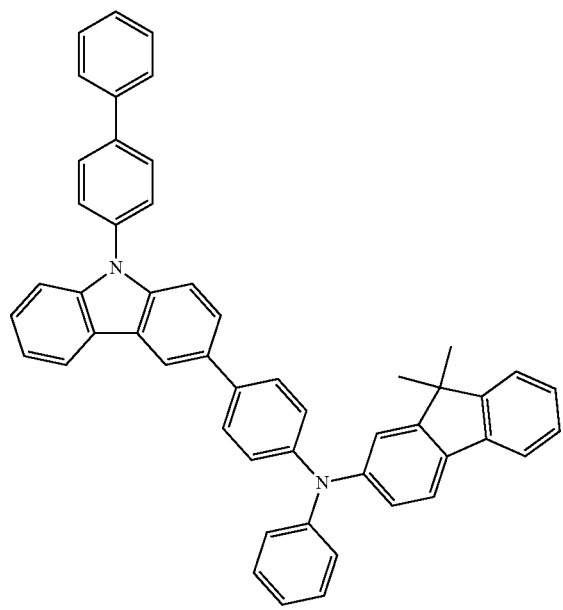
HT7
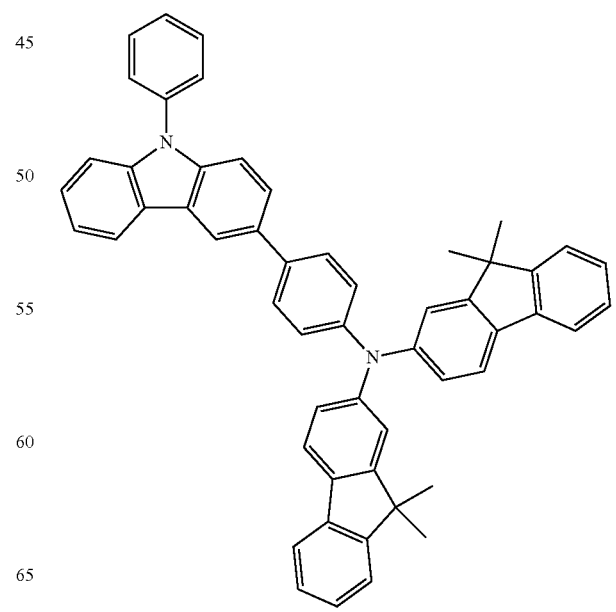

HT8
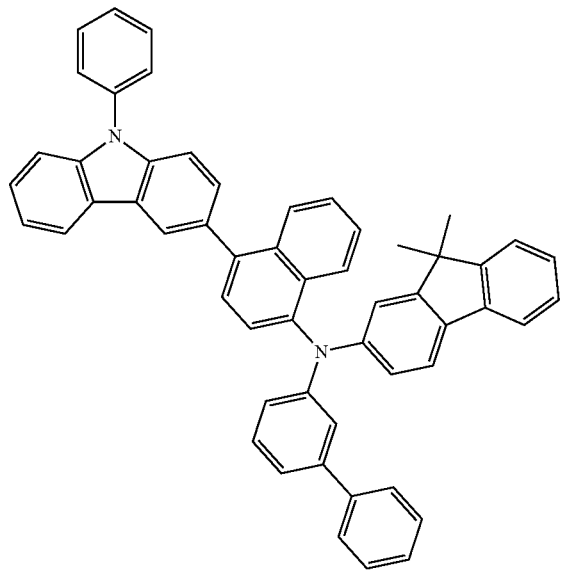
HT10
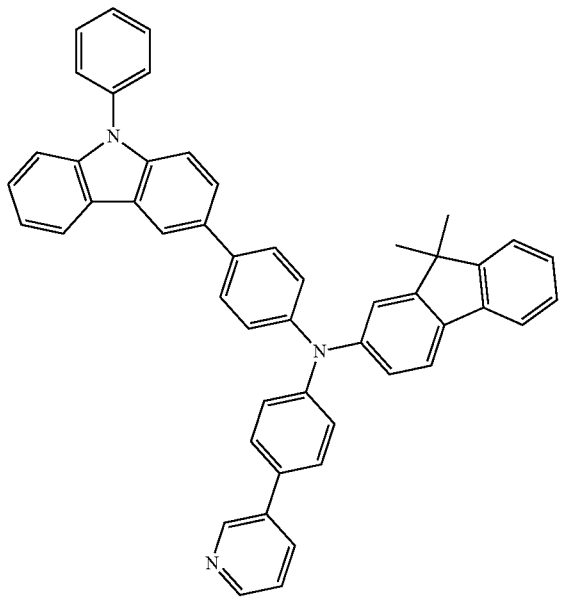
HT9
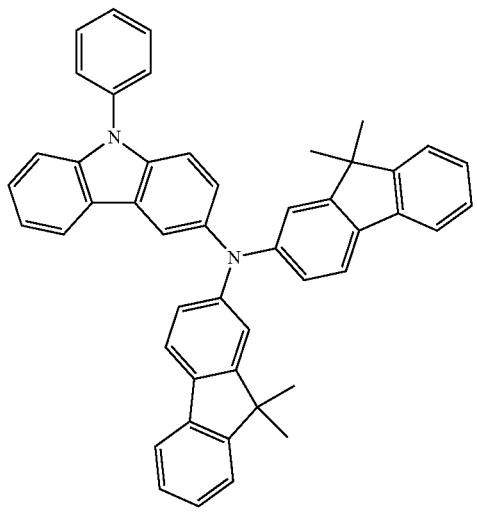
HT11
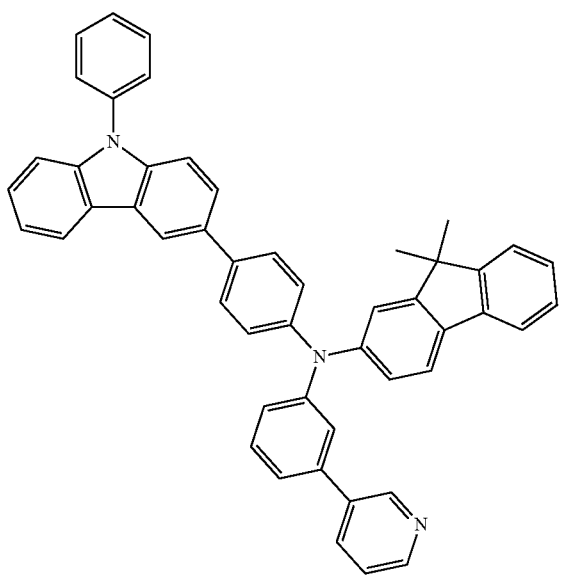

-continued
HT12
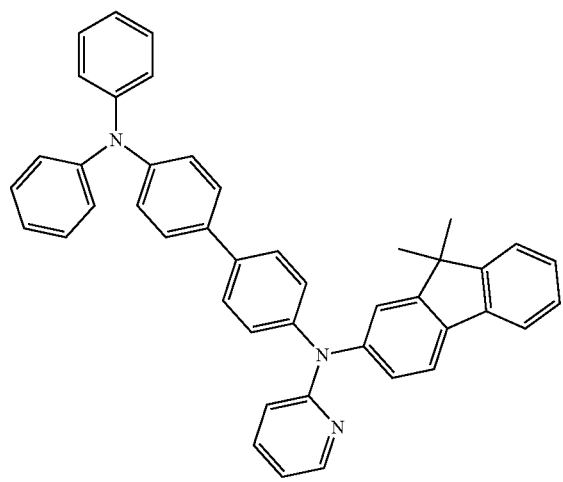
HT13
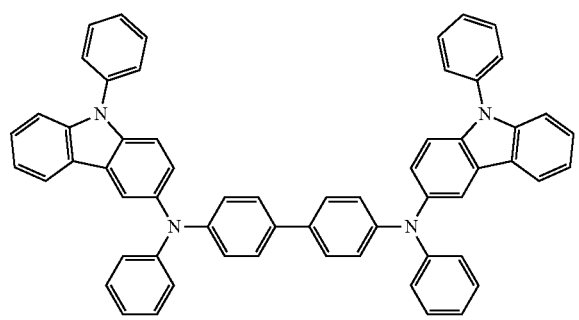
HT14
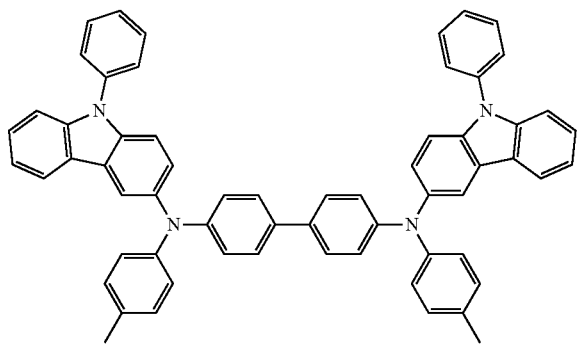
HT15
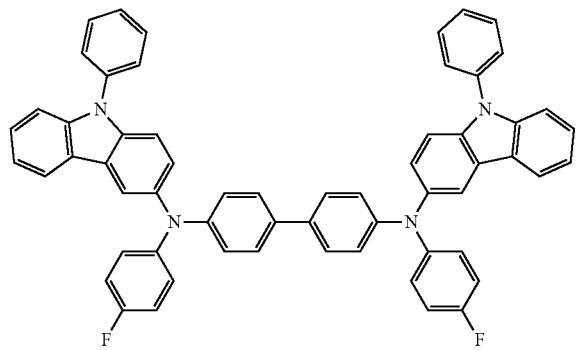
-continued
HT16
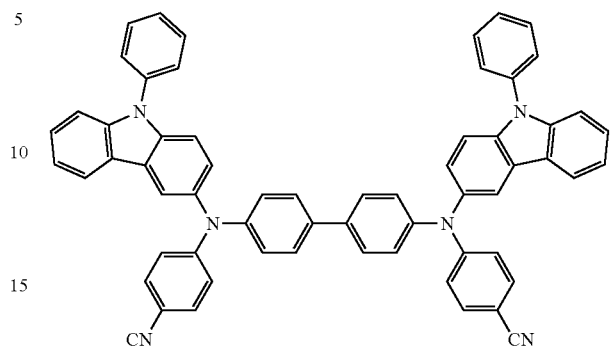
HT17
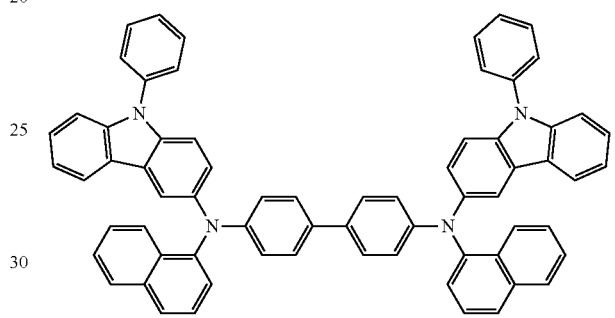
HT18
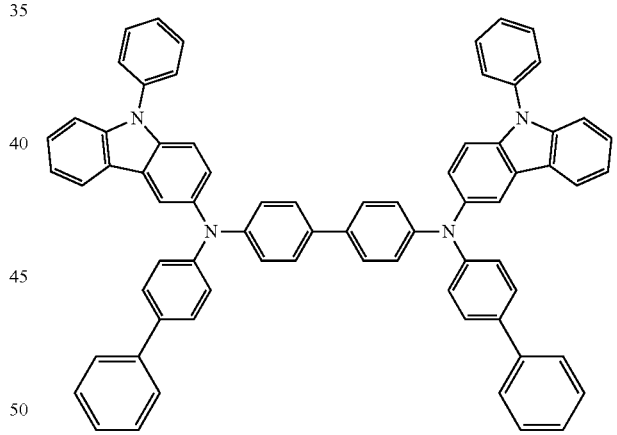
HT19
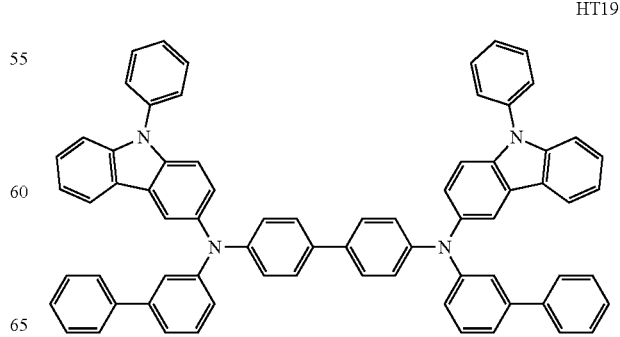

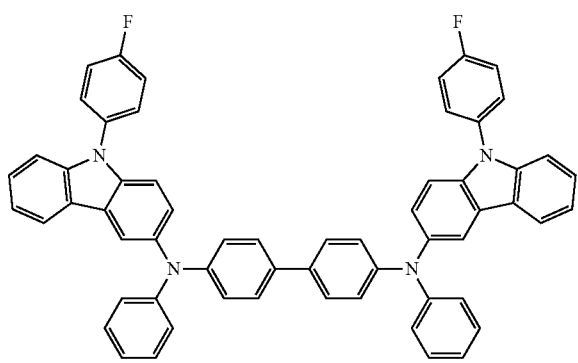

HT20

A thickness of the hole transport region may be from about 100 Å to about 10000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to help improve conductivity, in addition to the materials as described above. The charge-generating material may be homogeneously or inhomogeneously dispersed in the hole transport region.

The charge-generating material may be, e.g., a p-dopant. The p-dopant may be one of quinine derivatives, metal oxides, and cyano group-containing compounds, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and a Compound HT-D1 below.

<Compound HT-D1>

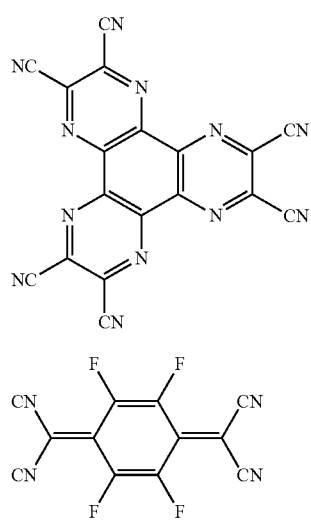

<F4-TCNQ>

The hole transport region may further include at least one of a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be any material used in the hole transport region. The EBL may block migration of electrons from the electron transport region into EML.

The EML may be formed on the first electrode 110 or the hole transport region by using any of a variety of methods, e.g., by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be described in detail When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material without separation of layers for the different color emission, and thus may emit white light. In some embodiments, the EML may be a white EML. In this regard, the EML may further include a color converting layer or a color filter to convert white light into light of a desired color.

The EML may include a host and a dopant.

For example, the host may include at least one of TPBi, TBADN, ADN, CBP, CDBP, and TCP.

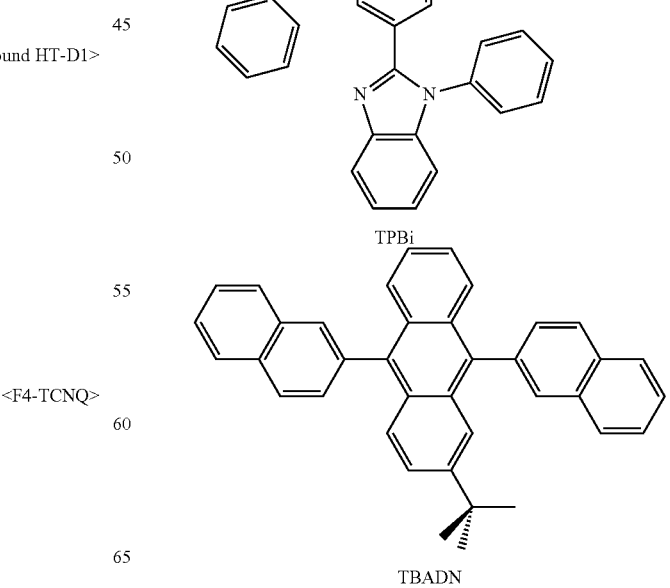

TPBi

TBADN

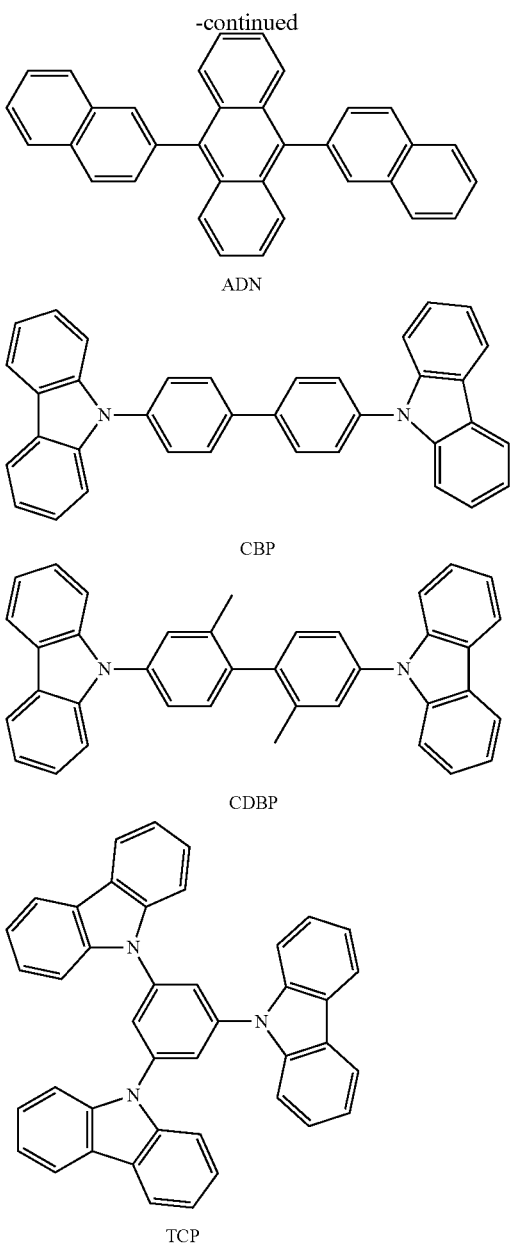

ADN

CBP

CDBP

TCP

In some embodiments, the host may include a compound represented by Formula 301.

$$Ar_{301}\text{-}[(L_{301})_{xb1}\text{-}R_{301}]_{xb2}$$ <Formula 301>

In Formula 301, $Ar_{301}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, and —Si($Q_{301}$)($Q_{302}$)($Q_{303}$) (where $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), $L_{301}$ may be defined as described above herein in conjunction with $L_{201}$, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 is selected from 0, 1, 2, and 3;

xb2 is selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group. However, embodiments are not limited thereto.

The compound of Formula 301 may include at least one of Compounds H1 to H42. However, embodiments are not limited thereto:

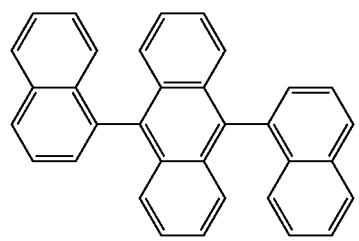

H1

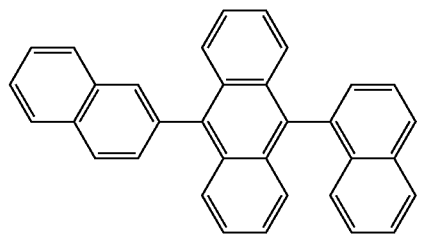

H2

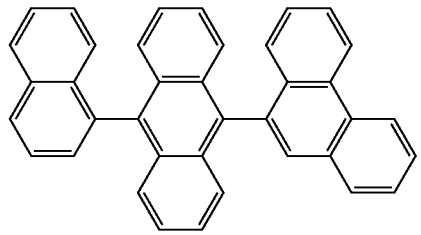

H3

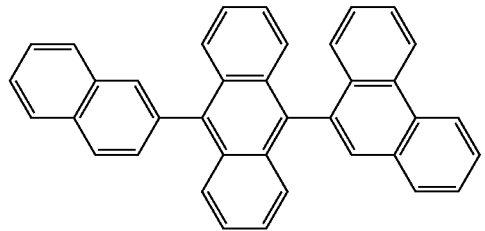

H4

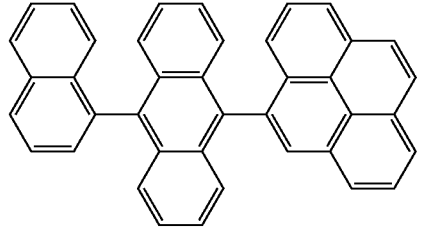

H5

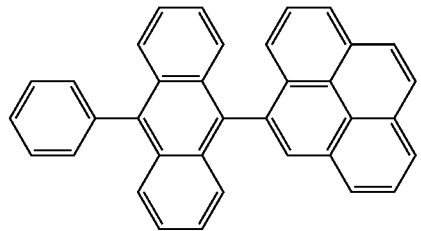

H6

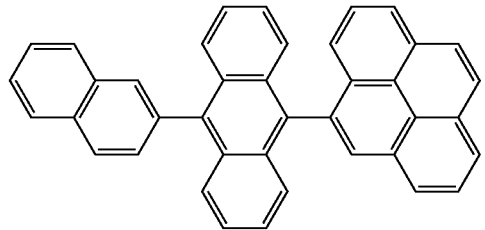

H7

H8
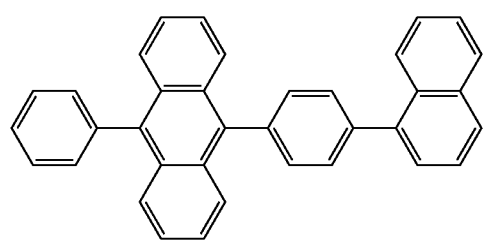
H9
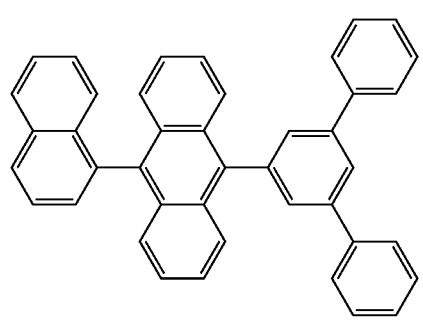
H10
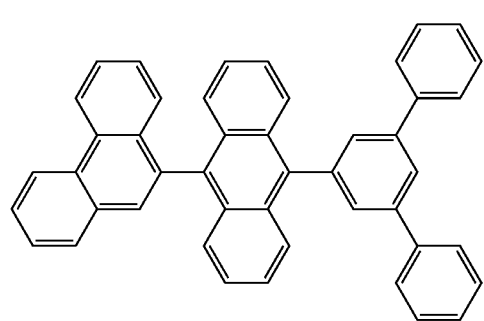
H11
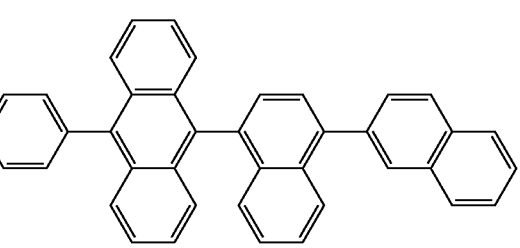
H12
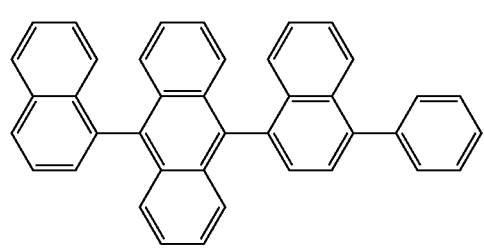
H13
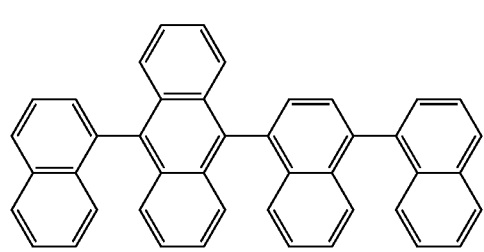
H14
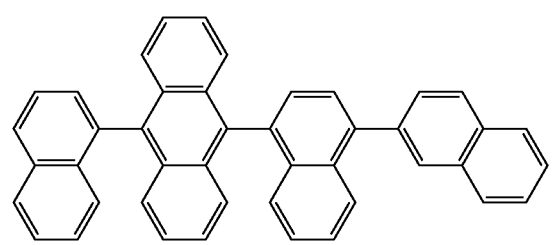
H15
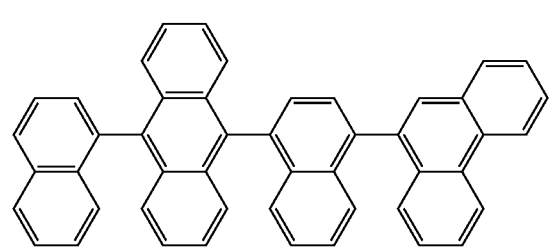
H16
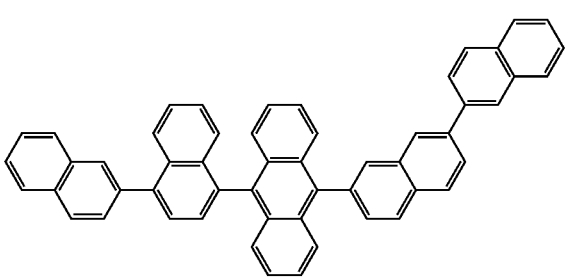
H17
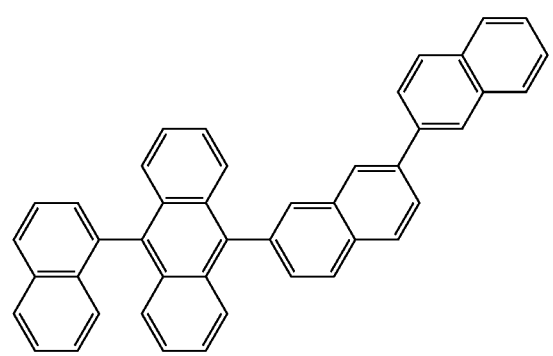
H18
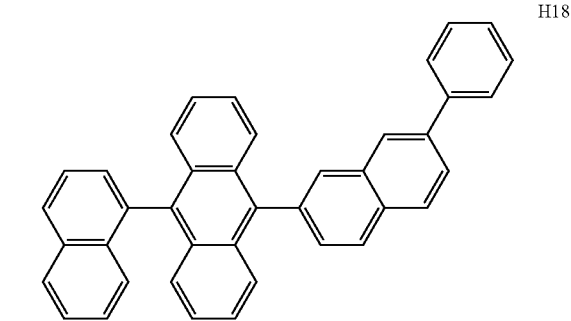

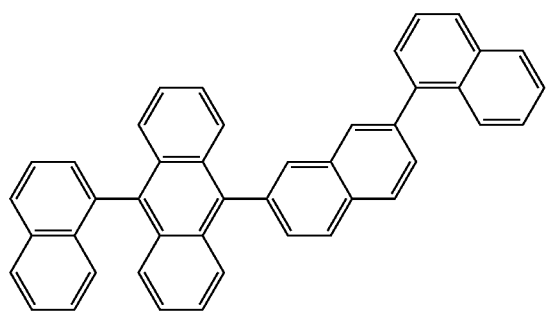
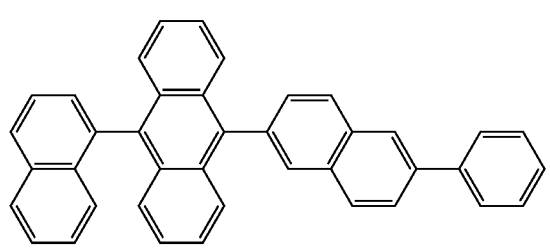
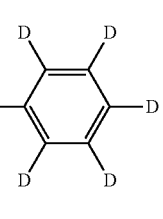

H29
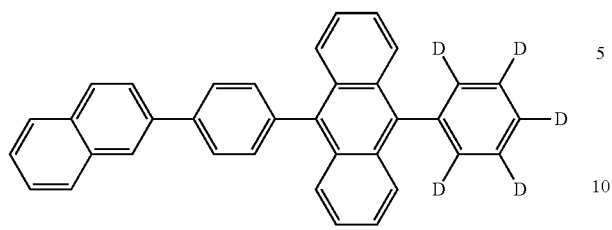
H30
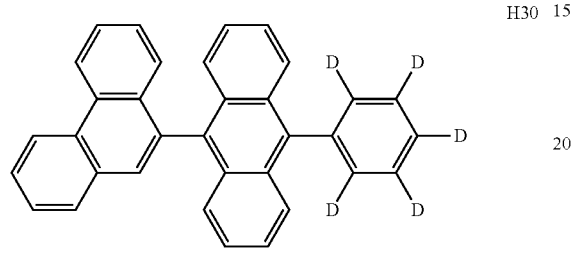
H31
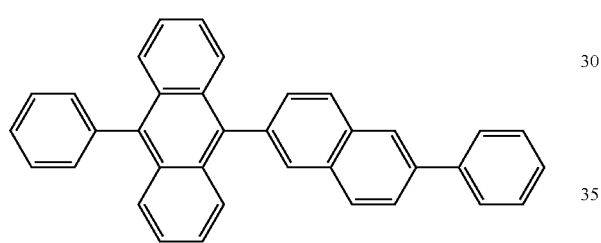
H32
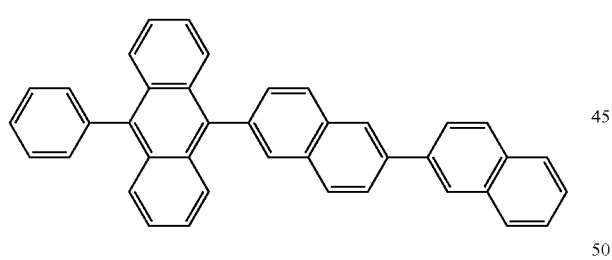
H33
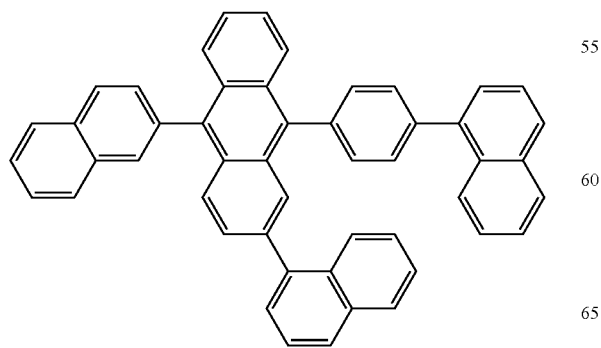
H34
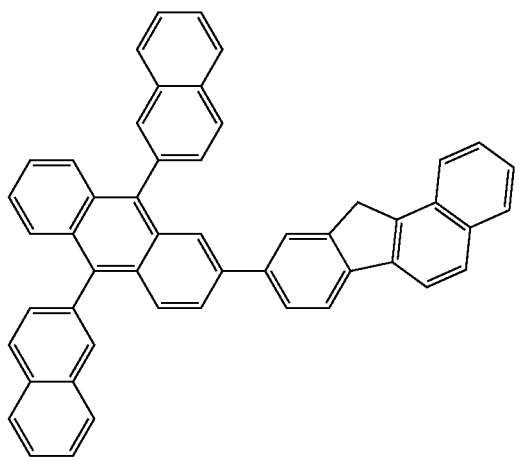
H35
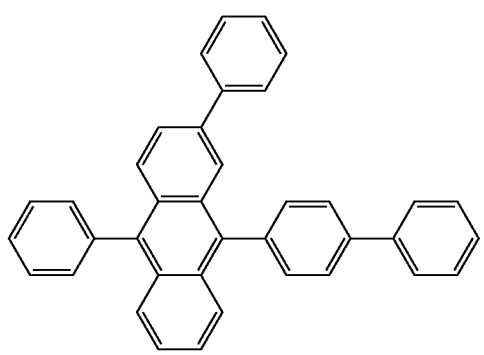
H36
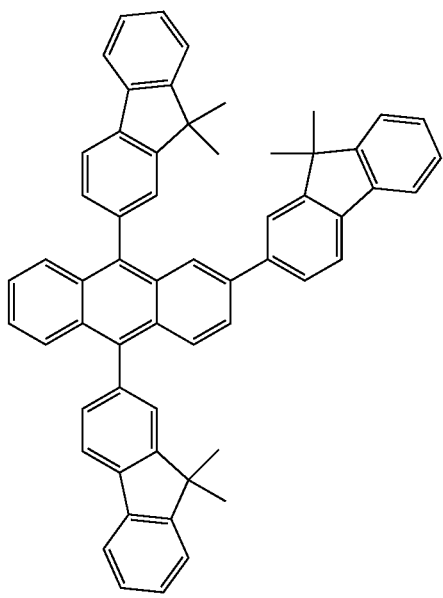

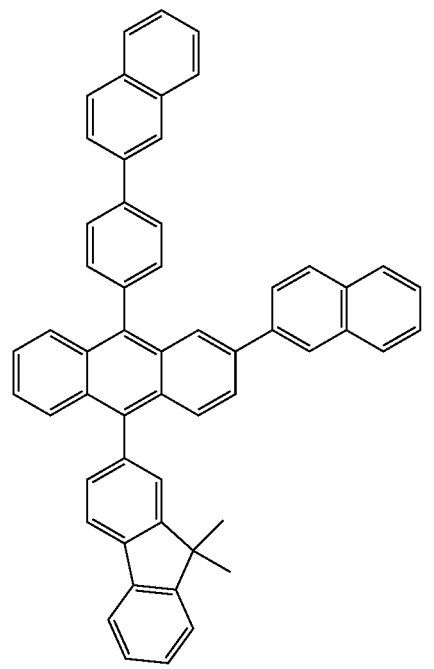
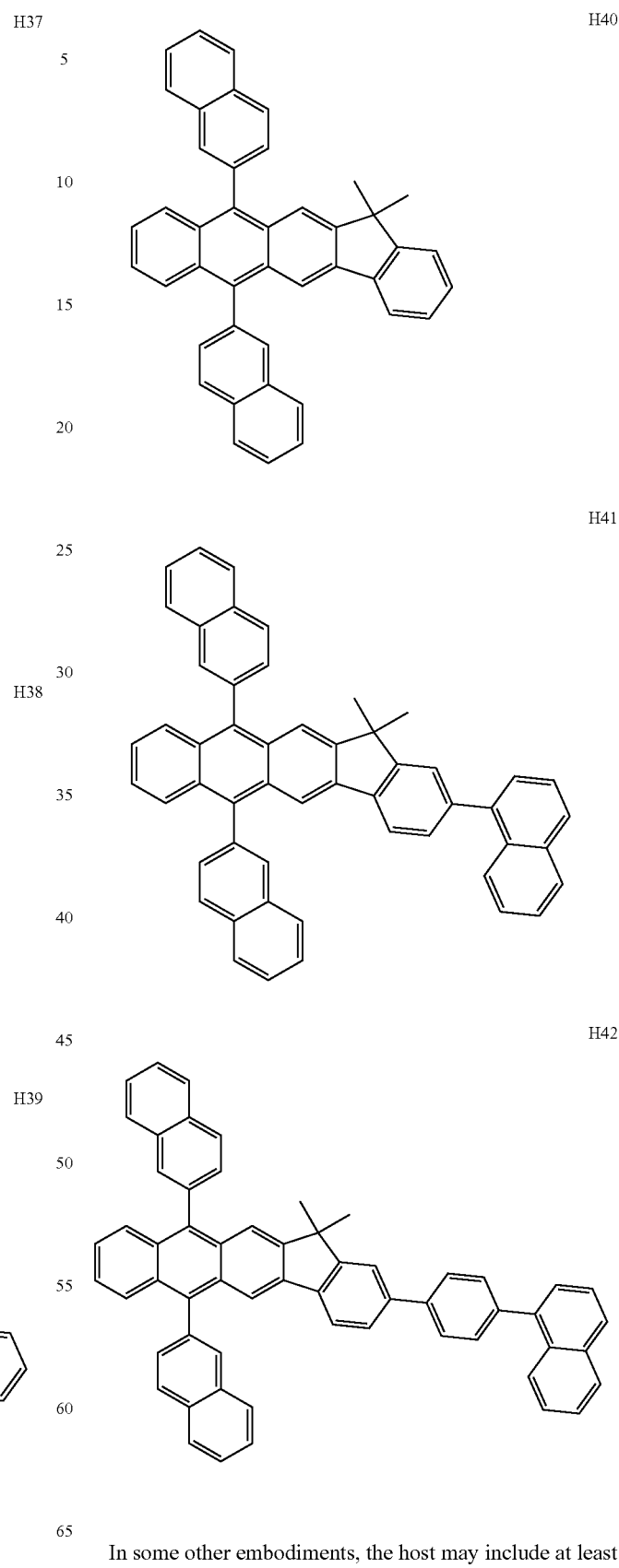
In some other embodiments, the host may include at least one of Compounds H43 to H49, but are not limited thereto:

H43 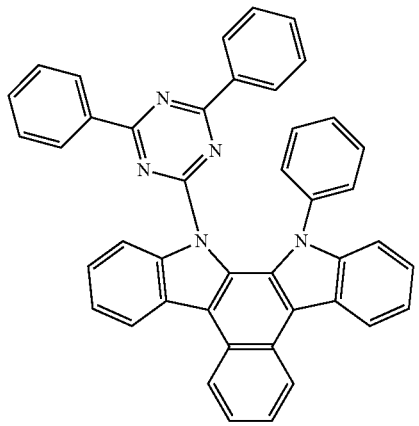
H44 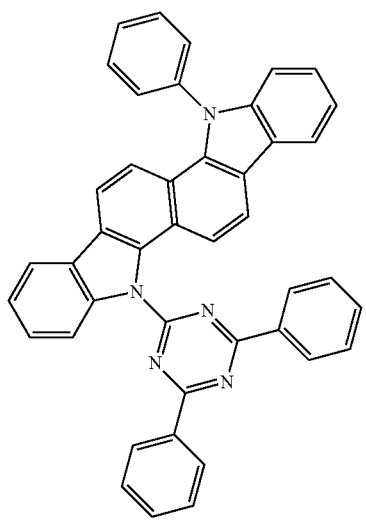
H45 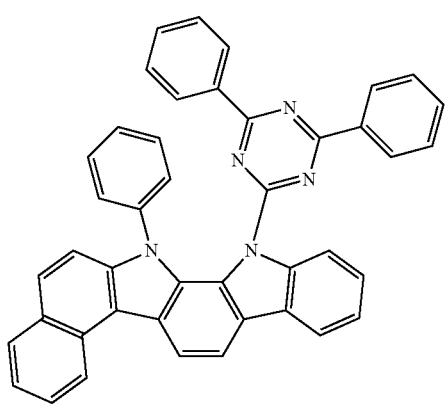
H46 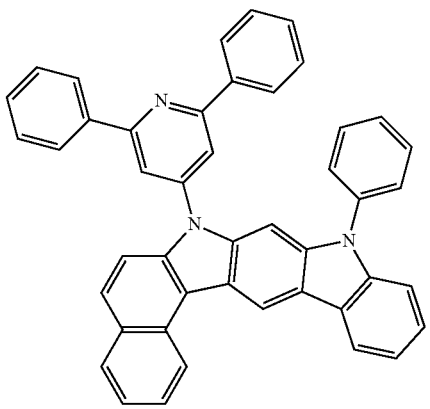
H47 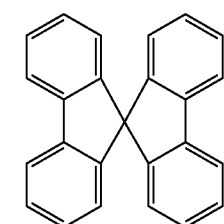
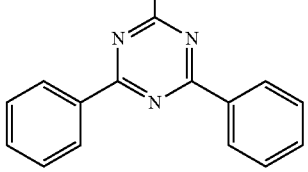
H48 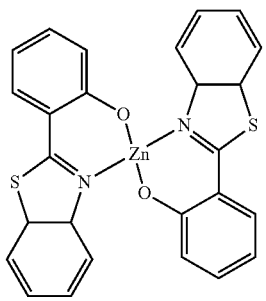
H49 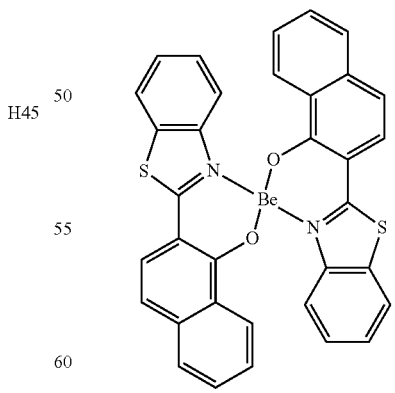
The dopant may include at least one of a fluorescent dopant and a phosphorescent dopant.
The phosphorescent dopant may include an organic metal complex represented by Formula 401 below:

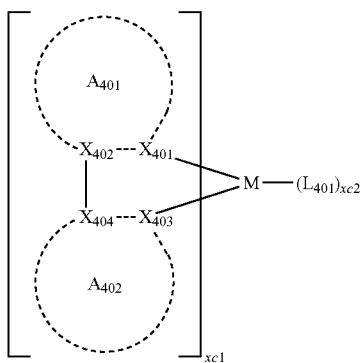

<Formula 401>

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may be each independently a nitrogen atom or a carbon atom, $A_{401}$ and $A_{402}$ ring may be each independently selected from a substituted or unsubstituted benzene group, a substituted or unsubstituted naphthalene group, a substituted or unsubstituted fluorene group, a substituted or unsubstituted spiro-fluorene group, a substituted or unsubstituted indene group, a substituted or unsubstituted pyrrole group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted or unsubstituted isooxazole group, a substituted or unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazole group, a substituted or unsubstituted benzoimidazole group, a substituted or unsubstituted benzofuran group, a substituted or unsubstituted benzothiophene group, a substituted or unsubstituted isobenzothiophene group, a substituted or unsubstituted benzoxazole group, a substituted or unsubstituted isobenzoxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group, at least one substituent of the substituted benzene group, the substituted naphthalene group, the substituted fluorene group, the substituted spiro-fluorene group, the substituted indene group, the substituted pyrrole group, the substituted thiophene group, the substituted furan group, the substituted imidazole group, the substituted pyrazole group, the substituted thiazole group, the substituted isothiazole group, the substituted oxazole group, the substituted isooxazole group, the substituted pyridine group, the substituted pyrazine group, the substituted pyrimidine group, the substituted pyridazine group, the substituted quinoline group, the substituted isoquinoline group, the substituted benzoquinoline group, the substituted quinoxaline group, the substituted quinazoline group, the substituted carbazole group, the substituted benzoimidazole group, the substituted benzofuran group, the substituted benzothiophene group, the substituted isobenzothiophene group, the substituted benzoxazole group, the substituted isobenzoxazole group, the substituted triazole group, the substituted oxadiazole group, the substituted triazine group, the substituted dibenzofuran group, and the substituted dibenzothiophene group may be selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, —$N(Q_{401})(Q_{402})$, —$Si(Q_{403})(Q_{404})(Q_{405})$, and —$B(Q_{406})(Q_{407})$;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, —$N(Q_{411})(Q_{412})$, —$Si(Q_{413})(Q_{414})(Q_{415})$, and —$B(Q_{416})(Q_{417})$; and —$N(Q_{421})(Q_{422})$, —$Si(Q_{423})(Q_{424})(Q_{425})$, and —$B(Q_{426})(Q_{427})$, $L_{401}$ may be an organic ligand, xc1 may be 1, 2, or 3, and xc2 may be 0, 1, 2, or 3.

For example, $L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazole carboxylate, or benzoate), a carbon monoxide ligand, an isonitrile ligand, a cyano ligand, and a phosphorous ligand (for example, phosphine or phosphaite), but is not limited thereto When $A_{401}$ in Formula 401 has at least two substituents, the at least two substituents of $A_{401}$ may be linked to each other to form a saturated or unsaturated ring.

When $A_{402}$ in Formula 401 has at least two substituents, the at least two substituents of $A_{402}$ may be linked to each other to form a saturated or unsaturated ring.

When xc1 in Formula 401 is 2 or greater, the plurality of ligands in Formula 401, represented by

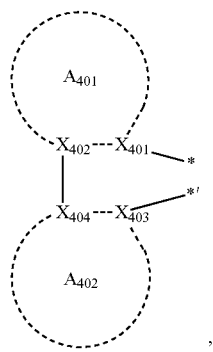

may be identical to or different from each other. When xc1 in Formula 401 is 2 or greater, $A_{401}$ and $A_{402}$ may be linked to $A_{401}$ and $A_{402}$ of another adjacent ligand directly or via a linker (for example, a $C_1$-$C_5$ alkylene group, —N(R')— (where R' is a $C_1$-$C_{10}$ alkyl group or a $C_6$-$C_{20}$ aryl group), or —C(=O)—).

The phosphorescent dopant may include at least one of Compounds PD1 to PD74, but is not limited thereto:

PD1

PD2

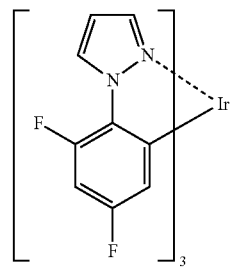

PD3

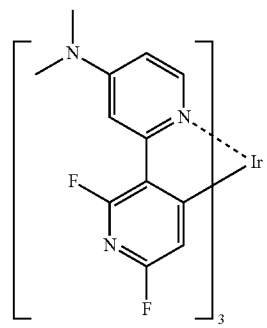

PD4

PD5

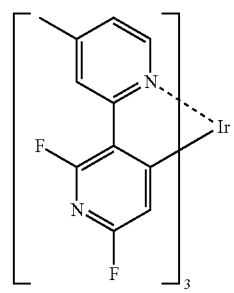

PD6

PD7

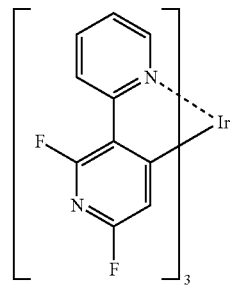

PD8

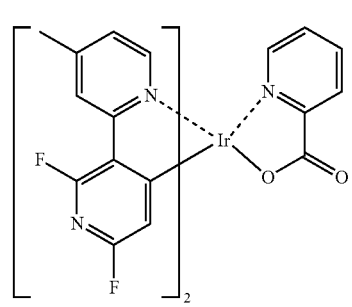

PD9 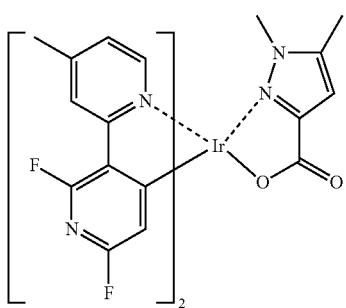
PD10 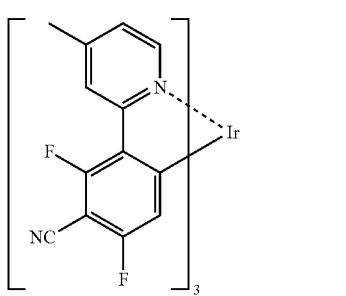
PD11 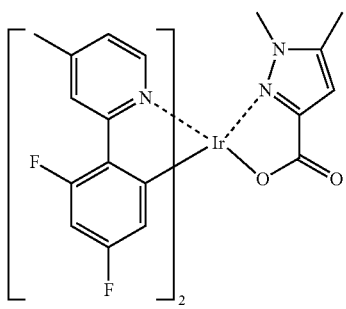
PD12 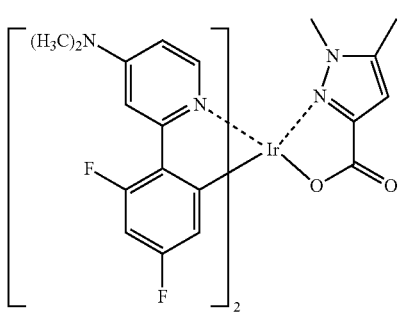
PD13 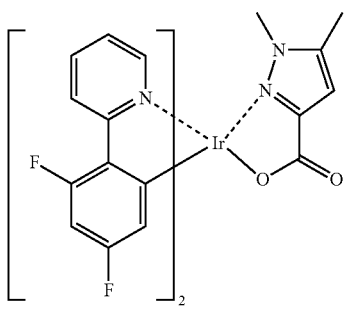
PD14 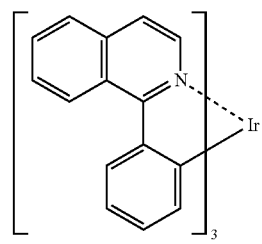
PD15 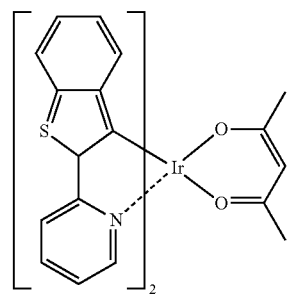
PD16 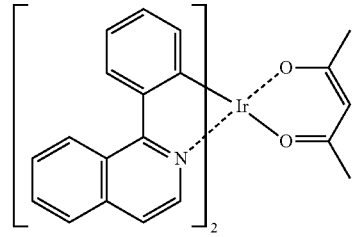
PD17 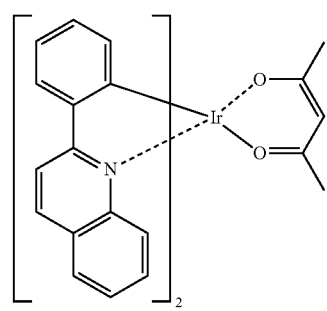
PD18 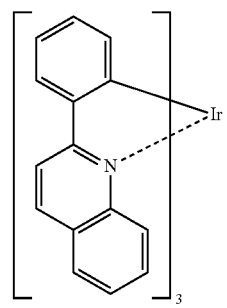

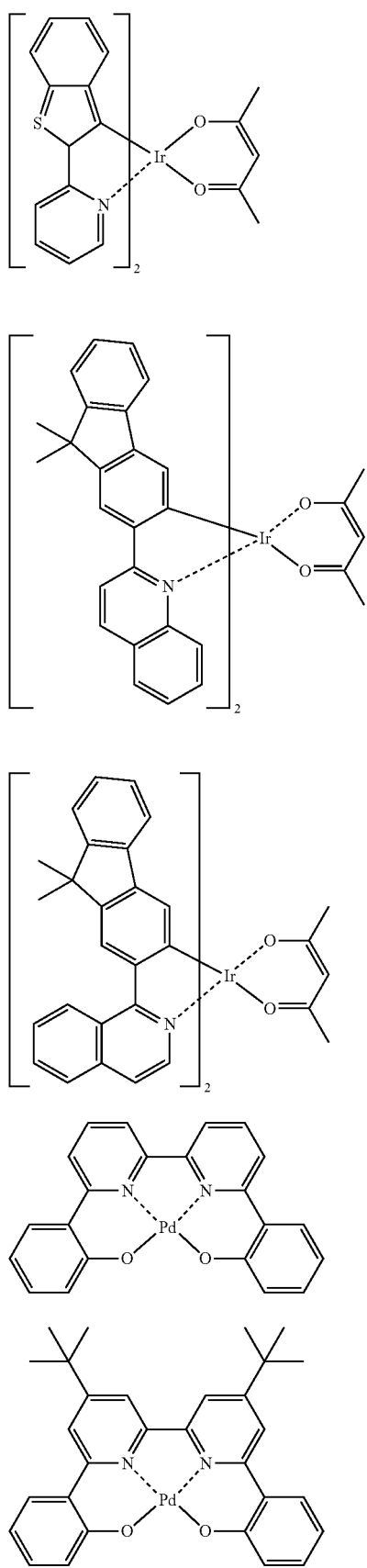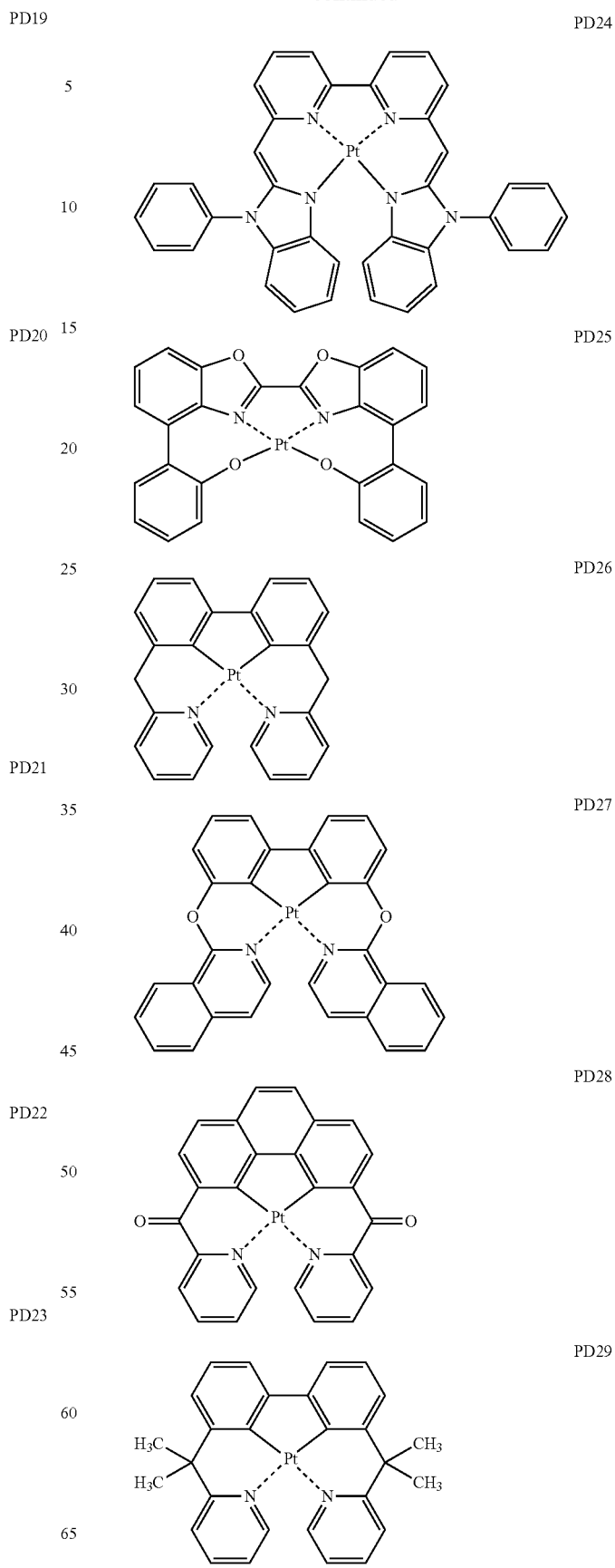

PD30 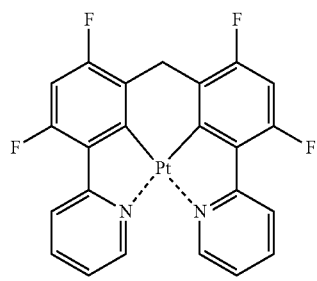
PD31 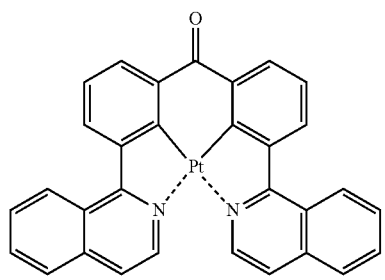
PD32 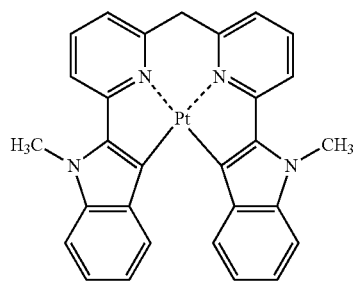
PD33 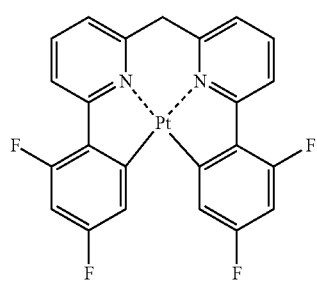
PD34 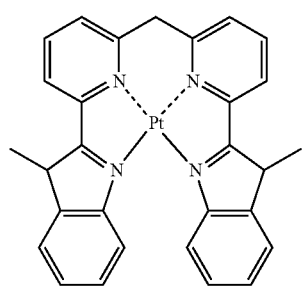
PD35 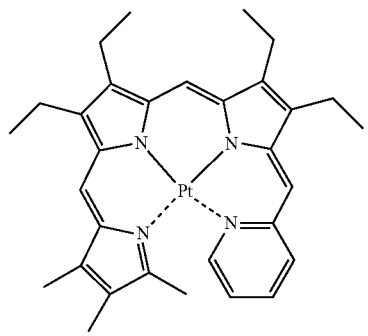
PD36 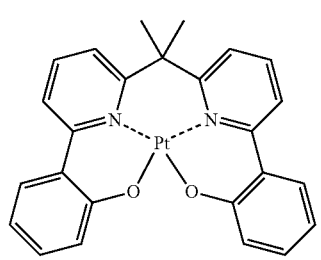
PD37 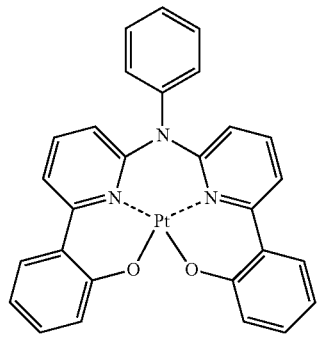
PD38 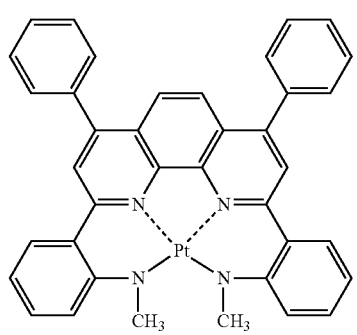
PD39 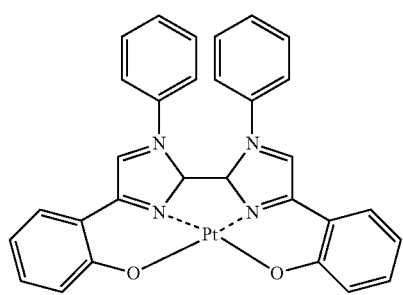

PD40
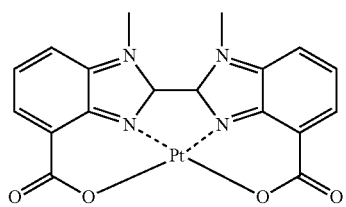
PD41
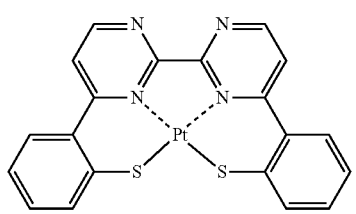
PD42
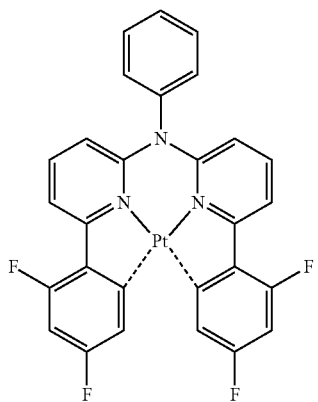
PD43
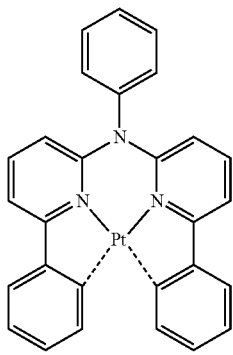
PD44
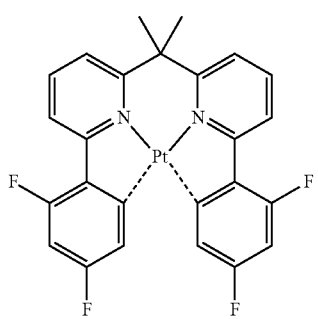
PD45
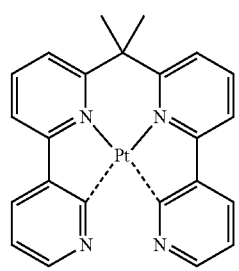
PD46
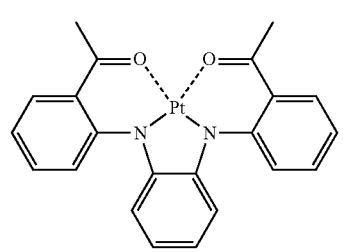
PD47
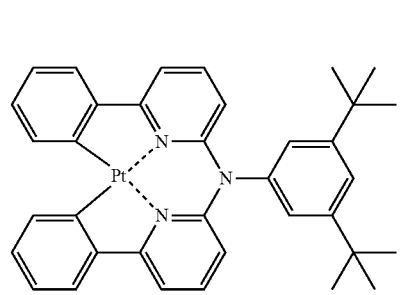
PD48
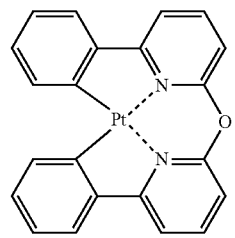
PD49
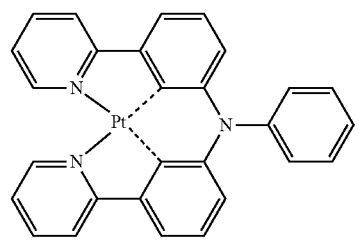
PD50
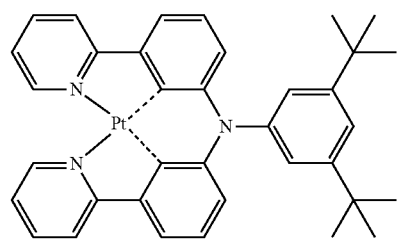

PD51 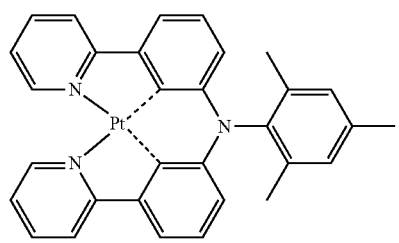
PD52 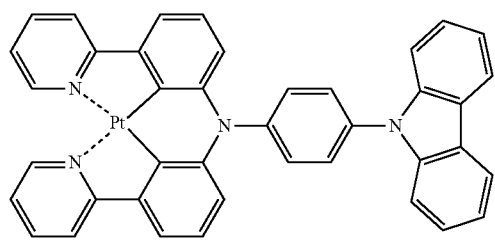
PD53 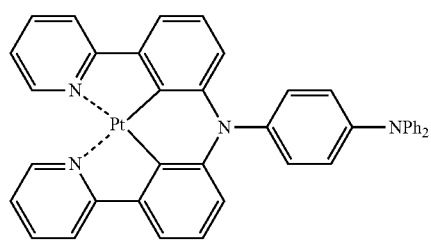
PD54 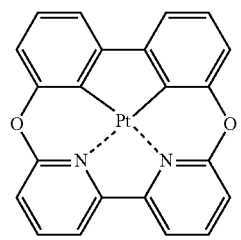
PD55 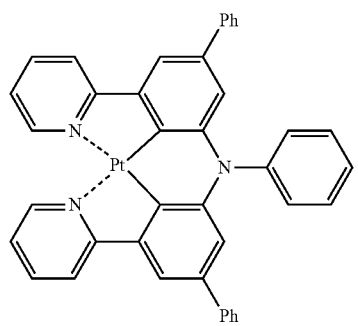
PD56 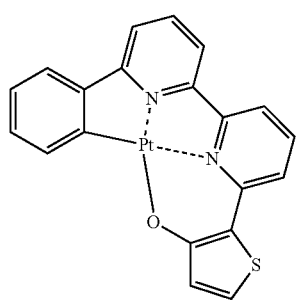
PD57 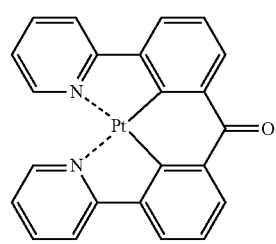
PD58 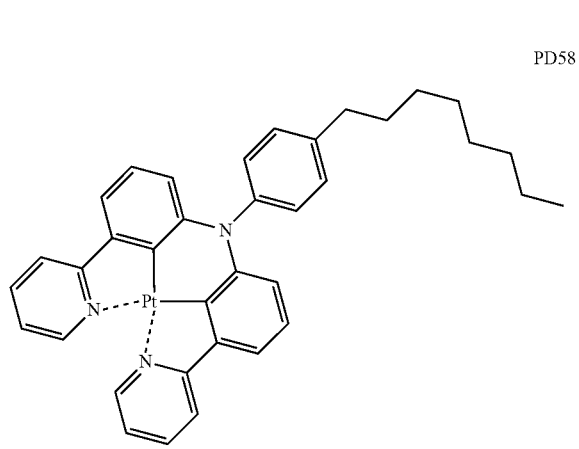
PD59 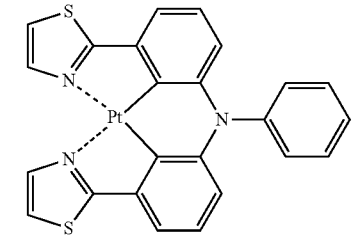
PD60 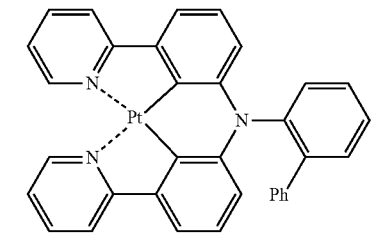
PD61 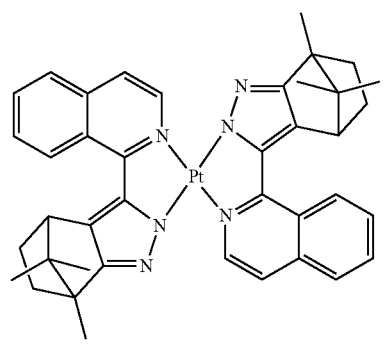

PD62 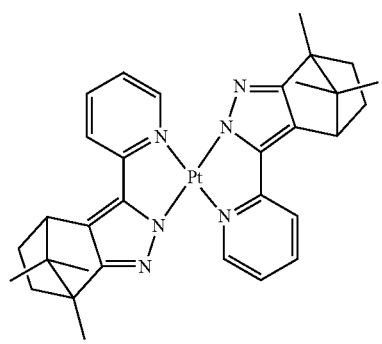
PD63 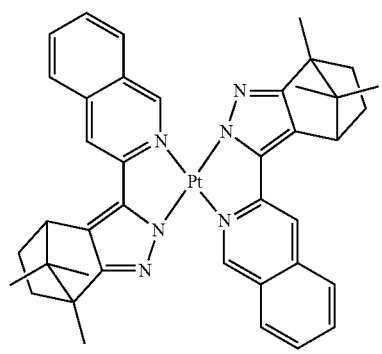
PD64 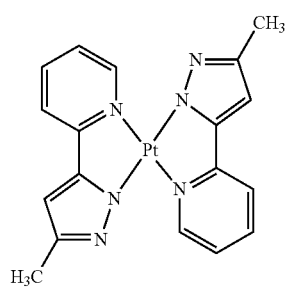
PD65 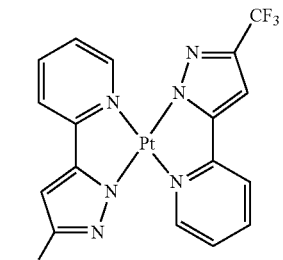
PD66 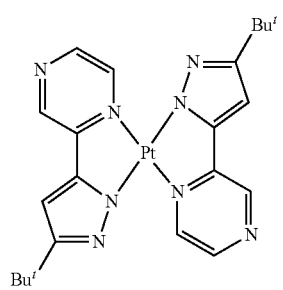
PD67 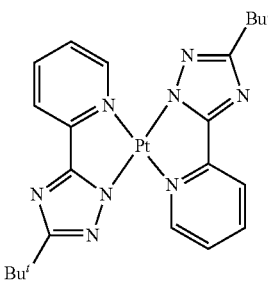
PD68 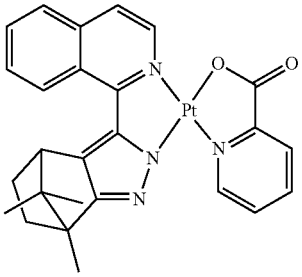
PD69 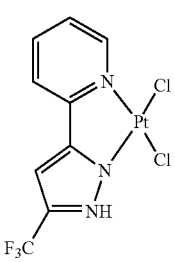
PD70 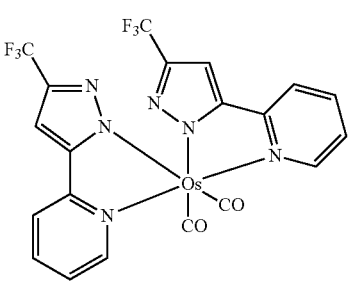
PD71 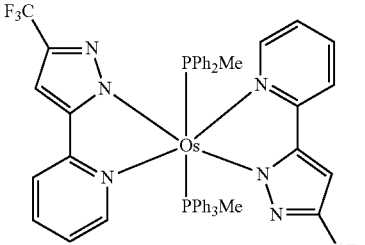
PD72 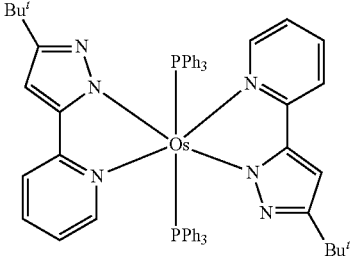

-continued
PD73 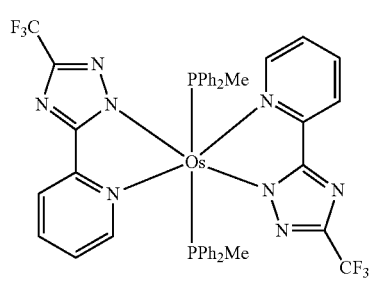
PD74 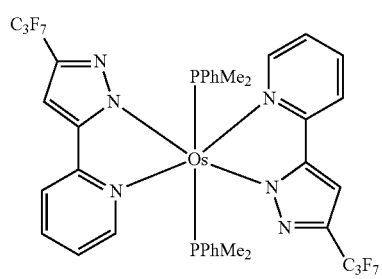
For example, the phosphorescent dopant may include PtOEP below:
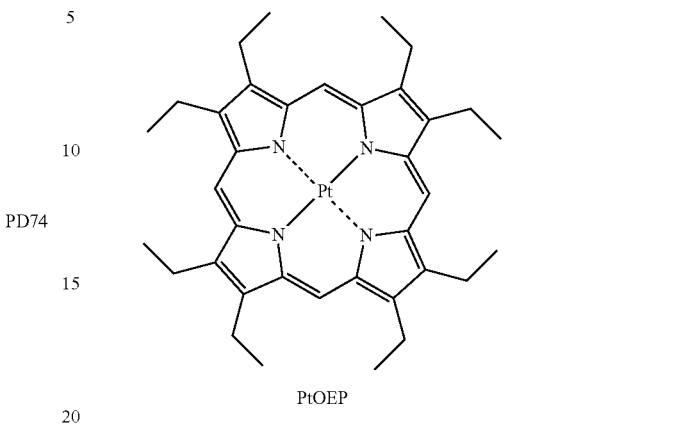
PtOEP
The fluorescent dopant may include at least one of DPAVBi, BDAVBi, TBPe, DCM, DCJTB, Coumarin 6, and C545T below.
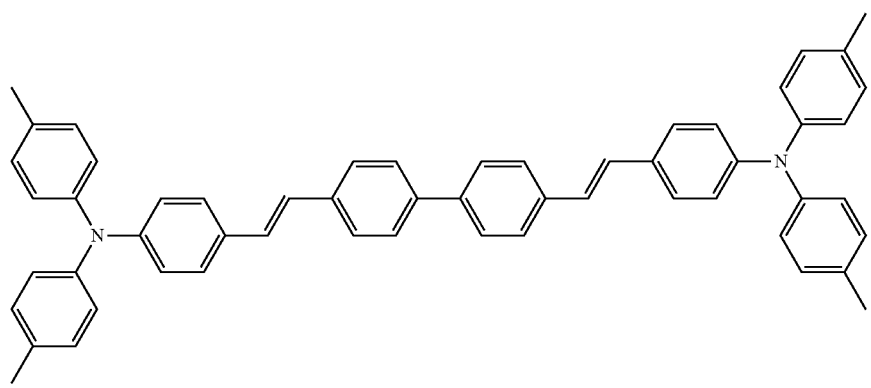
DPAVBi
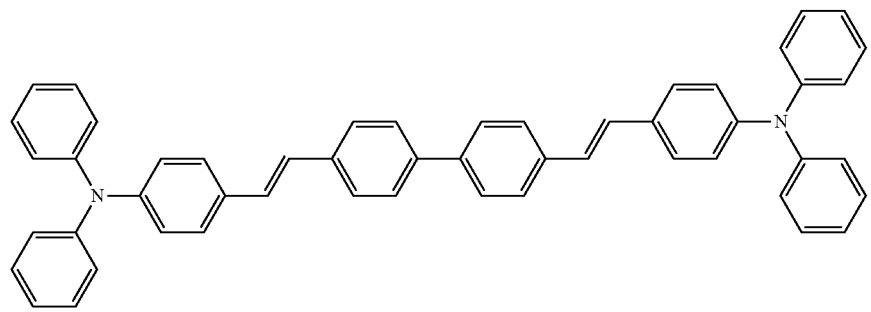
BDAVBi
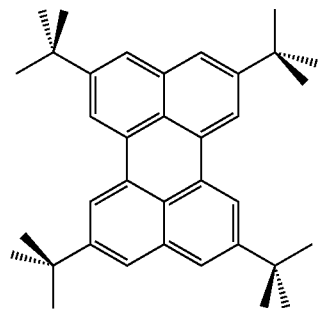
TBPe
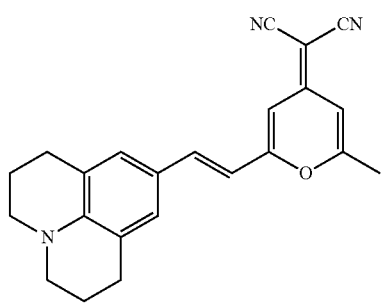
DCM

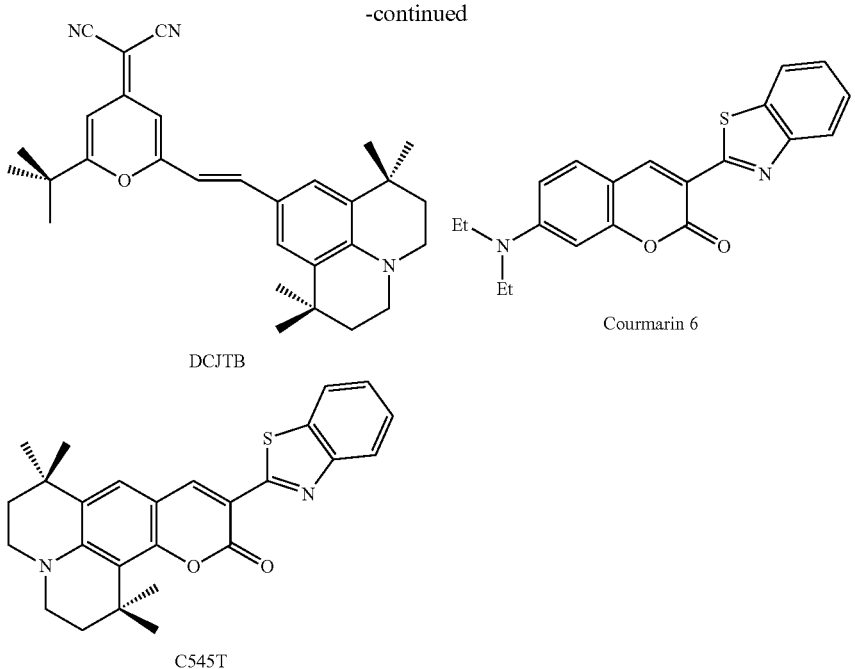

DCJTB

Courmarin 6

C545T

For example, the fluorescent dopant may include a compound represented by Formula 501 below:

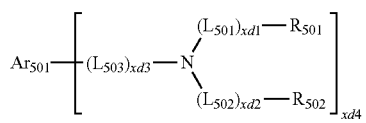

<Formula 501>

In Formula 501, $Ar_{501}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a non-aromatic condensed polycyclic group, and —Si($Q_{501}$)($Q_{502}$)($Q_{503}$) (where $Q_{501}$ to $Q_{503}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{501}$ to $L_{503}$ may be defined as described above herein in conjunction with $L_{201}$;

$R_{501}$ and $R_{502}$ may be each independently selected from:
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 are each independently selected from 0, 1, 2, and 3, and xb4 is selected from 1, 2, 3, and 4.

For example, the fluorescent host may include at least one of Compounds FD1 to FD8:

FD1
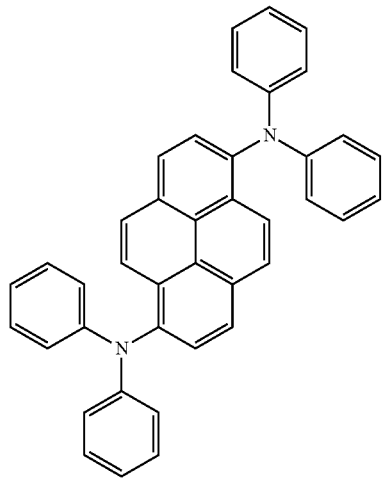
FD2
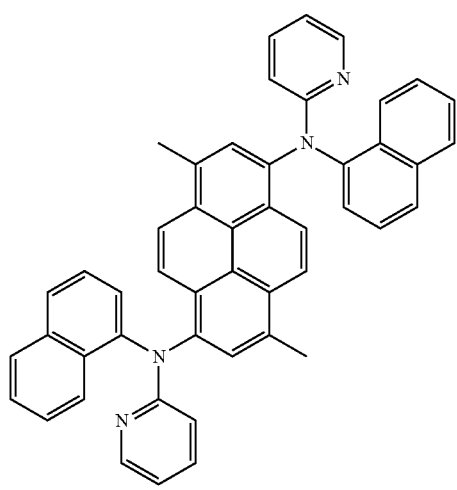
FD3
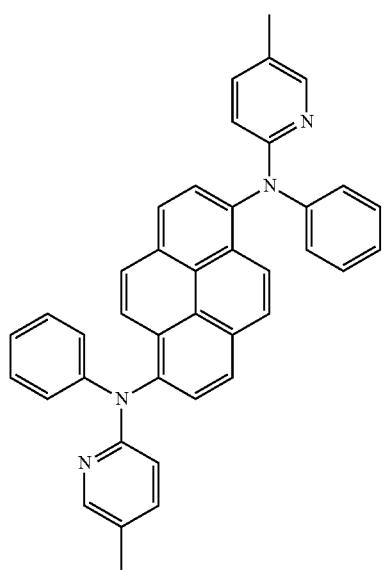
FD4
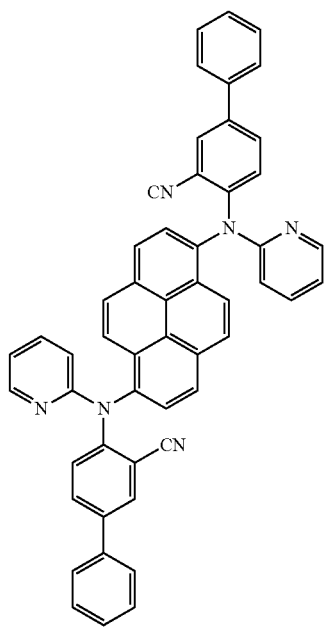
FD5
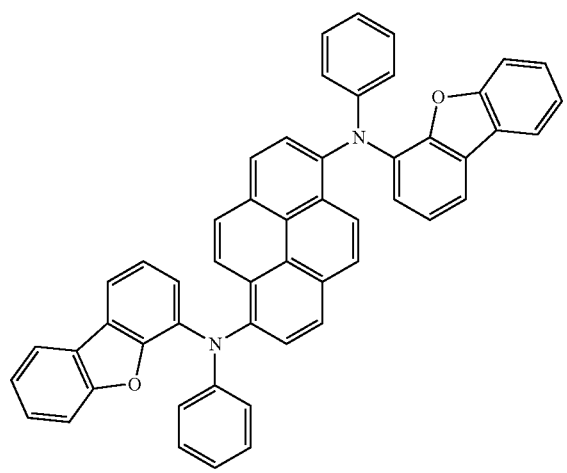
FD6
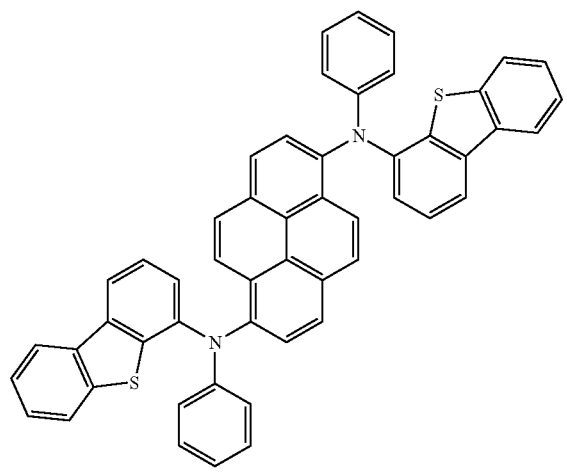

-continued

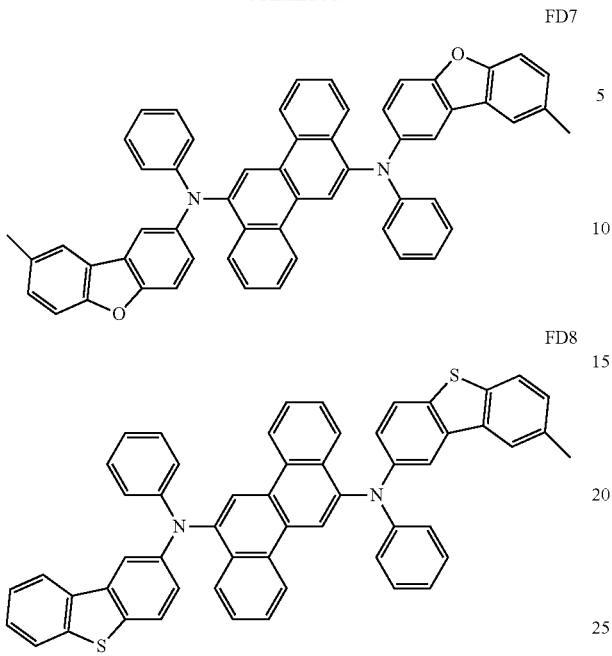

FD7

FD8

An amount of the dopant in the EML may be from about 0.01 parts to about 15 parts by weight based on 100 parts by weight of the host, but is not limited to this range.

A thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Next, the electron transport region may be formed on the EML.

The electron transport region may include at least one of a HBL, an ETL, and an EIL. However, embodiments are not limited thereto.

In some embodiments, the electron transport region may have a structure including an ETL/EIL or a HBL/ETL/EIL, wherein the layers forming a structure of the electron transport region may be sequentially stacked on the EML in the order stated above. However, embodiments are not limited thereto:

In some embodiments, the organic layer 150 of the organic light-emitting device 10 may include an electron transport region between the EML and the second electrode 190, and the electron transport region may include the chrysene-based compound of Formula 1.

The electron transport region may include a HBL. When the EML includes a phosphorescent dopant, the HBL may prevent diffusion of triplet exitons or holes into the ETL from the EML.

When the electron transport region includes a HBL, the HBL may be formed on the EML by using any of a variety of methods, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be described in detail.

For example, the HBL may include at least one of BCP below and Bphen below. However, embodiments are not limited thereto.

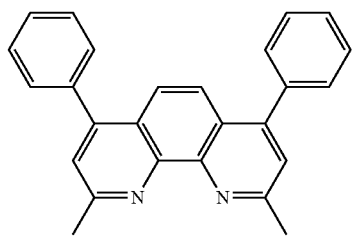

BCP

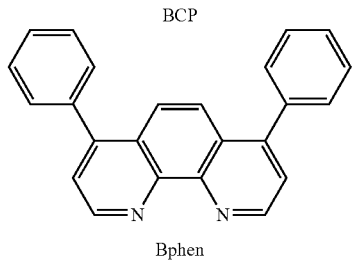

Bphen

A thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL, and accordingly will not be described in detail.

In some embodiments, the organic layer 150 of the organic light-emitting device 10 may include an electron transport region between the EML and the second electrode 190, and the electron transport region may include an ETL. The ETL may include a chrysene-based compound of Formula 1.

The ETL may further include at least one of BCP, Bphen, Alq$_3$, Balq, TAZ, and NTAZ below, in addition to the chrysene-based compound of Formula 1.

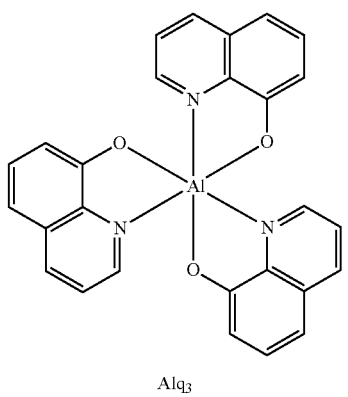

Alq$_3$

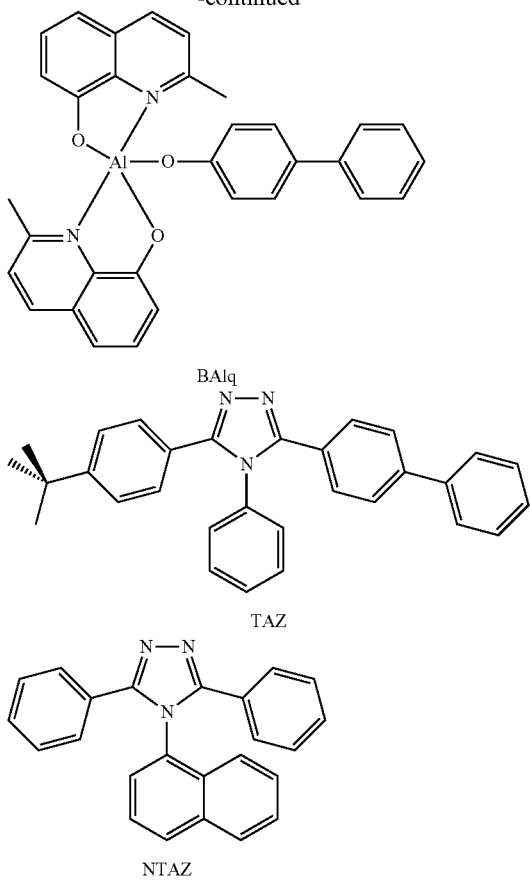

In some embodiments, the ETL may further include at least one of compounds represented by Formula 601 below, in addition to the chrysene-based compound represented by Formula 1:

Ar$_{601}$-[(L$_{601}$)$_{xe1}$-E$_{601}$]$_{xe2}$  <Formula 601>

In Formula 601,

Ar$_{601}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorene group, a spiro-fluorene group, a benzofluorene group, a dibenzofluorene group, a phenalene group, a phenanthrene group an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_3$-C$_{10}$ heterocycloalkyl group, a C$_3$-C$_{10}$ cyclo alkenyl group, a C$_3$-C$_{10}$ heterocyclo alkenyl group, a C$_6$-C$_{60}$ aryl group, a C$_6$-C$_{60}$ aryloxy group, a C$_6$-C$_{60}$ arylthio group, a C$_2$-C$_{60}$ hetero aryl group, a non-aromatic condensed polycyclic group, and —Si(Q$_{301}$)(Q$_{302}$)(Q$_{303}$) (where Q$_{301}$ to Q$_{303}$ are each independently selected from a hydrogen, a C$_1$-C$_{60}$ alkyl group, a C$_2$-C$_{60}$ alkenyl group, a C$_6$-C$_{60}$ aryl group, and a C$_2$-C$_{60}$ heteroaryl group), L$_{601}$ may be defined as described above herein in conjunction with L$_{201}$, E$_{601}$ may be selected from:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a C$_1$-C$_{20}$ alkyl group, a C$_1$-C$_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, xe1 may be selected from 0, 1, 2, and 3, and xe2 may be selected from 1, 2, 3, and 4.

In some other embodiments, the ETL may include at least one of Compounds represented by Formula 602 below, in addition to the chrysene-based compound of Formula 1:

<Formula 602>

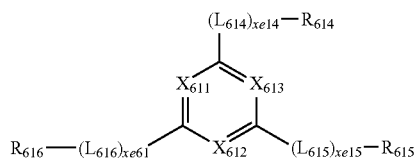

In Formula 602, $X_{611}$ may be N or $C-(L_{611})_{xe611}-R_{611}$, $X_{612}$ may be N or $C-(L_{612})_{xe612}-R_{612}$, $X_{613}$ may be N or $C-(L_{613})_{xe613}-R_{613}$, at least one of $X_{611}$ to $X_{613}$ may be N, $L_{611}$ to $L_{616}$ may be defined as described above in conjunction $L_{201}$, $R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xe611 to xe616 may be each independently selected from, 0, 1, 2, and 3.

The compound of Formula 601 and the compound of Formula 602 may each independently include at least one of Compounds ET1 to ET15 illustrated below.

ET1

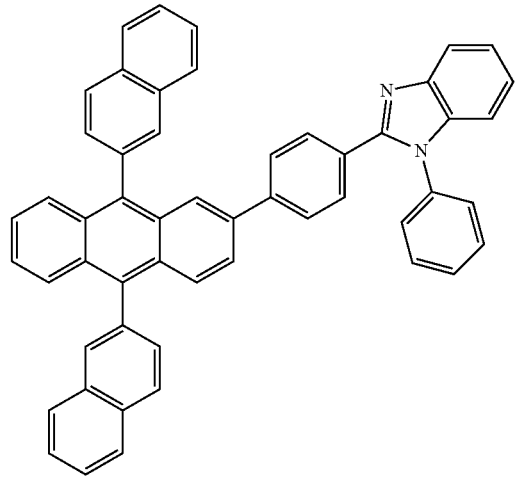

ET2

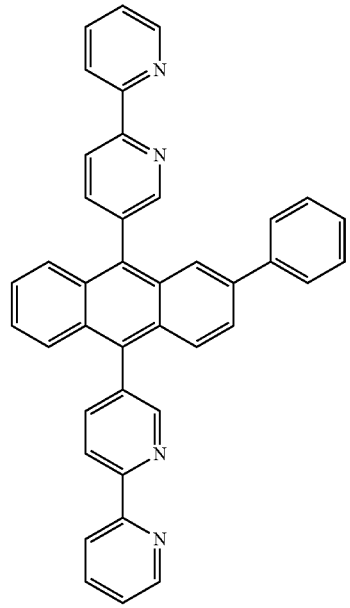

ET3

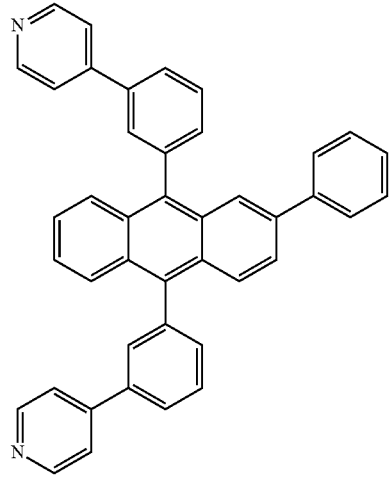

ET4
ET5
ET6
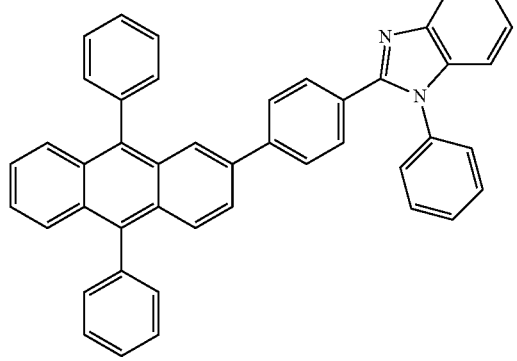
ET7
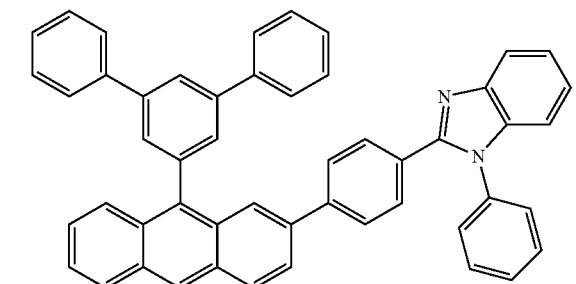
ET8
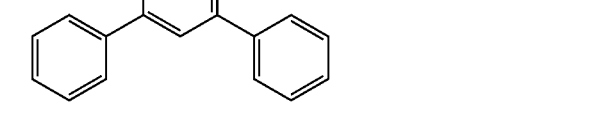
ET9
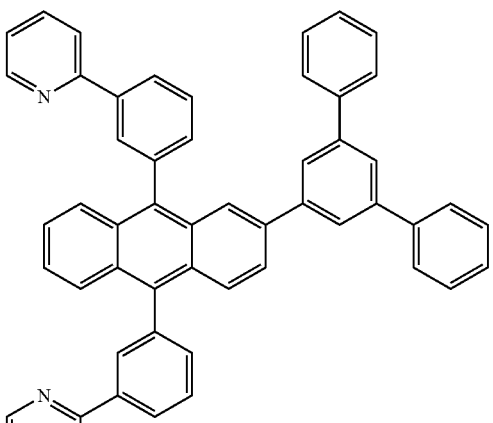
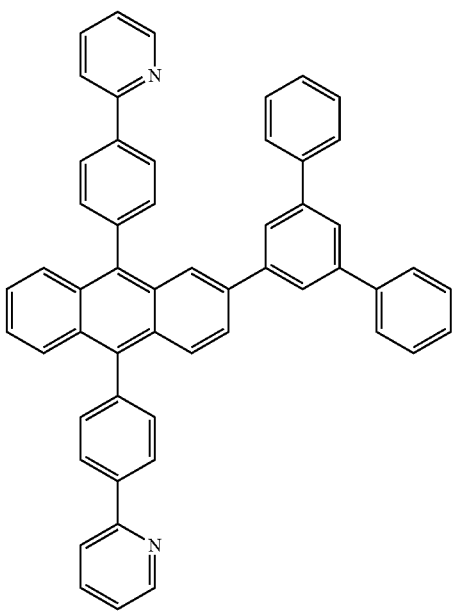

ET10

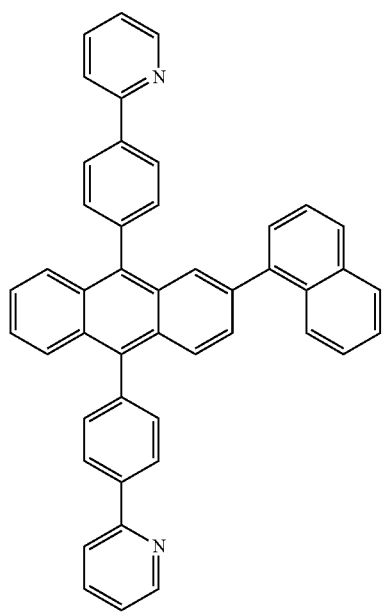

ET11

ET13

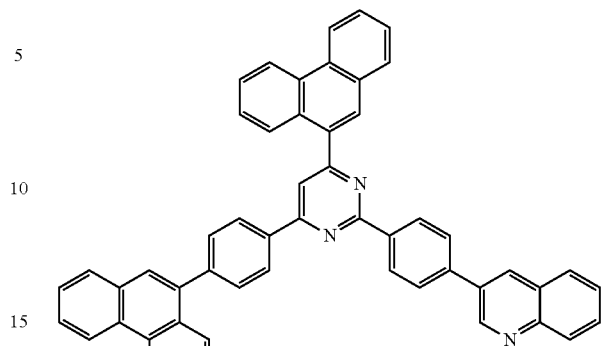

ET14

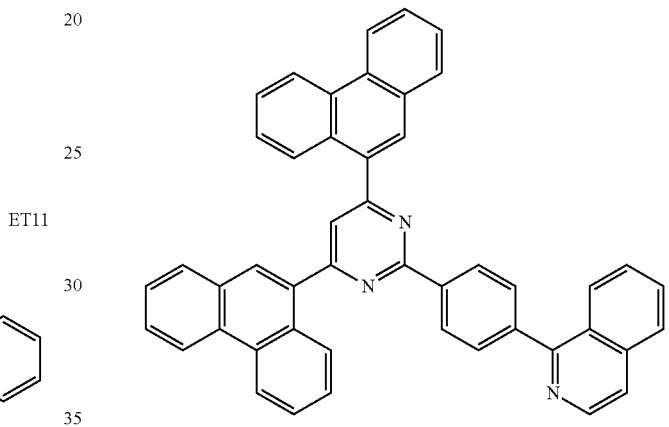

ET15

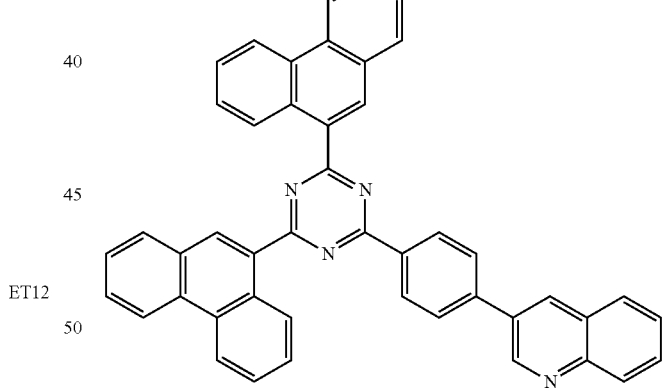

ET12

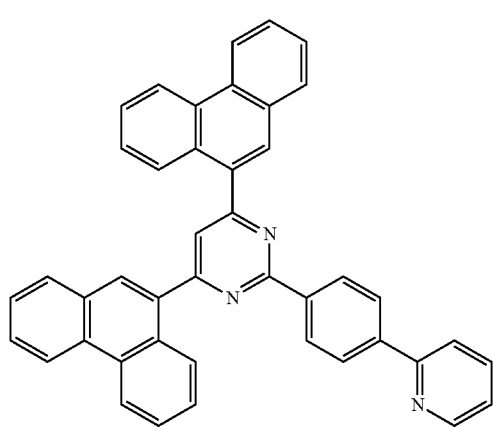

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex may include compound ET-D1 below (lithium quinolate (LiQ)), and compound ET-D2 below.

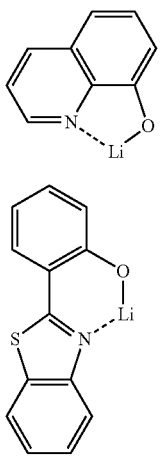

ET-D1

ET-D2

The electron transport region may include an EIL that may facilitate injection of electrons from the second electrode 190.

The EIL may be formed on the ETL by using any of a variety of methods, for example, by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be described in detail.

The EIL may include at least one selected from LiF, NaCl, CsF, $Li_2O$, BaO, and LiQ.

A thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 are lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a reflective electrode, a semi-transmissive electrode, or a transmissive electrode.

Although the organic light-emitting device of FIG. 1 is described above, embodiments are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, a ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a structure including at least one carbon double bond in the middle or terminal of the $C_2$-$C_{60}$ alkyl group. Non-limiting examples of the $C_2$-$C_{60}$ alkenyl group are an ethenyl group, a prophenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a structure including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_3$-$C_{10}$ heterocycloalkyl group refers to a monovalent monocyclic group having 3 to 10 carbon atoms in which at least one hetero atom selected from N, O, P, and S is included as a ring-forming atom. Non-limiting examples of the $C_3$-$C_{10}$ heterocycloalkyl group are a tetrahydrofuranyl group and a tetrahydrothiophenyl group. A $C_3$-$C_{10}$ heterocycloalkylene group refers to a divalent group having the same structure as the $C_3$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_3$-$C_{10}$ heterocycloalkenyl group used herein refers to a monovalent monocyclic group having 3 to 10 carbon atoms that includes at least one double bond in the ring and in which at least one hetero atom selected from N, O, P, and S is included as a ring-forming atom. Non-limiting examples of the $C_3$-$C_{10}$ heterocycloalkenyl group are a 2,3-hydrofuranyl group and a 2,3-hydrothiophenyl group. A $C_3$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a non-aromatic condensed polycyclic group refers to a monovalent group with at least two condensed rings condensed to each other, in which the entire molecule has non-aromaticity). The non-aromatic condensed polycyclic group may include i) only carbon atoms, or ii) carbon atoms and a hetero atom selected from N, O, P, and S as ring-forming atoms. Non-limiting examples of the non-aromatic condensed polycyclic group are a fluorenyl group and a carbazolyl group. As used herein, a divalent non-aromatic condensed polycyclic group refers to a divalent group with the same structure as the non-aromatic condensed polycyclic group.

The acronym "Ph" used herein refers to phenyl, the acronym "Me" used herein refers to methyl, the acronym "Et" used herein refers to ethyl, and the acronym "ter-Bu", "tert-Bu", or "But" used herein refers to tert-butyl.

In the following synthesis example, the expression that "'B' instead of 'A' was used" means that the amounts of 'B' and 'A' were the same in equivalent amounts.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 2

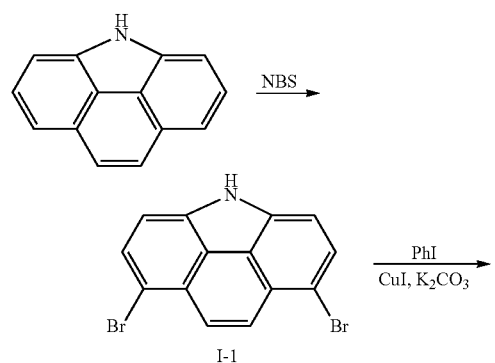

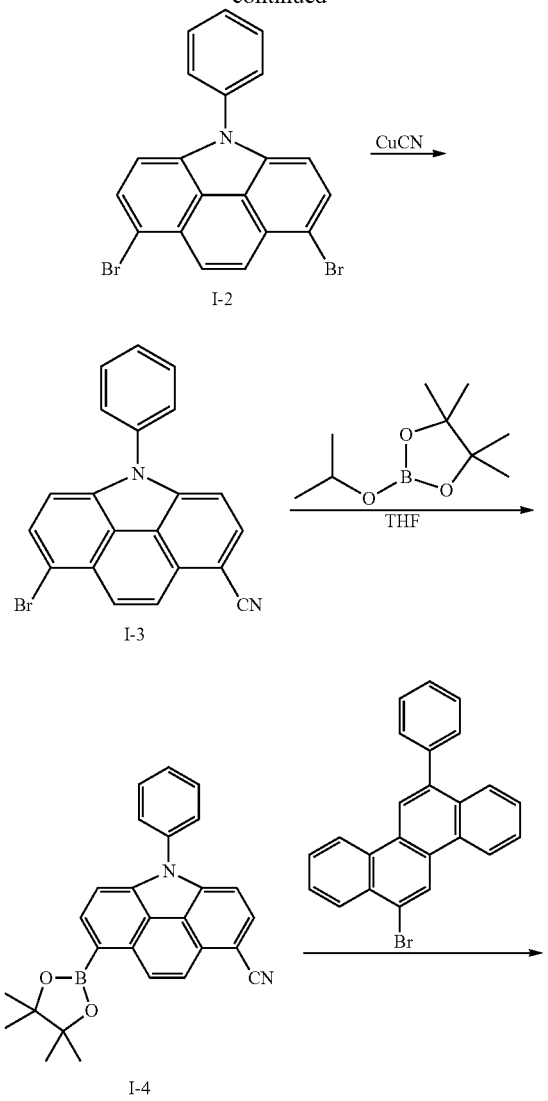

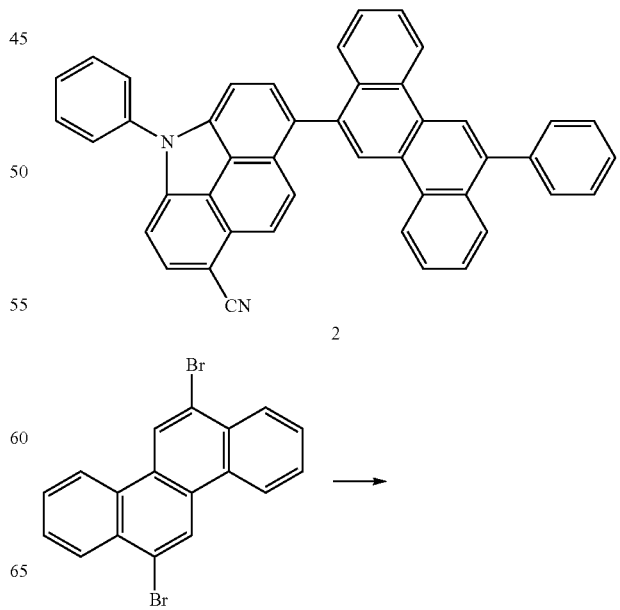

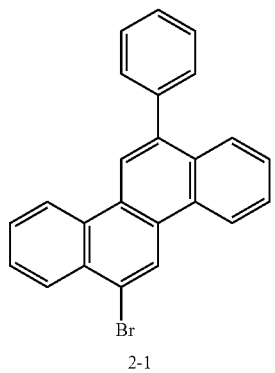

2-1

1) Synthesis of Intermediate I-1

After 9.55 g (50.0 mmol) of 6H-benzo[def]carbazole was completely dissolved in 250 mL of carbon tetrachloride ($CCl_4$), 1.78 g (10.0 mmol) of N-bromosuccinimide was added thereto, and then stirred at about 80° C. for about 30 hours. The resulting reaction solution was cooled down to room temperature, and stirred for about 30 minutes to precipitate crystals. The crystals were collected through a vacuum filter, and washed with methanol to obtain 8.55 g of Intermediate I-1 as white crystals (Yield 49%). This compound was identified using liquid chromatography-mass spectroscopy (LC-MS). $C_{14}H_7Br_2N$: $M^+$ 346.9

2) Synthesis of Intermediate I-2

8.55 g (24.5 mmol) of Intermediate I-1, 6.0 g (29.4 mmol) of iodobenzene, 0.44 g (2.45 mmol) of 1,10-phenanthroline, 0.93 g (4.90 mmol) of CuI, and 10.2 g (73.5 mmol) of $K_2CO_3$ were dissolved in 100 mL of dimethylformamide (DMF), and then stirred at about 80° C. for about 24 hours. The reaction solution was cooled down to room temperature, and then extracted with 100 mL of water. An organic layer was collected and was dried using magnesium sulfate to evaporate the solvent. The residue was separated and purified using silica gel column chromatography to obtain 8.23 g of Intermediate I-2 (Yield: 79%). This compound was identified using LC-MS. $C_{20}H_{11}Br_2N$: $M^+$ 422.9

3) Synthesis of Intermediate I-3

8.23 g (19.3 mmol) of Intermediate I-2 and 2.57 g (28.7 mmol) of CuCN were dissolved in 70 mL of DMF and then stirred at about 150° C. for about 24 hours. The reaction solution was cooled to room temperature, and 60 mL of ammonia water and 60 mL of water were added thereto, followed by three times of extraction with 50 mL of methylene chloride. An organic layer was collected and was dried using magnesium sulfate to evaporate the solvent. The residue was separated and purified using silica gel column chromatography to obtain 3.3 g of Intermediate I-3 (Yield: 46%). This compound was identified using LC-MS. $C_{21}H_{11}BrN_2$: $M^+$ 370.0

4) Synthesis of Intermediate I-4

3.3 g (8.89 mmol) of Intermediate I-3 was dissolved in 60 mL of tetrahydrofurane (THF), and 3.9 mL (9.78 mmol) of n-BuLi (2.5 M in hexane) was slowly dropwise added thereto at about −78° C. After the reaction solution was stirred at the same temperature for about 1 hour, 2.3 mL (11.6 mmol) of 2-isoproxy-4,4,5,5-tetramethyl-1,3,2-dioxaborolane was slowly dropwise added to the reaction solution and then stirred at room temperature for about 24 hours. After completion of the reaction, 40 mL of water was added thereto, followed by three times of extraction with 40 mL of diethyl ether. The organic phase was collected and was dried using magnesium sulfate to evaporate the solvent. The residue was separated and purified using silica gel column chromatography to obtain 2.83 g of Intermediate I-4 (Yield: 76%). This compound was identified using LC-MS. $C_{27}H_{23}BN_2O_2$: $M^+$ 418.2

5) Synthesis of Intermediate 2-1

5.79 g (15 mmol) of 6,12-dibromochrysene, 1.21 g (10 mmol) of phenyl boronic acid, 0.58 g (0.5 mmol) of tetrakis (triphenylphosphine)palladium ($Pd(PPh_3)_4$), and 4.15 g (30 mmol) of $K_2CO_3$ were dissolved in 80 mL of a mixed tetrahydrofuran (THF) and $H_2O$ (2:1 by volume) solution, and then stirred at about 70° C. for about 5 hours. After the reaction solution was cooled down to room temperature, 60 mL of water was added thereto, followed by three times of extraction with 60 mL of ethyl ether. An organic layer was collected and dried using magnesium sulfate to evaporate the solvent. The residue was separated and purified by silica gel column chromatography to obtain 2.30 g of Intermediate I-5 (Yield: 60%). This compound was identified using LC-MS. $C_{24}H_{15}Br$: $M^+$ 382.0

Synthesis of Compound 2

2.83 g (6.76 mmol) of Intermediate I-4, 2.59 g (6.76 mmol) of Intermediate 2-1, 0.39 g (0.34 mmol) of Pd $(PPh_3)_4$, and 2.80 g (20.3 mmol) of $K_2CO_3$ were dissolved in 60 mL of a mixed solution of THF and $H_2O$ (2:1 by volume), and then stirred at about 80° C. for about 12 hours. The resulting reaction solution was cooled down to room temperature, followed by three times of extraction with 50 mL of water and 50 mL of ethylacetate. An organic layer was collected and was dried using magnesium sulfate to evaporate the solvent. The residue was separated and purified using silica gel column chromatography to obtain 3.06 g of Compound 2 (Yield: 76%). This compound was identified using mass spectroscopy/fast atom bombardment (MS/FAB) and $^1H$ nuclear magnetic resonance (NMR). $C_{45}H_{26}N_2$ cal. 594.21. found 594.19.

Synthesis Example 2

Synthesis of Compound 13

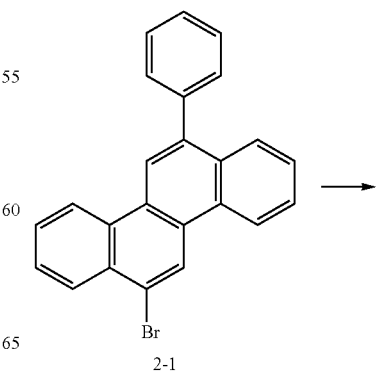

2-1

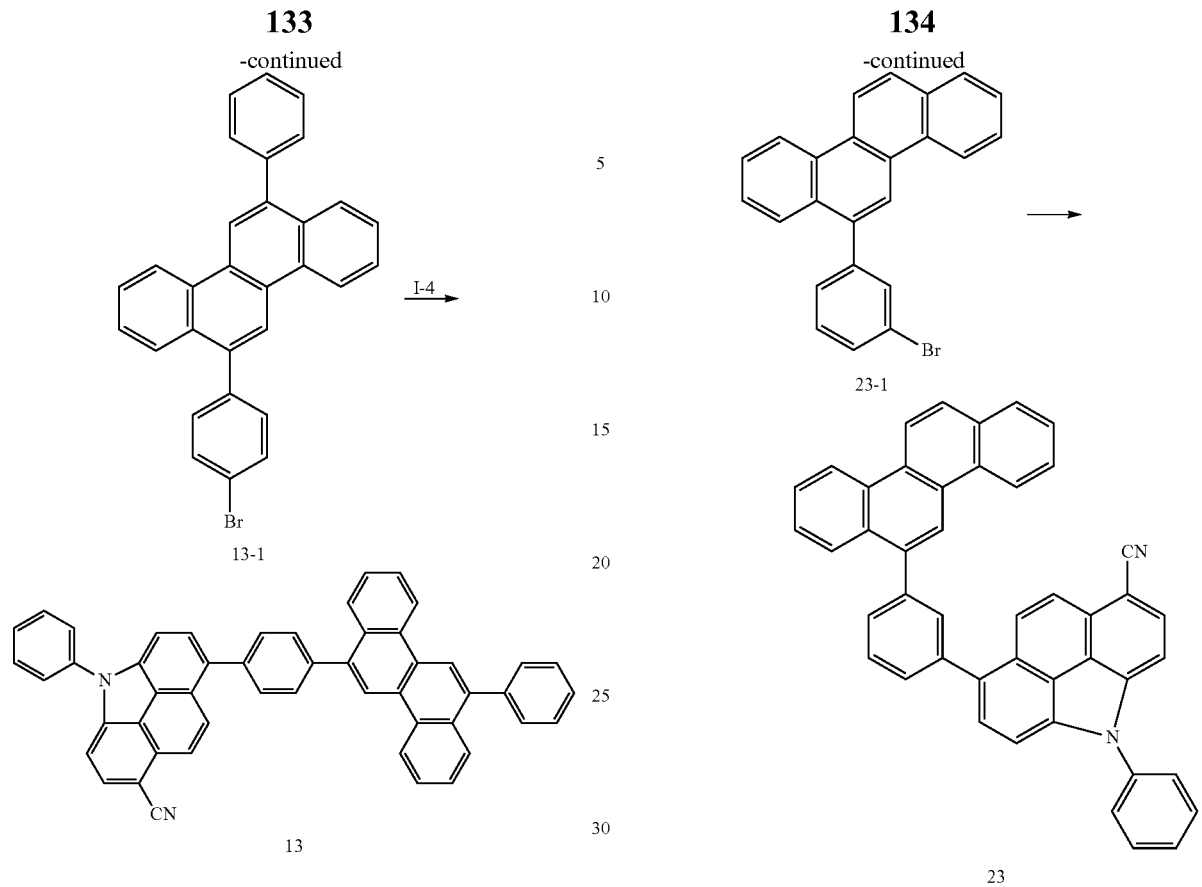

Synthesis of Intermediate 13-1

Intermediate 13-1 (5.30 g, Yield 77%) was obtained in the same manner as in the synthesis of Intermediate 2-1, except that Intermediate 2-1 and 4-bromophenylboronic acid, instead of 6,12-dibromochrysene and phenyl boronic acid, respectively, were used. This compound was identified using LC-MS. $C_{30}H_{19}Br$: $M^+$ 458.1

Synthesis of Compound 13

Compound 35 (3.63 g, Yield: 80%) was obtained in the same manner as in the synthesis of Compound 2, except that Intermediate 13-1 instead of Intermediate 2-1 was used to synthesize Compound 2. This compound was identified using mass spectroscopy/fast atom bombardment (MS/FAB) and $^1H$ nuclear magnetic resonance (NMR). $C_{51}H_{30}N_2$ cal. 670.24. found 670.23.

Synthesis Example 3

Synthesis of Compound 23

Synthesis of Intermediate 23-1

Intermediate 23-1 (4.77 g, Yield 83%) was obtained in the same manner as in the synthesis of intermediate 2-1, except that 6-bromochrysene and 3-bromophenyl boronic acid, instead of 6,12-dibromochrysene and phenyl boronic acid, respectively, were used. This compound was identified using LC-MS. $C_{24}H_{15}Br$: $M^+$ 382.0

Synthesis of Compound 23

Compound 235 (3.14 g, Yield: 78%) was obtained in the same manner as in the synthesis of Compound 2, except that Intermediate 23-1 instead of Intermediate 2-1 was used to synthesize Compound 2. This compound was identified using mass spectroscopy/fast atom bombardment (MS/FAB) and $^1H$ nuclear magnetic resonance (NMR). $C_{45}H_{26}N_2$ cal. 594.21. found 594.20.

Synthesis Example 4

Synthesis of Compound 37

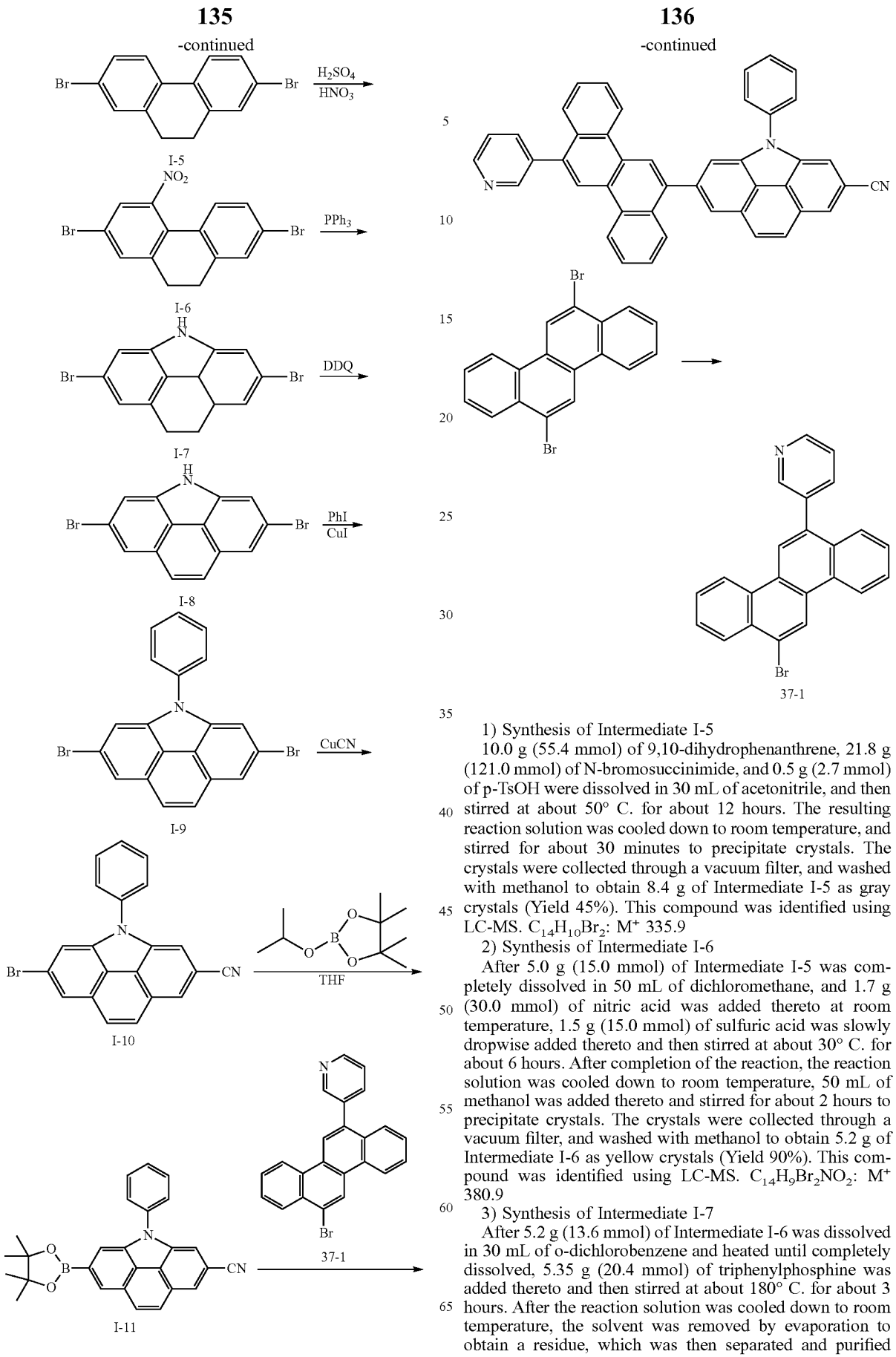

1) Synthesis of Intermediate I-5

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and then stirred at about 50° C. for about 12 hours. The resulting reaction solution was cooled down to room temperature, and stirred for about 30 minutes to precipitate crystals. The crystals were collected through a vacuum filter, and washed with methanol to obtain 8.4 g of Intermediate I-5 as gray crystals (Yield 45%). This compound was identified using LC-MS. $C_{14}H_{10}Br_2$: M+ 335.9

2) Synthesis of Intermediate I-6

After 5.0 g (15.0 mmol) of Intermediate I-5 was completely dissolved in 50 mL of dichloromethane, and 1.7 g (30.0 mmol) of nitric acid was added thereto at room temperature, 1.5 g (15.0 mmol) of sulfuric acid was slowly dropwise added thereto and then stirred at about 30° C. for about 6 hours. After completion of the reaction, the reaction solution was cooled down to room temperature, 50 mL of methanol was added thereto and stirred for about 2 hours to precipitate crystals. The crystals were collected through a vacuum filter, and washed with methanol to obtain 5.2 g of Intermediate I-6 as yellow crystals (Yield 90%). This compound was identified using LC-MS. $C_{14}H_9Br_2NO_2$: M+ 380.9

3) Synthesis of Intermediate I-7

After 5.2 g (13.6 mmol) of Intermediate I-6 was dissolved in 30 mL of o-dichlorobenzene and heated until completely dissolved, 5.35 g (20.4 mmol) of triphenylphosphine was added thereto and then stirred at about 180° C. for about 3 hours. After the reaction solution was cooled down to room temperature, the solvent was removed by evaporation to obtain a residue, which was then separated and purified using silica gel column chromatography, and washed with methanol to obtain 3.5 g of Intermediate I-7 as white crystals (Yield: 73%). This compound was identified using LC-MS. $C_{14}H_{11}Br_2N$: $M^+$ 350.9

4) Synthesis of Intermediate I-8

After 3.5 g (10.0 mmol) of Intermediate I-7 was dissolved in 100 mL of toluene in an oxygen atmosphere, 0.6 g (0.3 mmol) of 2,3-dichloro-5,6-dicyano-1,4-benzoquinone and 0.2 g (0.3 mmol) of $NaNO_2$ were added thereto, and then stirred at about 110° C. for about 6 hours. After completion of the reaction, the reaction solution was cooled down to room temperature, and the solvent was removed by evaporation to obtain a residue, which was then separated and purified using silica gel column chromatography to obtain to obtain 3.1 g of Intermediate I-8 (Yield: 90%). This compound was identified using LC-MS. $C_{14}H_7Br_2N$: $M^+$ 346.9

Synthesis of Intermediate I-9

Intermediate I-9 (8.54 g, Yield: 82%) was obtained in the same manner as in the synthesis of Intermediate I-2, except that Intermediate I-8 instead of Intermediate I-1 was used. This compound was identified using LC-MS. $C_{20}H_{11}Br_2N$: $M^+$ 422.9

6) Synthesis of Intermediate I-10

Intermediate I-10 (3.21 g, Yield: 43%) was obtained in the same manner as in the synthesis of Intermediate I-3, except that Intermediate I-9 instead of Intermediate I-2 was used. This compound was identified using LC-MS. $C_{21}H_{11}BrN_2$: $M^+$ 370.0

7) Synthesis of Intermediate I-11

Intermediate I-11 (2.97 g, Yield: 82%) was obtained in the same manner as in the synthesis of Intermediate I-4, except that Intermediate I-10 instead of Intermediate I-3 was used. This compound was identified using LC-MS. $C_{27}H_{23}BN_2O_2$: $M^+$ 418.2

8) Synthesis of Intermediate 37-1

Intermediate 37-1 (4.09 g, Yield: 71%) was obtained in the same manner as in the synthesis of Intermediate 2-1, except that 3-pyridine boronic acid instead of phenyl boronic acid was used. This compound was identified using LC-MS. $C_{23}H_{14}BrN$: $M^+$ 383.0

Synthesis of Compound 37

Compound 37 (3.06 g, Yield: 76%) was obtained in the same manner as in the synthesis of Compound 2, except that Intermediate I-11 and Intermediate 37-1, instead of Intermediate I-4 and Intermediate 2-1, respectively, were used. This compound was identified using mass spectroscopy/fast atom bombardment (MS/FAB) and $^1H$ nuclear magnetic resonance (NMR). $C_{44}H_{25}N_3$ cal. 595.20. found 595.22.

Synthesis Example 5

Synthesis of Compound 59

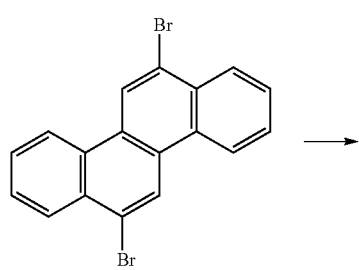

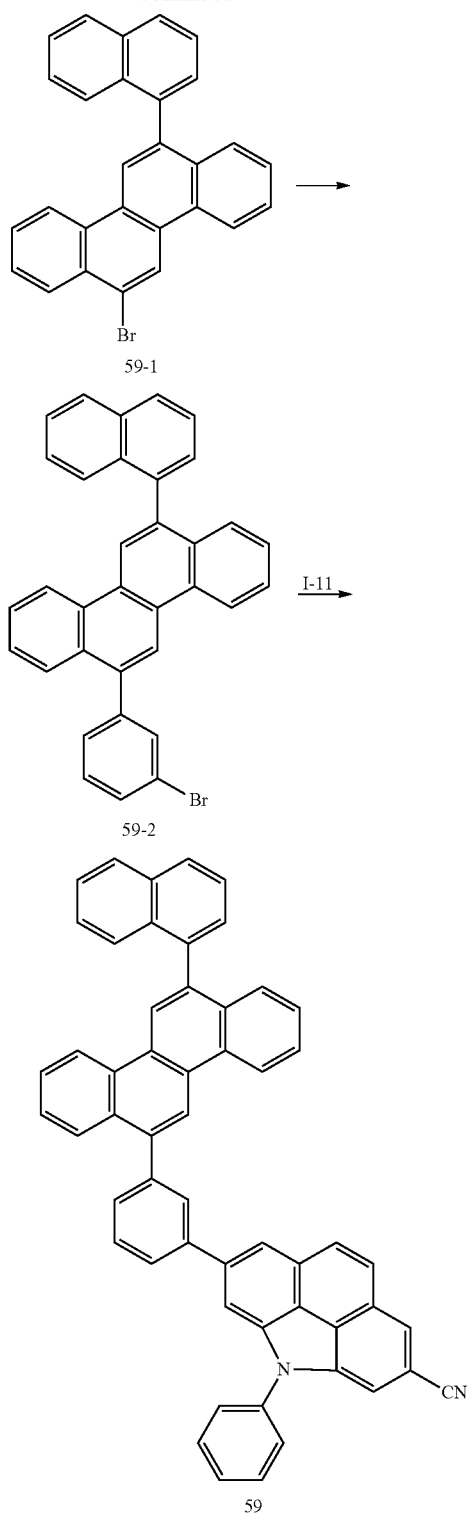

1) Synthesis of Intermediate 59-1

Intermediate 59-1 (4.88 g, Yield: 75%) was obtained in the same manner as in the synthesis of Intermediate 2-1, except that 1-naphthalene boronic acid instead of phenyl boronic acid was used. This compound was identified using LC-MS. $C_{28}H_{17}Br$: $M^+$ 432.0

2) Synthesis of Intermediate 59-2

Intermediate 59-2 (4.42 g, Yield: 77%) was obtained in the same manner as in the synthesis of Intermediate 2-1, except that Intermediate 59-1 and 3-bromophenyl boronic acid instead of 6,12-dibromochrysene and phenyl boronic acid, respectively, were used. This compound was identified using LC-MS. $C_{34}H_{21}Br$: $M^+$ 508.1

Synthesis of Compound 59

Compound 59 (3.52 g, Yield: 72%) was obtained in the same manner as in the synthesis of Compound 2, except that Intermediate I-11 and Intermediate 59-2 instead of Intermediate I-4 and Intermediate 2-1, respectively, were used. This compound was identified using mass spectroscopy/fast atom bombardment (MS/FAB) and $^1$H nuclear magnetic resonance (NMR). $C_{55}H_{32}N_2$ cal. 720.26. found 720.25.

Synthesis Example 6

Synthesis of Compound 68

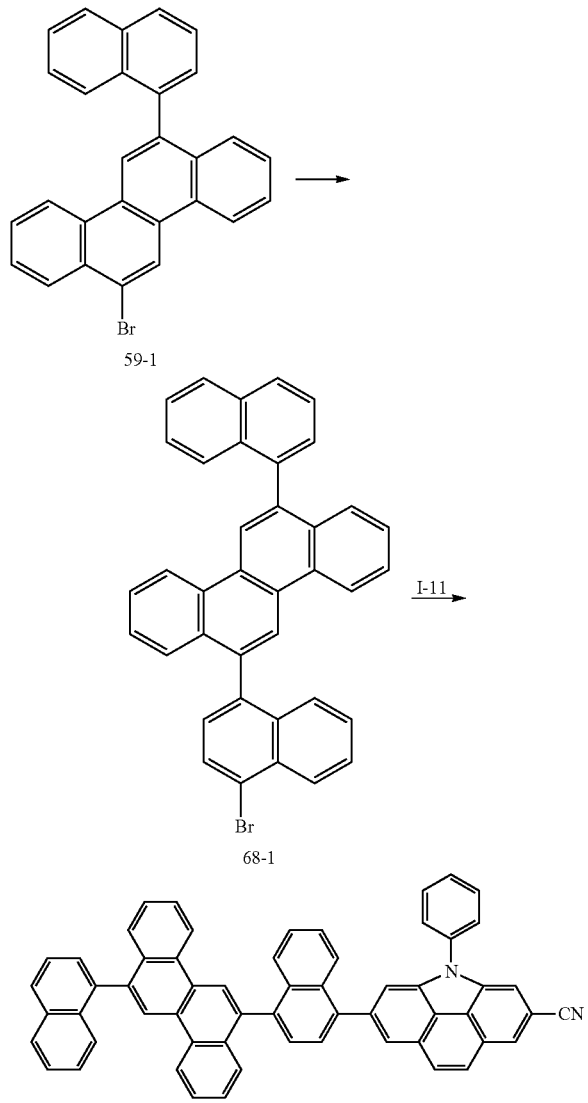

Synthesis of Intermediate 68-1

Intermediate 68-1 (4.98 g, Yield: 79%) was obtained in the same manner as in the synthesis of Intermediate 59-2, except that 4-bromonaphthalene boronic acid instead of 3-bromophenyl boronic acid was used. This compound was identified using LC-MS. $C_{38}H_{23}Br$: $M^+$ 558.1

Synthesis of Compound 68

Compound 68 (4.17 g, Yield: 80%) was obtained in the same manner as in the synthesis of Compound 2, except that Intermediate I-11 and Intermediate 68-1 instead of Intermediate I-4 and Intermediate 2-1, respectively, were used. This compound was identified using mass spectroscopy/fast atom bombardment (MS/FAB) and $^1$H nuclear magnetic resonance (NMR). $C_{59}H_{34}N_2$ cal. 770.27. found 770.25.

Additional compounds were synthesized via the same synthetic pathways by the same method as described above. Analysis data of these compounds by $^1$H NMR and MS/FAB are shown in Table 1 below.

Other compounds not shown in Table 1 may also be synthesized based on the above-described synthetic pathways and source materials.

TABLE 1

| Compound | $^1$H NMR (CDCl$_3$, 400 MHz) | MS/FAB found | MS/FAB calc. |
|---|---|---|---|
| 2 | δ = 8.47-8.46 (m, 1H), 8.40-8.38 (m, 1H), 8.32-8.29 (m, 2H), 8.12-8.03 (m, 4H), 7.88-7.86 (m, 1H), 7.72-7.64 (m, 4H), 7.56-7.46 (m, 8H), 7.43-7.35 (m, 3H), 7.20-7.15 (m, 2H) | 594.19 | 594.21 |
| 6 | δ = 8.60-8.59 (m, 1H), 8.44-8.43 (m, 1H), 8.34-8.32 (m, 1H), 8.25-8.23 (m, 1H), 8.16-8.06 (m, 5H), 7.88-7.86 (m, 1H), 7.82-7.78 (m, 2H), 7.75-7.66 (m, 4H), 7.55-7.47 (m, 8H), 7.43-7.35 (m, 3H), 7.22-7.15 (m, 2H) | 671.25 | 671.24 |
| 8 | δ = 8.52-8.50 (dd, 1H), 8.44-8.42 (m, 2H), 8.36-8.33 (m, 2H), 8.27-8.25 (dd, 1H), 8.19-8.17 (dd, 1H), 8.11-8.06 (m, 3H), 8.02-7.98 (m, 2H), 7.87-7.86 (m, 1H), 7.79-7.77 (m, 1H), 7.74-7.63 (m, 5H), 7.60-7.49 (m, 6H), 7.47-7.35 (m, 4H), 7.22-7.17 (m, 2H) | 725.23 | 721.25 |
| 13 | δ = 8.45-8.44 (m, 1H), 8.38-8.36 (m, 1H), 8.31-8.29 (m, 2H), 8.08-8.03 (m, 3H), 7.87-7.83 (m, 3H), 7.79-7.78 (m, 1H), 7.70-7.63 (m, 6H), 7.55-7.46 (m, 8H), 7.43-7.35 (m, 3H), 7.20-7.16 (m, 2H) | 670.23 | 670.24 |
| 15 | δ = 8.62-8.61 (m, 1H), 8.43-8.42 (m, 1H), 8.33-8.30 (m, 2H), 8.08-8.06 (m, 1H), 7.87-7.83 (m, 4H), 7.79-7.77 (m, 1H), 7.70-7.60 (m, 7H), 7.58-7.47 (m, 8H), 7.43-7.35 (m, 3H), 7.29-7.25 (m, 1H), 7.21-7.17 (m, 2H), 7.08-7.05 (m, 1H) | 720.27 | 720.26 |

TABLE 1-continued

| Compound | $^1$H NMR (CDCl$_3$, 400 MHz) | MS/FAB found | MS/FAB calc. |
|---|---|---|---|
| 20 | δ = 8.68-8.67 (m, 1H), 8.62-8.61 (m, 1H), 8.57-8.55 (m, 4H), 8.53-8.48 (m, 2H), 8.39 (t, 1H), 8.16-8.13 (dd, 1H), 8.09-8.07 (m, 1H), 7.87-7.83 (m, 3H), 7.79-7.78 (m, 1H), 7.73-7.65 (m, 9H), 7.55-7.47 (m, 6H), 7.43-7.37 (m, 3H), 7.30-7.26 (m, 2H), 7.20-7.16 (m, 1H) | 824.30 | 824.29 |
| 23 | δ = 8.49-8.48 (m, 1H), 8.42-8.40 (m, 1H), 8.20-8.19 (m, 1H), 8.17-8.16 (m, 1H), 8.15-8.14 (m, 1H), 8.08-8.00 (m, 3H), 7.97-7.96 (m, 1H), 7.87-7.84 (m, 1H), 7.73-7.69 (m, 2H), 7.67-7.64 (m, 3H), 7.59-7.36 (m, 10H), 7.22-7.18 (m, 1H) | 594.20 | 594.21 |
| 26 | δ = 8.72 (d, 1H), 8.52-8.51 (m, 1H), 8.44-8.42 (m, 1H), 8.31-8.29 (m, 1H), 8.23-8.21 (m, 1H), 8.16-8.14 (m, 2H), 8.08-8.06 (m, 2H), 8.02-8.00 (m, 1H), 7.98-7.92 (m, 2H), 7.87-7.85 (m, 1H), 7.80-7.78 (m, 1H), 7.73-7.69 (m, 1H), 7.65-7.62 (m, 2H), 7.55-7.49 (m, 5H), 7.43-7.41 (m, 1H), 7.39-7.35 (m, 1H), 7.23-7.20 (m, 1H) | 595.19 | 595.20 |
| 29 | δ = 8.52-8.51 (m, 1H), 8.43-8.41 (m, 1H), 8.28-8.27 (m, 1H), 8.22-8.21 (m, 1H), 8.17-8.16 (m, 1H), 8.15-8.14 (m, 1H), 8.08-8.00 (m, 4H), 7.98-7.95 (m, 3H), 7.89-7.87 (m, 1H), 7.73-7.69 (m, 2H), 7.66-7.61 (m, 2H), 7.59-7.46 (m, 7H), 7.43-7.41 (m, 1H), 7.39-7.35 (m, 1H), 7.19-7.15 (m, 1H) | 644.22 | 644.23 |
| 32 | δ = 8.72-8.71 (m, 1H), 8.48-8.46 (m, 1H), 8.40-8.38 (m, 1H), 8.27-8.25 (m, 1H), 8.18-8.15 (m, 1H), 8.08-7.96 (m, 4H), 7.92-7.90 (m, 1H), 7.73-7.62 (m, 5H), 7.55-7.48 (m, 7H), 7.43-7.35 (m, 3H), 7.19-7.15 (m, 1H), 7.07-7.00 (m, 2H) | 644.24 | 644.23 |
| 37 | δ = 8.68-8.67 (m, 1H), 8.60-8.59 (m, 1H), 8.50-8.43 (m, 4H), 8.39-8.37 (m, 1H), 8.24-8.23 (m, 1H), 8.08-8.06 (m, 1H), 8.03 (d, 1H), 7.90-7.87 (m, 1H), 7.85-7.83 (m, 1H), 7.67-7.58 (m, 5H), 7.50-7.48 (m, 2H), 7.46-7.43 (m, 2H), 7.39-7.35 (m, 3H), 7.30-7.26 (m, 1H) | 595.22 | 595.20 |
| 44 | δ = 9.10-9.09 (m, 1H), 8.98-8.97 (m, 1H), 8.66-8.64 (m, 1H), 8.55-8.53 (m, 1H), 8.37-8.35 (m, 1H), 8.31-8.29 (m, 1H), 8.25-8.20 (m, 5H), 8.08-8.07 (m, 1H), 8.03-8.02 (m, 1H), 8.00 (s, 1H), 7.84-7.80 (m, 1H), 7.69-7.59 (m, 5H), 7.52-7.38 (m, 10H), 7.30-7.27 (m, 2H) | 748.25 | 748.26 |
| 49 | δ = 8.64-8.63 (m, 1H), 8.40-8.39 (m, 1H), 8.27-8.24 (m, 2H), 8.09-8.06 (m, 2H), 8.03 (d, 1H), 7.94-7.91 (m, 2H), 7.86-7.84 (m, 1H), 7.81-7.77 (m, 3H), 7.71-7.58 (m, 9H), 7.50-7.46 (m, 3H), 7.41-7.35 (m, 3H), 7.29-7.25 (m, 1H), 7.20-7.15 (m, 2H), 7.06-7.02 (m, 1H) | 720.27 | 720.26 |
| 53 | δ = 8.68-8.66 (dd, 1H), 8.49-8.48 (m, 2H), 8.40-8.39 (m, 1H), 8.38-8.37 (m, 1H), 8.26-8.24 (dd, 2H), 8.19-8.17 (dd, 1H), 8.12-8.10 (dd, 1H), 8.08-8.05 (m, 1H), 8.03-7.99 (m, 3H), 7.94-7.90 (m, 2H), 7.80-7.77 (m, 4H), 7.74-7.71 (m, 2H), 7.67-7.56 (m, 7H), 7.50-7.44 (m, 3H), 7.40-7.34 (m, 2H), 7.20-7.16 (m, 2H) | 797.26 | 797.28 |
| 59 | δ = 8.64-8.63 (m, 1H), 8.40-8.39 (m, 1H), 8.37-8.32 (m, 2H), 8.17-8.16 (m, 1H), 8.08-8.07 (m, 1H), 8.05-8.03 (m, 2H), 7.86-7.82 (m, 2H), 7.75-7.58 (m, 10H), 7.51-7.46 (m, 3H), 7.41-7.36 (m, 4H), 7.33-7.16 (m, 4H), 7.08-7.04 (m, 1H) | 720.25 | 720.26 |
| 65 | δ = 8.63-8.62 (m, 1H), 8.41-8.40 (m, 1H), 8.37-8.33 (m, 2H), 8.22-8.21 (m, 1H), 8.19-8.18 (m, 1H), 8.16-8.12 (m, 2H), 8.09-8.05 (m, 2H), 8.03 (d, 1H), 7.96-7.94 (dd, 1H), 7.86-7.82 (m, 3H), 7.71-7.58 (m, 8H), 7.50-7.46 (m, 3H), 7.43 (d, 1H), 7.41-7.35 (m, 3H), 7.29-7.16 (m, 3H), 7.09-7.05 (m, 1H) | 770.28 | 770.27 |
| 68 | δ = 8.78-8.77 (m, 1H), 8.68-8.67 (m, 1H), 8.40-8.38 (m, 2H), 8.30-8.27 (m, 1H), 8.16-8.15 (m, 1H), 8.09-8.08 (m, 1H), 8.04-8.02 (m, 2H), 7.86-7.80 (m, 2H), 7.73-7.59 (m, 10H), 7.50-7.46 (m, 3H), 7.42-7.35 (m, 4H), 7.29-7.27 (m, 2H), 7.20-7.16 (m, 2H), 7.08-7.01 (m, 3H) | 770.25 | 770.27 |
| 70 | δ = 8.63-8.62 (m, 1H), 8.38-8.35 (m, 2H), 8.33-8.31 (m, 1H), 8.29-8.27 (m, 1H), 8.20-8.19 (m, 1H), 8.08-8.04 (m, 3H), 7.87-7.84 (m, 1H), 7.74-7.64 (m, 4H), 7.57-7.53 (m, 2H), 7.50-7.47 (m, 4H), 7.43-7.35 (m, 5H), 7.19-7.15 (m, 1H) | 594.20 | 594.21 |
| 73 | δ = 8.55-8.54 (m, 1H), 8.45-8.44 (m, 1H), 8.40-8.39 (m, 1H), 8.38-8.37 (m, 1H), 8.15-8.14 (m, 1H), 8.08-8.03 (m, 3H), 7.94-7.90 (m, 2H), 7.81-7.77 (m, 4H), 7.70-7.64 (m, 4H), 7.58-7.53 (m, 2H), 7.50-7.45 (m, 4H), 7.43-7.37 (m, 3H), 7.35 (d, 1H), 7.18-7.14 (m, 2H) | 670.23 | 670.24 |
| 74 | δ = 8.65-8.65 (m, 1H), 8.45-8.44 (m, 1H), 8.33-8.30 (m, 2H), 8.15-8.14 (m, 1H), 8.08-8.06 (m, 1H), 7.94-7.90 (m, 2H), 7.86-7.84 (m, 1H), 7.81-7.77 (m, 4H), 7.71-7.53 (m, 8H), 7.49-7.46 (m, 3H), 7.43-7.34 (m, 4H), 7.29-7.25 (m, 1H), 7.21-7.16 (m, 2H), 7.07-7.03 (m, 1H) | 720.27 | 720.26 |

Example 1

A corning 15 Ω/cm² (1,200 Å) ITO glass substrate was cut to a size of 50 mm×50 mm×0.7 mm and then sonicated in isopropyl alcohol and pure water each for 15 minutes, and then cleaned by irradiation of ultraviolet rays for 30 minutes and exposure to ozone. The resulting ITO glass substrate was loaded into a vacuum deposition device.

After 2-TNATA was vacuum-deposited on the ITO to form an HIL having a thickness of 600 Å, NPB was deposited on the HIL to form a HTL having a thickness of about 300 Å, and then ADN (as a host) below and DPAVBi (as a dopant) below were co-deposited in a weight ratio of 98:2 on the HTL to form an EML having a thickness of about 300 Å.

Then, Compound 2 was vacuum-deposited on the EML to form an ETL having a thickness of about 300 Å, and then LiF was deposited on the ETL to form an EIL having a thickness of about 10 Å. Then, Al was deposited on the EIL to form a cathode having a thickness of about 3,000 Å, thereby completing the manufacture of an organic light-emitting device.

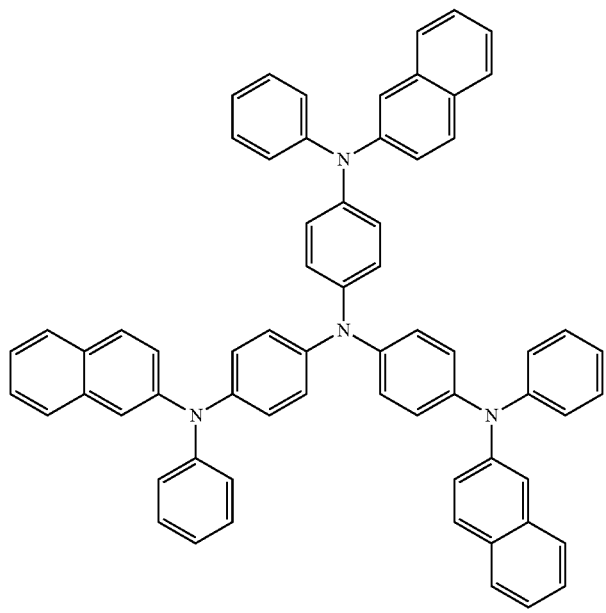
2-TNATA
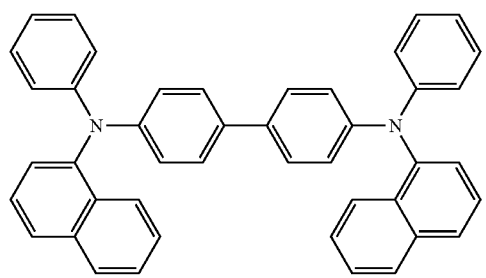
NPB
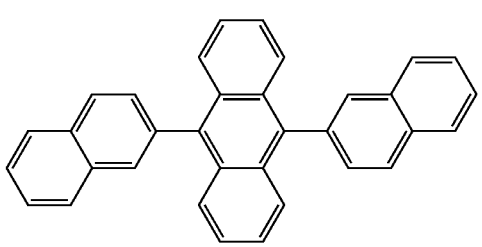
ADN
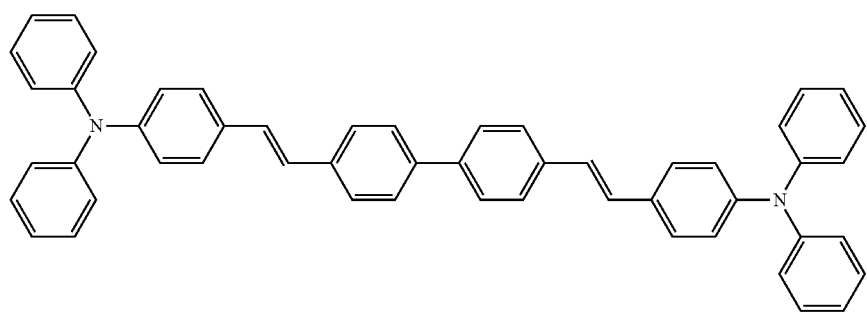
DPAVBi
Example 2
An organic light-emitting device was manufactured in the same manner as in Example 1, except that Compound 13 instead of Compound 2 was used to form the ETL.
Example 2
An organic light-emitting device was manufactured in the same manner as in Example 1, except that Compound 68 instead of Compound 2 was used to form the ETL.

Comparative Example 1

An organic light-emitting device was manufactured in the same manner as in Example 1, except that Alq$_3$ instead of Compound 2 was used to form the ETL.

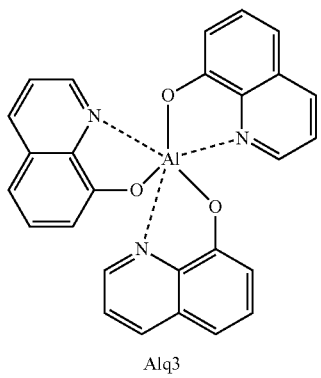

Alq3

Comparative Example 2

An organic light-emitting device was manufactured in the same manner as in Example 1, except that Compound A instead of Compound 2 was used to form the ETL.

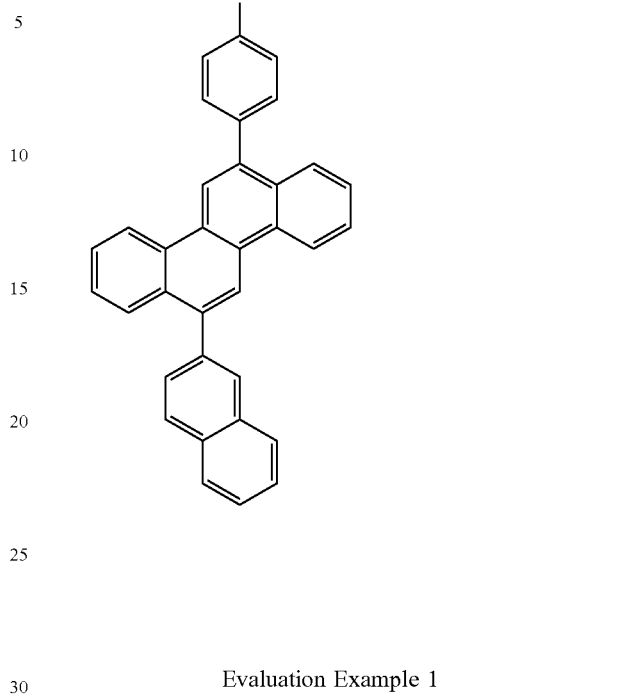

<Compound A>

Evaluation Example 1

Driving voltages, current densities, luminances, efficiencies, and half-lifetimes of the organic light-emitting devices of Examples 1 to 9 and a Comparative Examples 1 to 3 were evaluated using a Kethley Source-Measure Unit (SMU 236) and a PR650 Spectroscan available from Photo Research, Inc. The results are shown in Table 2 below. A half-lifetime was measured as the time taken until a measured initial luminocity (assumed as 100%) is reduced to 50%.

TABLE 2

| Example | ETL | Driving voltage (V) | Current density (mA/cm$^2$) | Luminance (cd/m$^2$) | Efficiency (cd/A) | Emission color | Half-life-time (hr @100 mA/cm$^2$) |
|---|---|---|---|---|---|---|---|
| Example 1 | Compound 2 | 5.14 | 50 | 3,175 | 6.35 | Blue | 465 hr |
| Example 2 | Compound 13 | 5.38 | 50 | 3,205 | 6.41 | Blue | 409 hr |
| Example 3 | Compound 20 | 5.49 | 50 | 2,985 | 5.97 | Blue | 431 hr |
| Example 4 | Compound 32 | 5.07 | 50 | 3,110 | 6.22 | Blue | 482 hr |
| Example 5 | Compound 44 | 5.81 | 50 | 3,035 | 6.07 | Blue | 424 hr |
| Example 6 | Compound 59 | 5.62 | 50 | 2,820 | 5.64 | Blue | 352 hr |
| Example 7 | Compound 68 | 5.46 | 50 | 3,160 | 6.32 | Blue | 397 hr |
| Comparative Example 1 | Alq$_3$ | 7.35 | 50 | 2,065 | 4.13 | Blue | 145 hr |
| Comparative Example 2 | Compound A | 6.27 | 50 | 2,955 | 5.91 | Blue | 243 hr |

Referring to Table 2, the organic light-emitting devices of Examples 1 to 3 exhibited improved driving voltages, improved luminances, improved efficiencies, and improved half-lifetimes, compared to those of the organic light-emitting devices of Comparative Example 1 and 2. The organic light-emitting devices of Examples 1 to 3 had a driving voltage lower than the organic light-emitting device of Comparative Example 1 by about 1V or greater, and had significantly improved lifetime characteristics.

As described above, according to the one or more of the above embodiments, an organic light-emitting device including a chrysene-based compound of Formula 1 above may have a high efficiency, a low driving voltage, and a long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A chrysene-based compound represented by Formula 1:

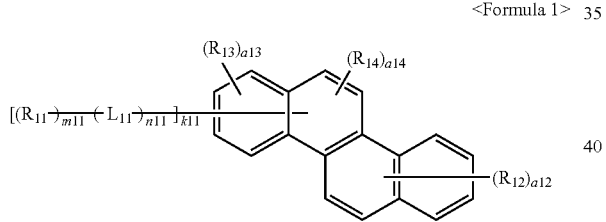

<Formula 1> wherein, in Formula 1, $L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, and a substituted or unsubstituted non-aromatic condensed polycyclic group, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, and the substituted non-aromatic condensed polycyclic group is selected from:

a deuterium atom, a halogen atom, a hydroxyl group, a cyano group, a nitro group, an amino group, an amidino group a hydrazine group, a hydrazone group, a carboxylic acid group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, n11 is an integer selected from 0 to 3, $R_{11}$ is a group represented by one of Formulae 2-1 and 2-2, below, m11 is an integer selected from 1 to 3, k11 is an integer selected from 1 to 4, $R_{12}$ to $R_{14}$ are each independently selected from:

a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group; and a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, each substituted with at least one of a deuterium, a halogen, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cyclo alkenyl group, a $C_1$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group, a12 is an integer selected from 1 to 5, a13 and a14 are each independently an integer selected from 0 to 3,

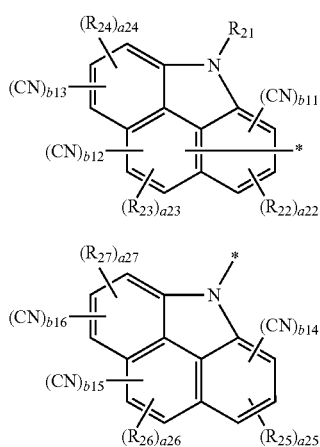

<Formula 2-1>

<Formula 2-2> wherein, in Formulae 2-1 and 2-2, $R_{21}$ to $R_{27}$ are each independently selected from:
a hydrogen, a deuterium, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group a hydrazine group, a hydrazone group, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cyclo alkenyl group, a $C_3$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, a22 to a27 are each independently an integer selected from 0 to 3, b11 to b16 are each independently selected from an integer from 0 to 2, wherein a sum of b11, b12, and b13 is 1 or greater, and a sum of b14, b15, and b16 is 1 or greater, and

* is a binding site to $L_{11}$ or the chrysene moiety in Formula 1.

2. The chrysene-based compound as claimed in claim 1, wherein n11 is an integer selected from 1 to 3, and $L_{11}$ is a group represented by one of Formulae 3-1 to 3-32:

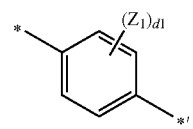

3-1

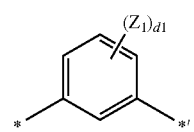

3-2

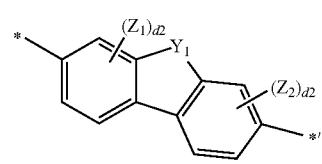

3-3

-continued
3-4
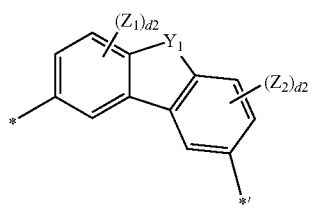
3-5
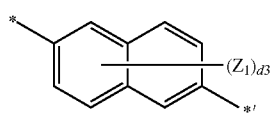
3-6
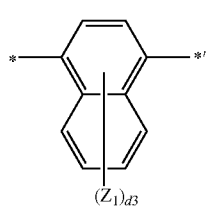
3-7
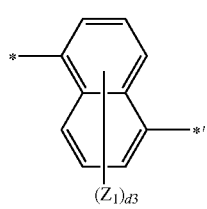
3-8
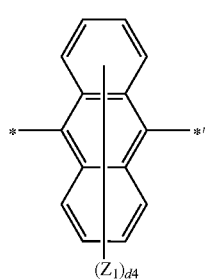
3-9
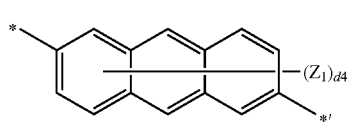
3-10
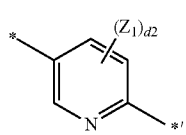
3-11
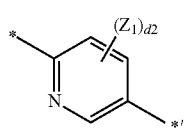
3-12
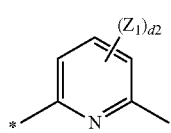
-continued
3-13
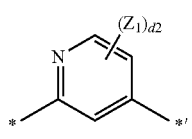
3-14
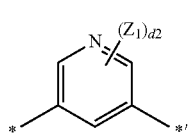
3-15
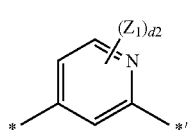
3-16
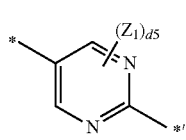
3-17
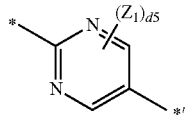
3-18
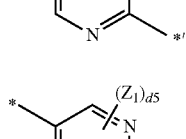
3-19
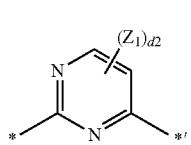
3-20
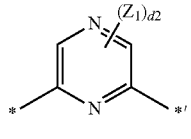
3-21
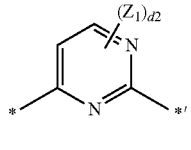
3-22
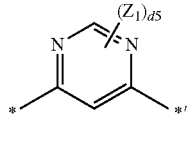
3-23

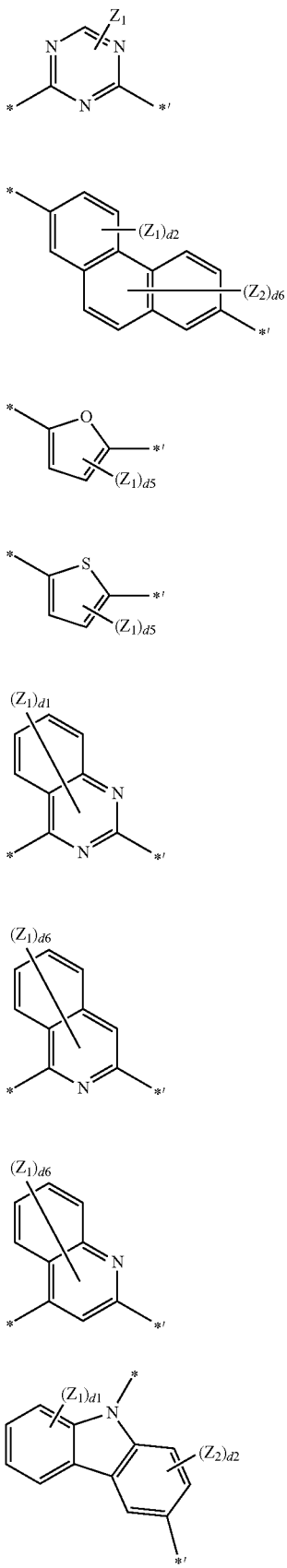
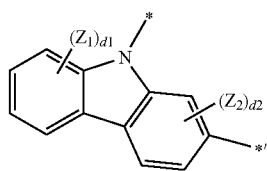

wherein, in Formulae 3-1 to 3-32,
Y$_1$ is selected from C(Q$_{31}$)(Q$_{32}$), N(Q$_{33}$), an oxygen atom, a sulfur atom, and Si(Q$_{34}$)(Q$_{35}$),
Q$_{31}$ to Q$_{35}$ are each independently selected from a hydrogen, a deuterium, a C$_1$-C$_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
Z$_1$ and Z$_2$ are each independently selected from a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid group and a salt thereof, a phosphoric acid group and a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
d1 is an integer selected from 1 to 4,
d2 is an integer selected from 1 to 3,
d3 is an integer selected from 1 to 6,
d4 is an integer selected from 1 to 8,
d5 is an integer selected from 1 or 2,
d6 is an integer selected from 1 to 5, and
* and *' represent binding sites of L$_{11}$ in the compound of Formula 1.

3. The chrysene-based compound as claimed in claim 1, wherein n11 is an integer selected from 1 to 3, and L$_{11}$ is a group represented by one of Formulae 4-1 to 4-23:

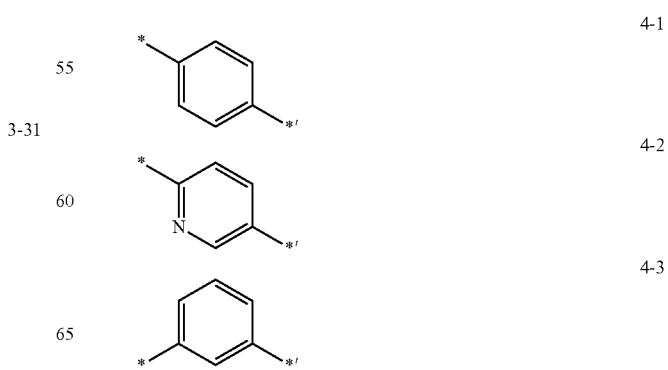

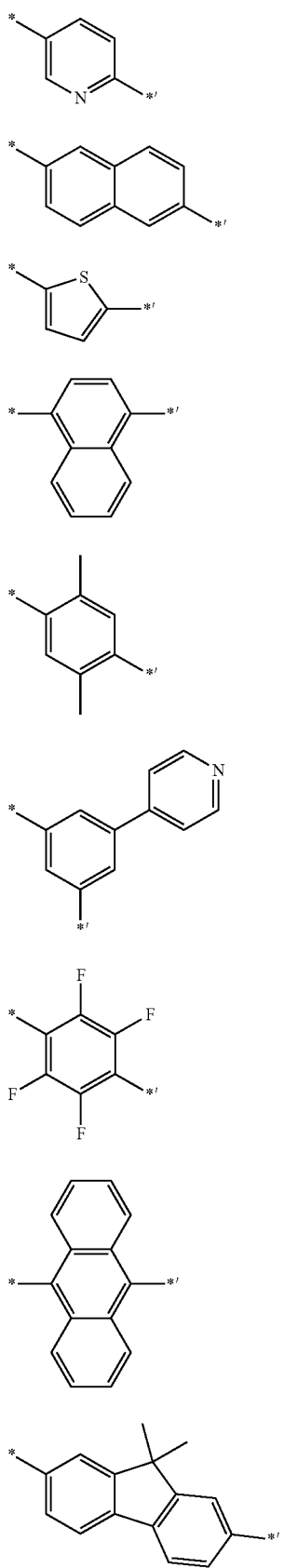
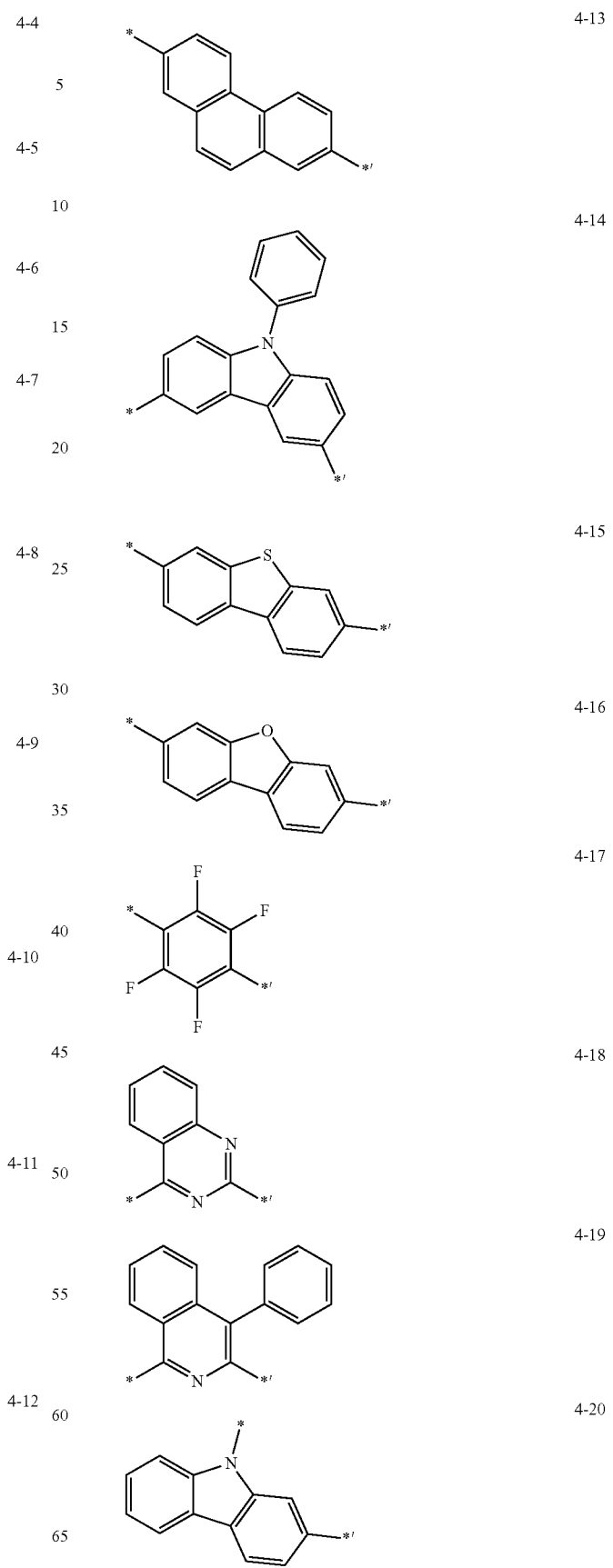

-continued 4-21
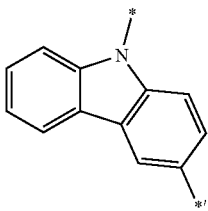

4-22
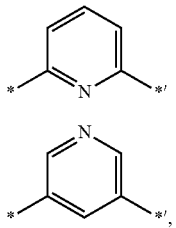

4-23 wherein * and *' represent binding sites of $L_{11}$ in the compound of Formula 1.

4. The chrysene-based compound as claimed in claim 1, wherein n11 is an integer of 0 or 1.

5. The chrysene-based compound as claimed in claim 1, wherein $R_{11}$ is a group represented by one of Formulae 2-1a and 2-2a:

<Formula 2-1a>
<Formula 2-2a>
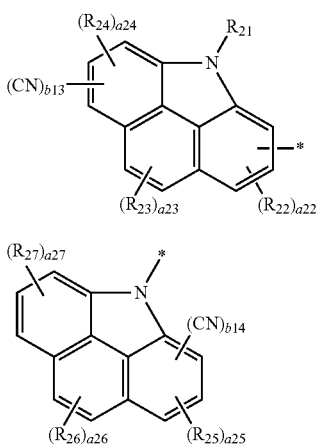

wherein, in Formulae 2-1a and 2-2a,
$R_{21}$ to $R_{27}$ are each independently selected from:
  a hydrogen, a deuterium, a halogen atom, a hydroxyl group, a cyano group, a nitro group, a $C_1$-$C_{60}$ alkyl group, and a $C_1$-$C_{60}$ alkoxy group;
  a $C_1$-$C_{60}$ alkyl group and a $C_1$-$C_{60}$ alkoxy group, each substituted with at least one of a deuterium atom, a halogen atom, a hydroxyl group, a cyano group, a nitro group a $C_6$-$C_{60}$ aryl group, a $C_2$-$C_{60}$ heteroaryl group, and a non-aromatic condensed polycyclic group;
  a $C_6$-$C_{60}$ aryl group, a $C_2$-$C_{60}$ heteroaryl group, and a non-aromatic condensed polycyclic group; and
  a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group, a22 to a27 are each independently an integer selected from 0 to 3,
b13 and b14 are each independently an integer of 1 or 2, and
* is a binding site to $L_{11}$ or the chrysene moiety in Formula 1.

6. The chrysene-based compound as claimed in claim 1, wherein $R_{11}$ is a group represented by Formula 2-1b:

<Formula 2-1b>
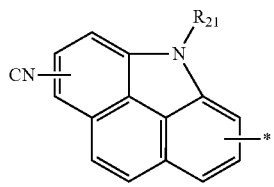

wherein, in Formula 2-1b,
$R_{21}$ is selected from:
  a $C_6$-$C_{60}$ aryl group, a $C_2$-$C_{60}$ heteroaryl group, and a non-aromatic condensed polycyclic group; and
  a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group, and
* is a binding site to $L_{11}$ or the chrysene moiety in Formula 1.

7. The chrysene-based compound as claimed in claim 1, wherein $R_{12}$ to $R_{14}$ are each independently selected from:
  a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid group and a salt thereof, a phosphoric acid group and a salt thereof, a $C_1$-$C_{20}$ alkyl group, and a $C_1$-$C_{20}$ alkoxy group;
  a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and
  a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

8. The chrysene-based compound as claimed in claim 1, wherein $R_{12}$ and $R_{14}$ are each independently selected from:
a hydrogen, a deuterium, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group;
a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group; and
a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one selected from a deuterium, a halogen atom, a cyano group, a nitro group, a $C_1$-$C_{20}$alkyl group, a $C_1$-$C_{20}$alkoxy group, a phenyl group, a naphthyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

9. The chrysene-based compound as claimed in claim 1, wherein $R_{12}$ is selected from a hydrogen, a deuterium, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and groups represented by Formulae 5-1 to 5-38, in which * represents a binding side to the chrysene moiety in Formula 1:

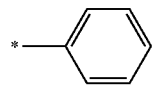
5-1

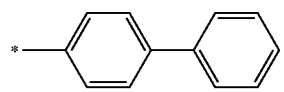
5-2

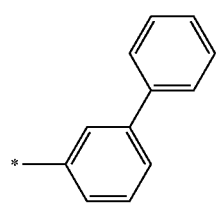
5-3

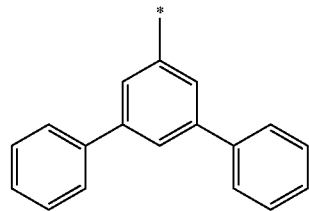
5-4

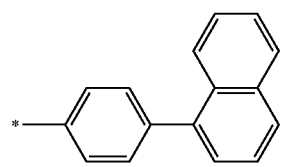
5-5

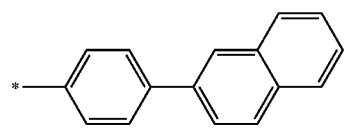
5-6

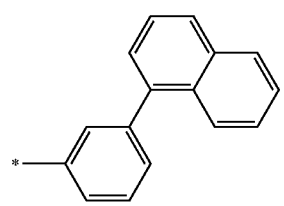
5-7

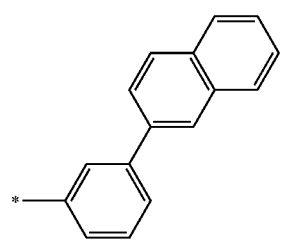
5-8

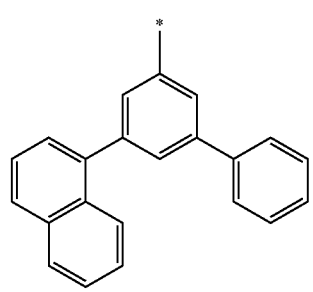
5-9

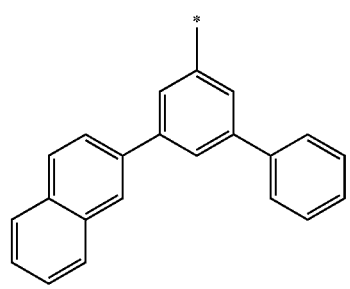
5-10

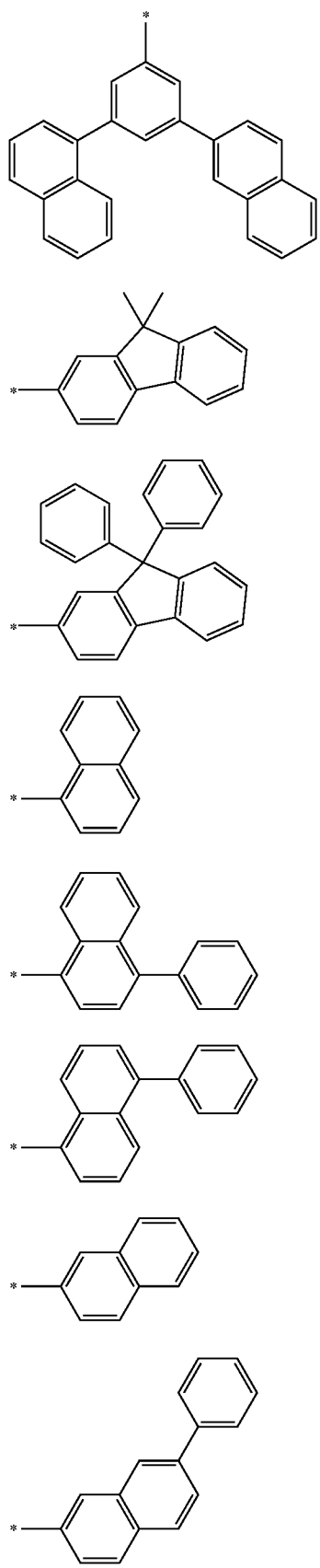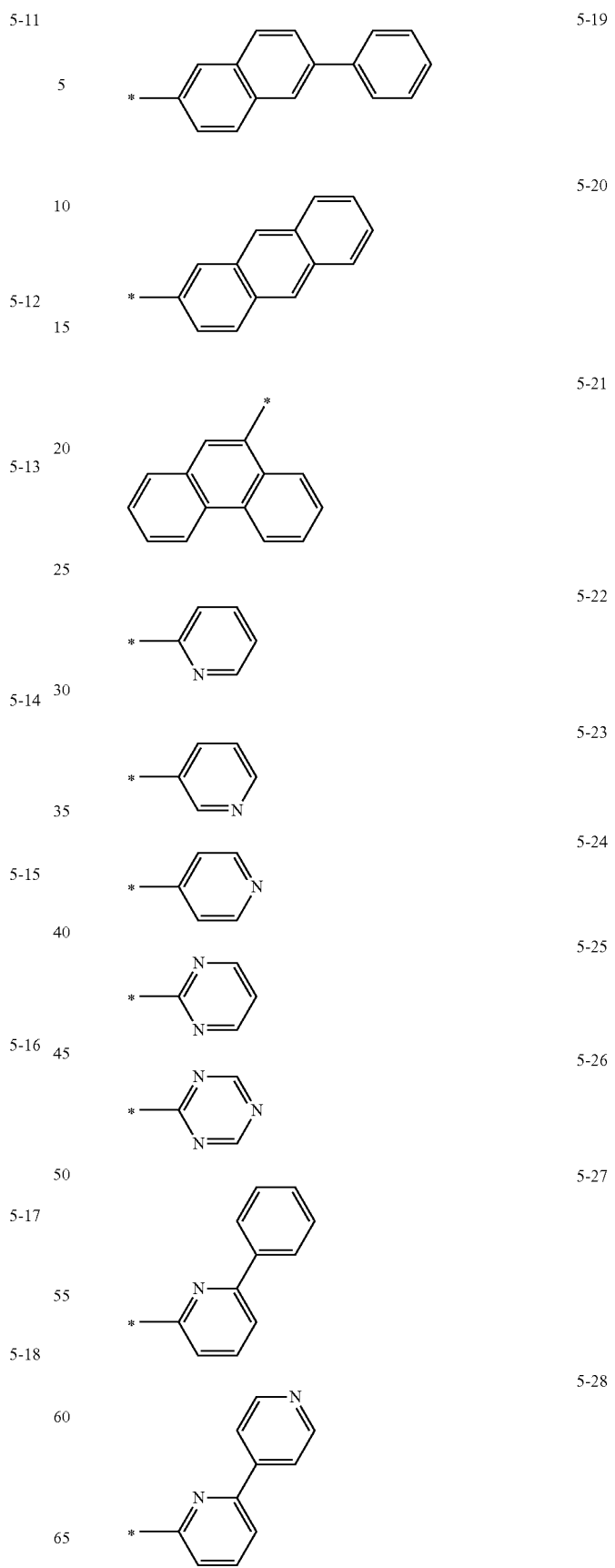

-continued 5-29
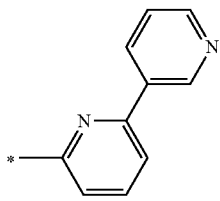

5-30
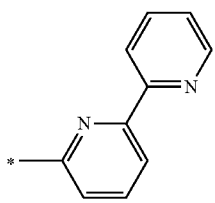

5-31
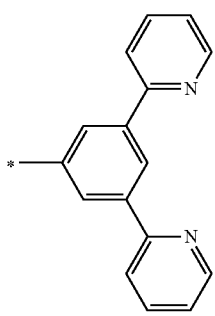

5-32
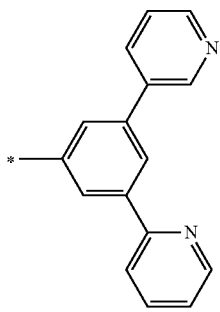

5-33
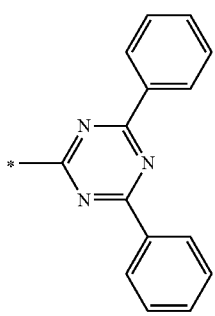

-continued 5-34
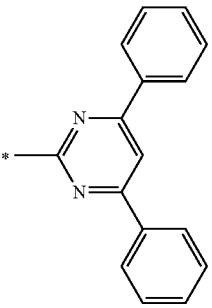

5-35
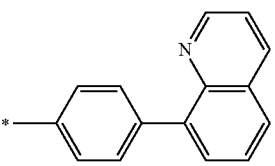

5-36
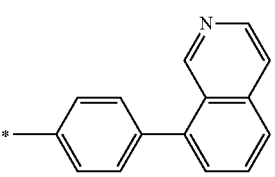

5-37
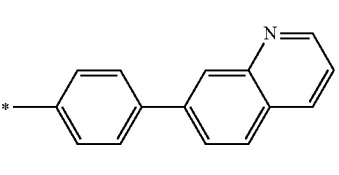

5-38
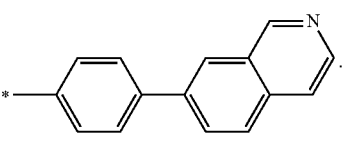

10. The chrysene-based compound as claimed in claim 1, wherein $R_{13}$ and $R_{14}$ are each independently selected from a hydrogen, a deuterium, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group.

11. The chrysene-based compound as claimed in claim 1, wherein a12 is 1.

12. The chrysene-based compound as claimed in claim 1, wherein the chrysene-based compound represented by Formula 1 is represented by Formula 1-1:

<Formula 1-1>
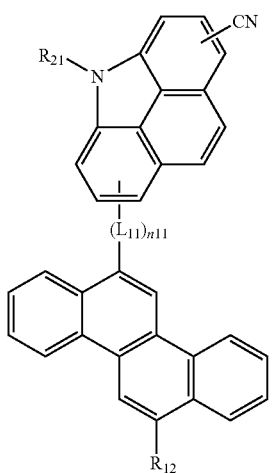
wherein, in Formula 1-1, $L_{11}$, n11, $R_{12}$, and $R_{21}$ are the same as those defined with respect to Formula 1.
13. The chrysene-based compound as claimed in claim 12, wherein n11 is 1, and $L_{11}$ is a group represented by one of Formulae 4-1 to 4-23:
4-1
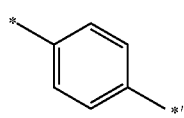
4-2
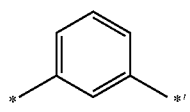
4-3
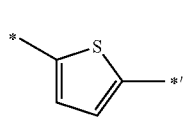
4-4
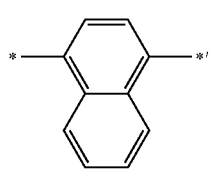
4-5
4-6
4-7
4-8
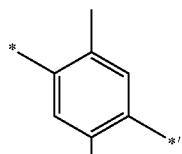
4-9
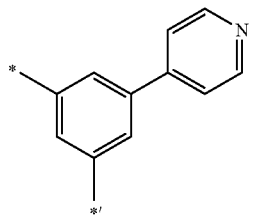
4-10
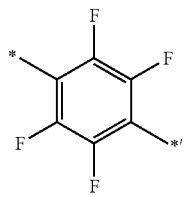
4-11
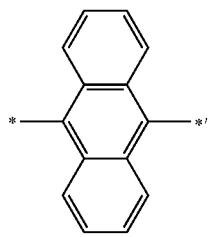
4-12
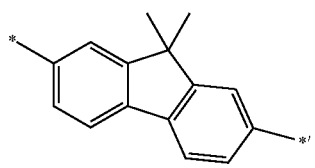
4-13
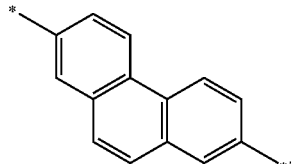
4-14
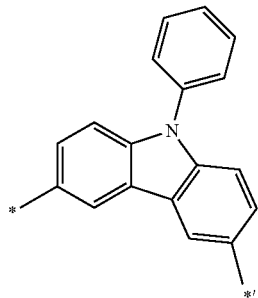

-continued

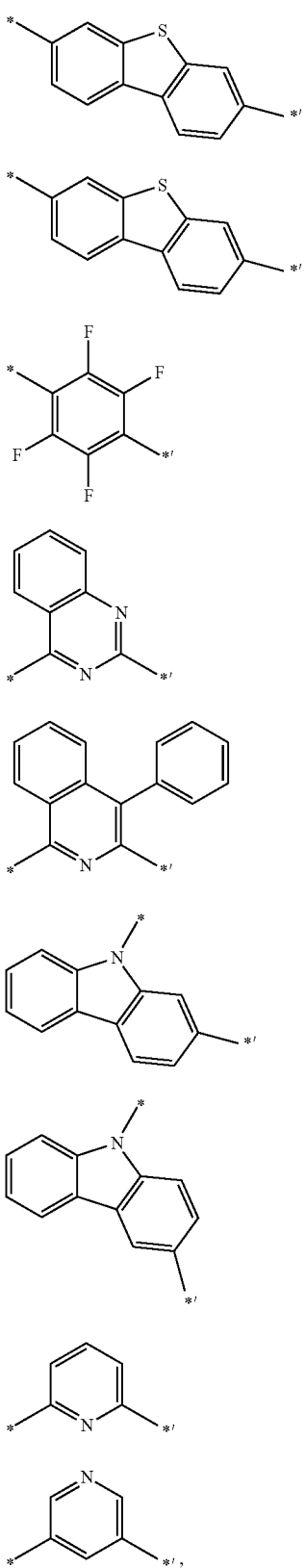

4-15
4-16
4-17
4-18
4-19
4-20
4-21
4-22
4-23 wherein * and *' represent binding sites of $L_{11}$ in the compound of Formula 1-1.

14. The chrysene-based compound as claimed in claim 13, wherein $R_{12}$ is selected from a hydrogen, a deuterium, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and groups represented by Formulae 5-1 to 5-38, in which * represents a binding site to the chrysene moiety in Formula 1-1:

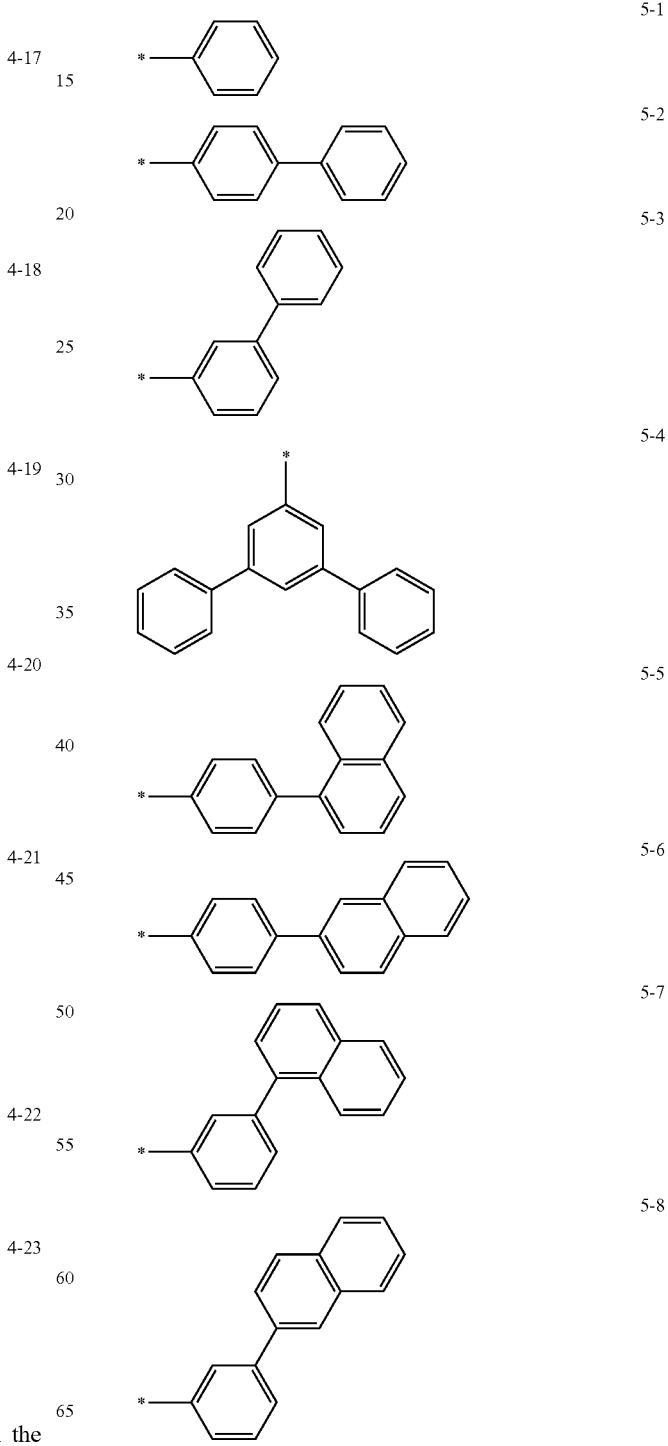

5-1
5-2
5-3
5-4
5-5
5-6
5-7
5-8

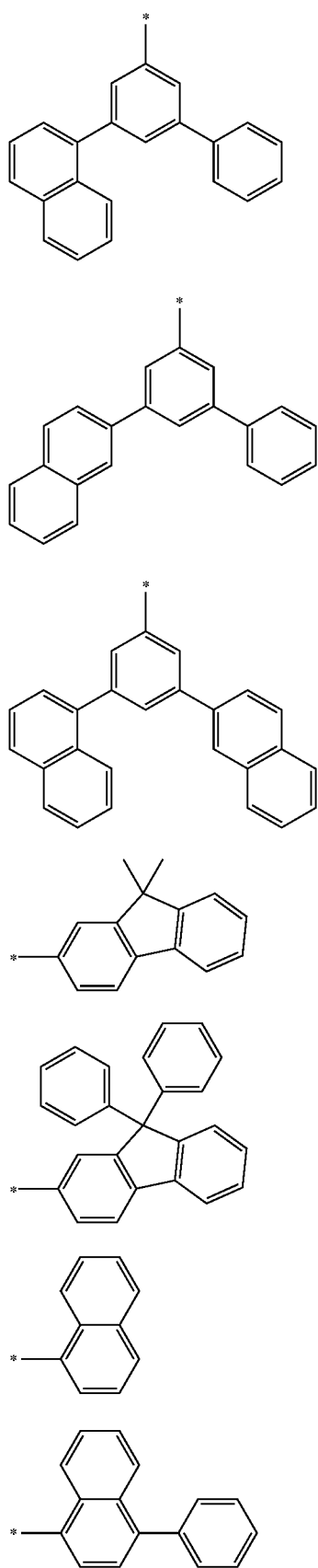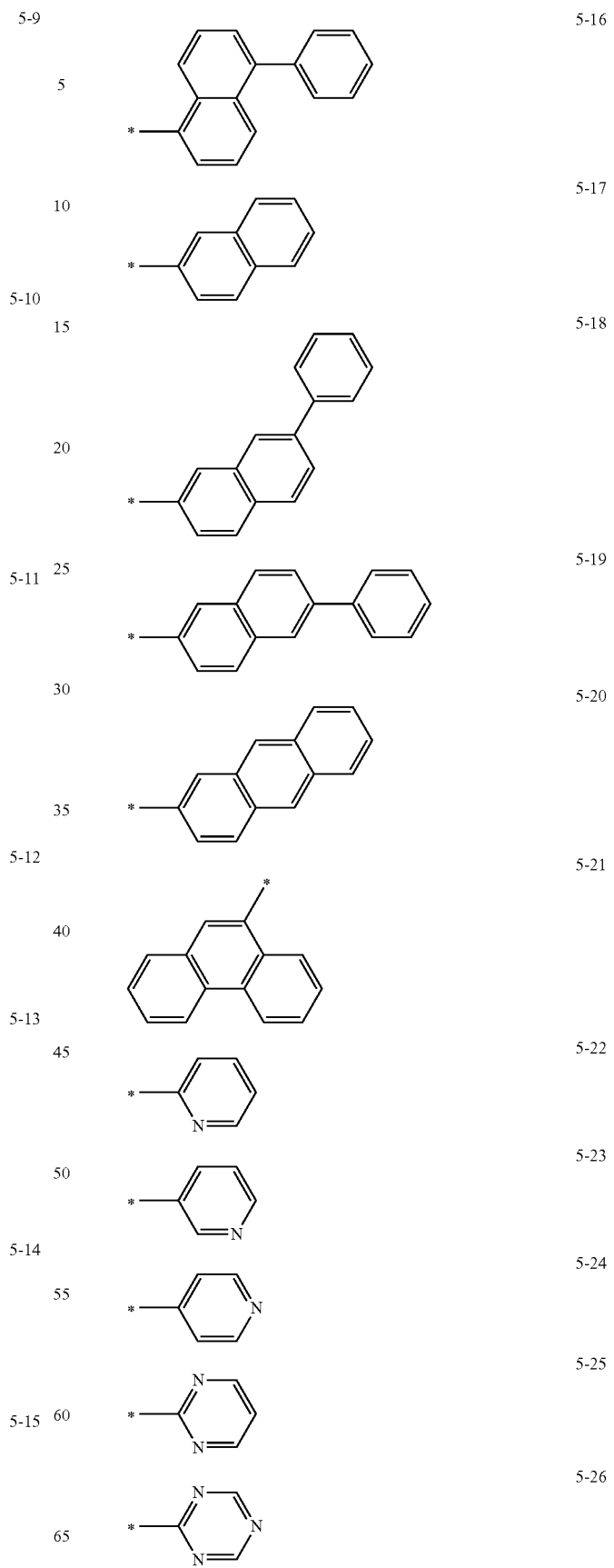

5-27 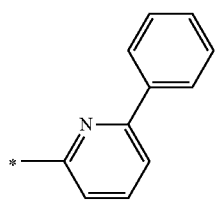

5-28 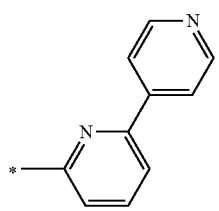

5-29 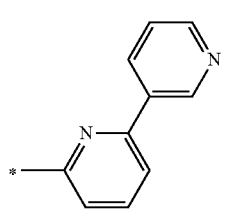

5-30 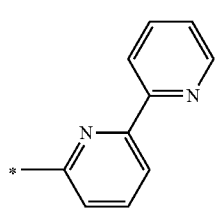

5-31 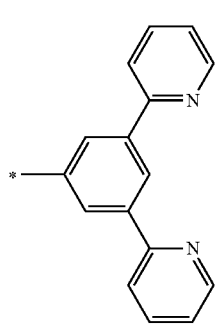

5-32 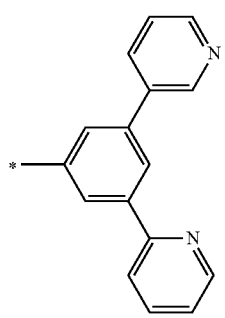

5-33 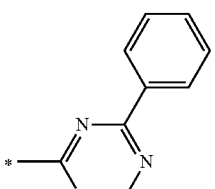

5-34 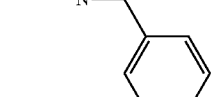

5-35 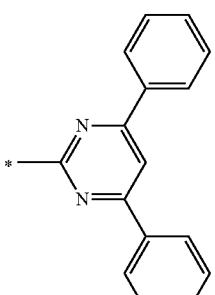

5-36 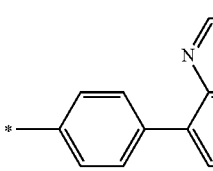

5-37 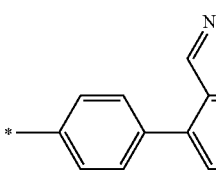

5-38 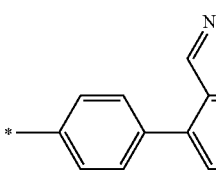

15. The chrysene-based compound as claimed in claim 12, wherein $R_{21}$ is selected from:

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group.

16. The chrysene-based compound as claimed in claim 1, wherein the chrysene-based compound represented by Formula 1 is one of Compounds 1 to 74:

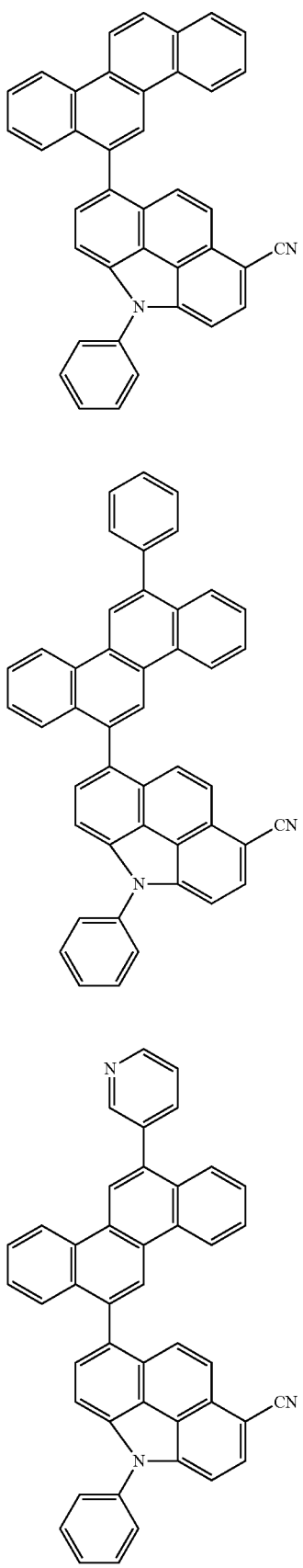
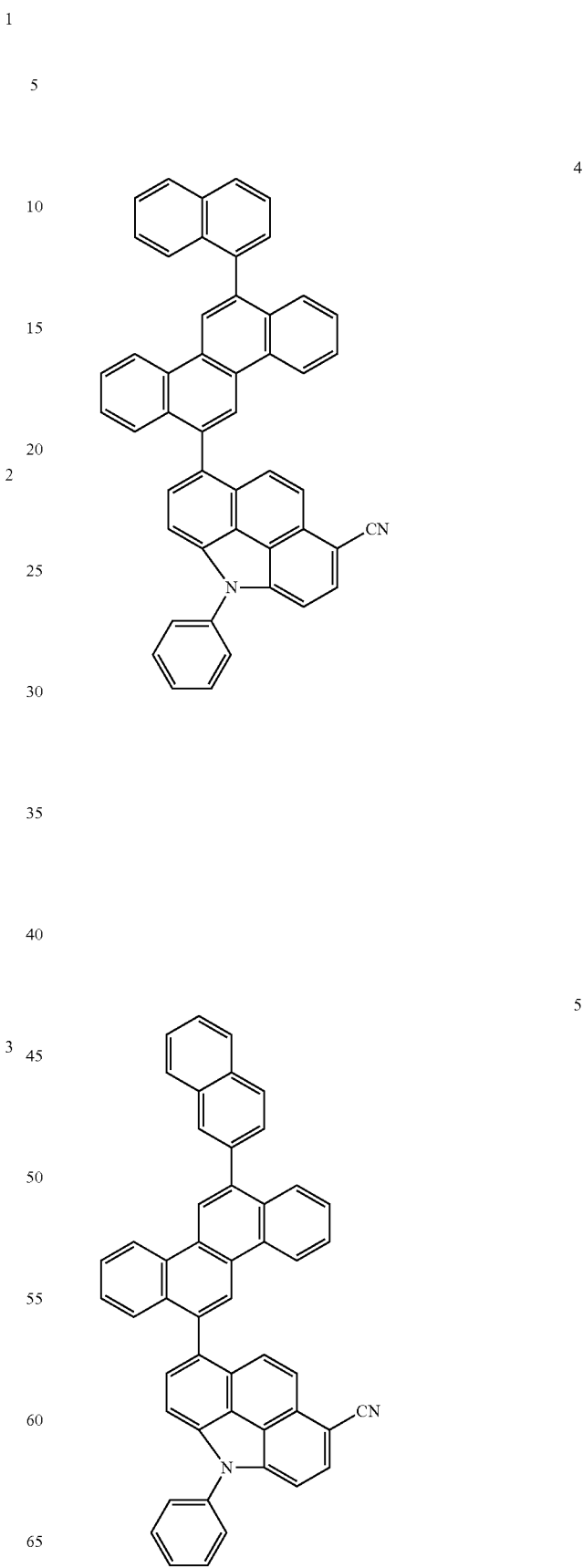

175
-continued
176
-continued
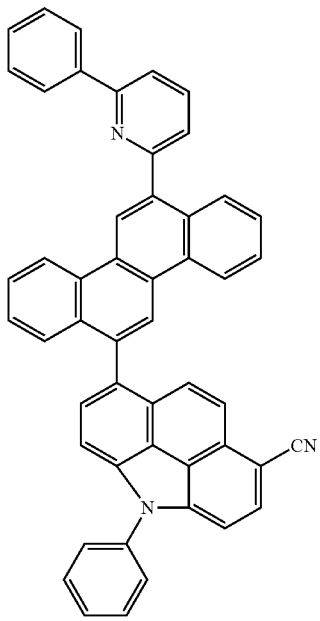
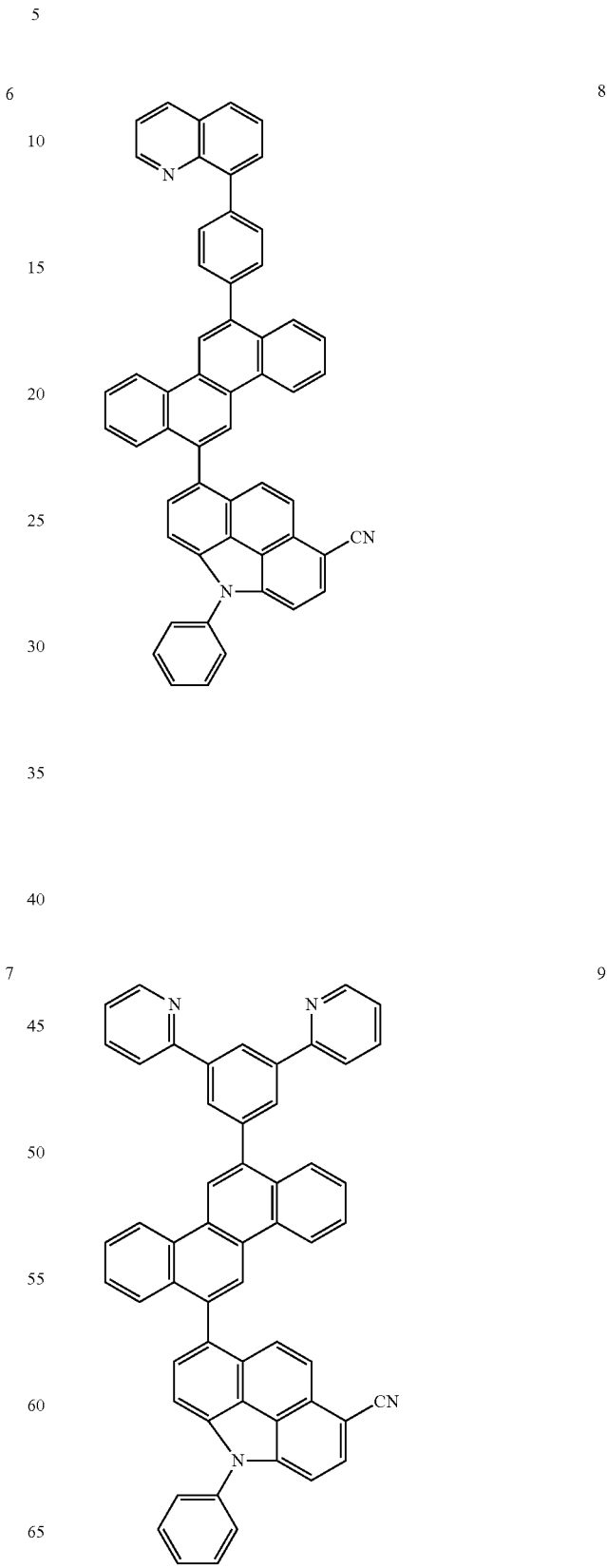

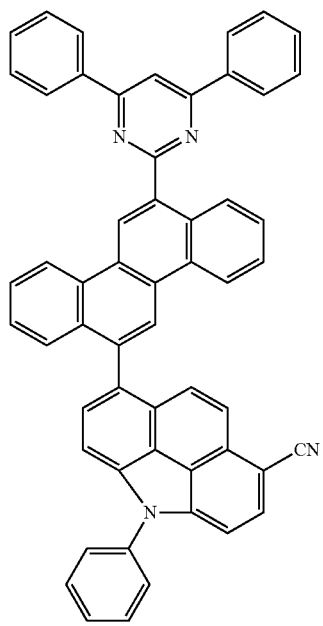
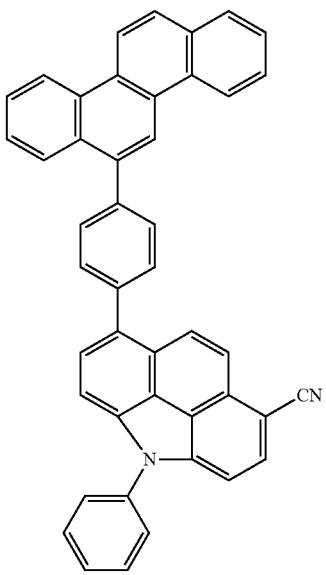
10
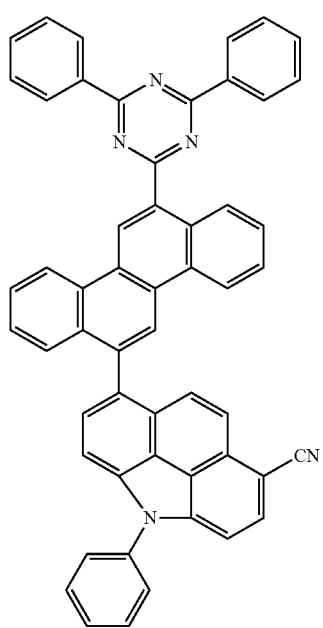
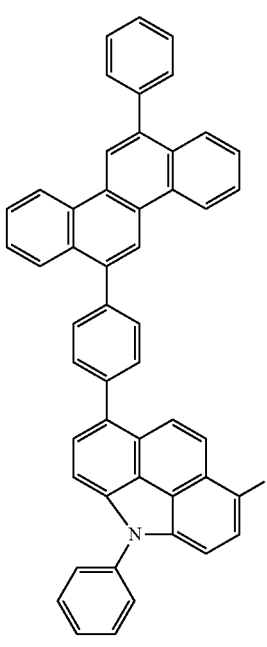

179
-continued
180
-continued
14
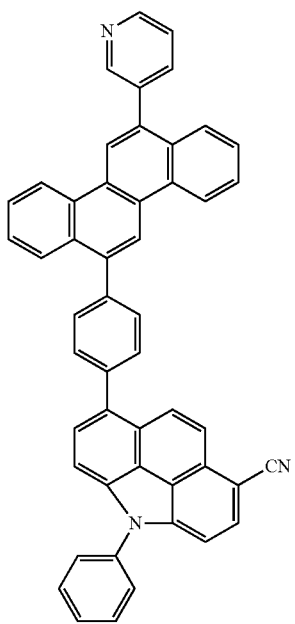
16
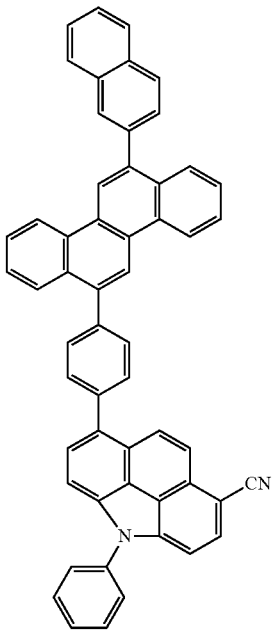
15
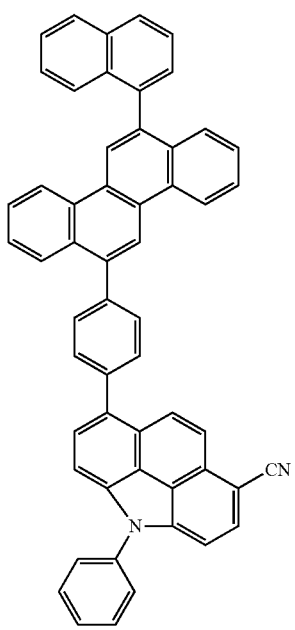
17
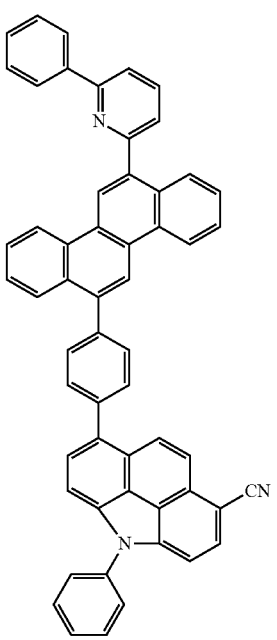

181
-continued
182
-continued
18
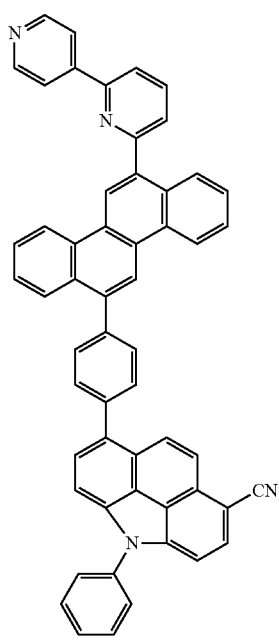
20
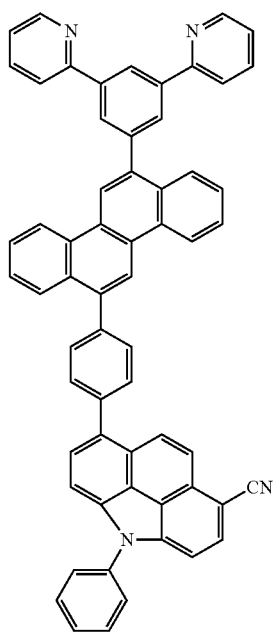
19
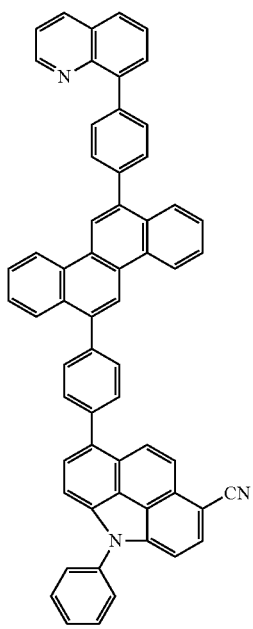
21
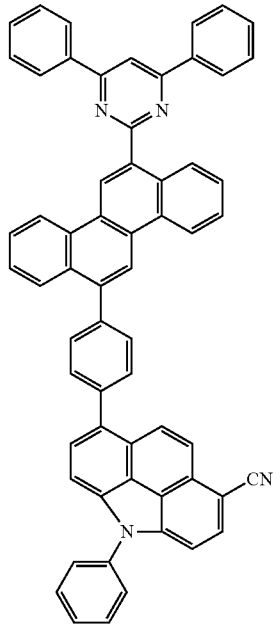

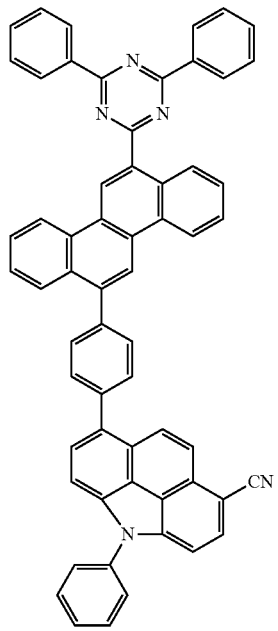
22
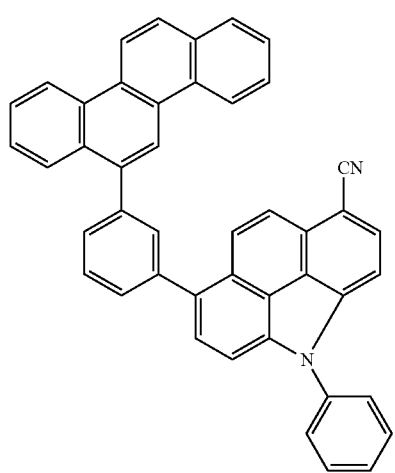
23
24
25

26
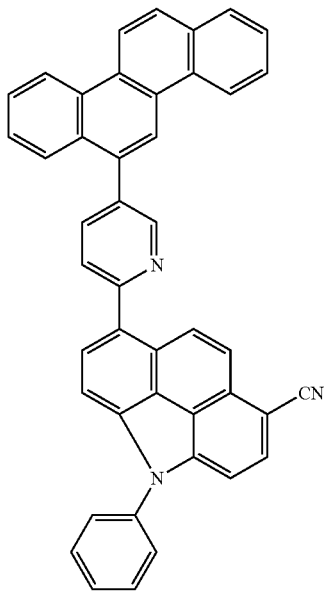
28
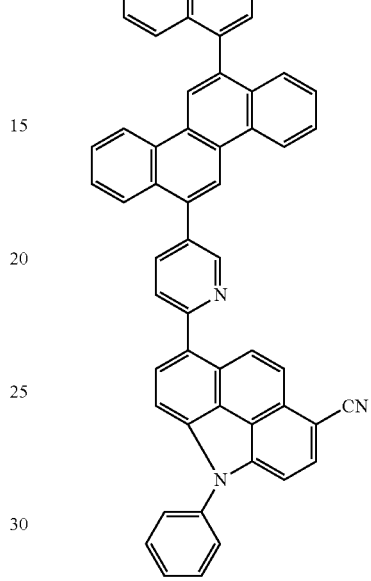
27
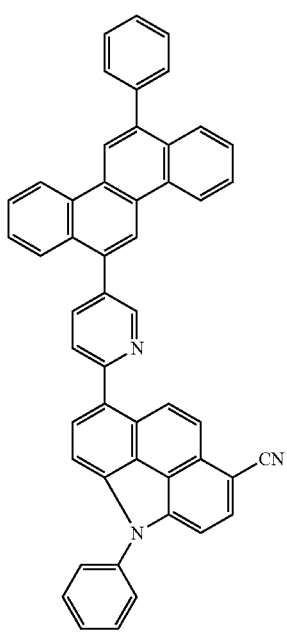
29
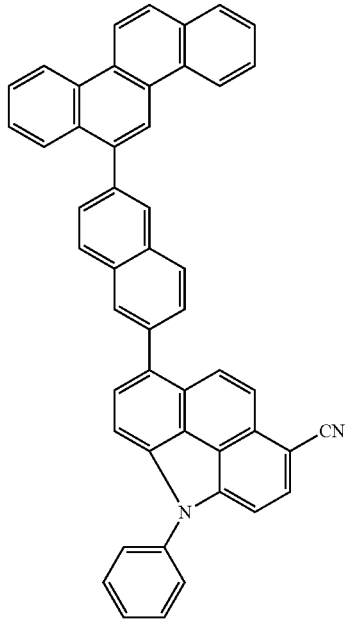

187
-continued
188
-continued
30
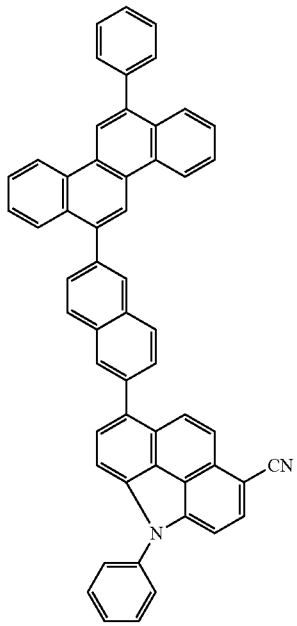
32
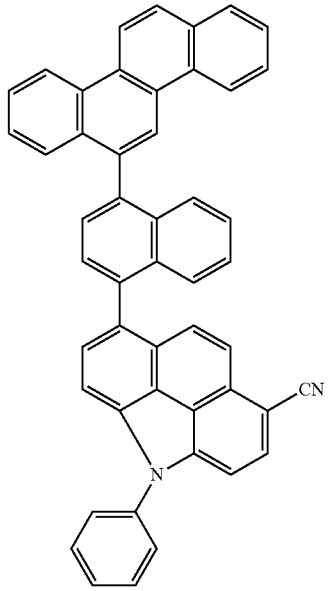
31
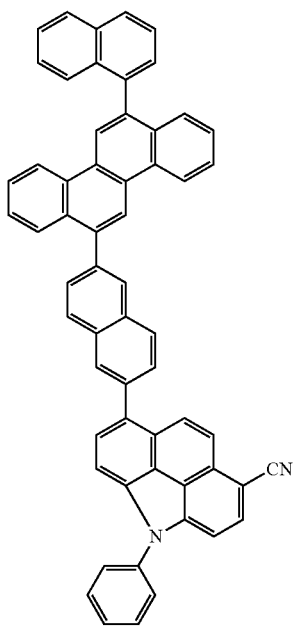
33
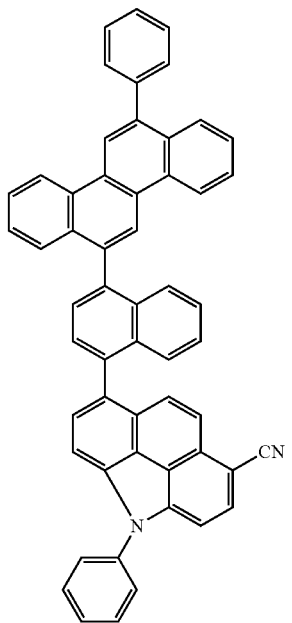

189
-continued
190
-continued
34
36
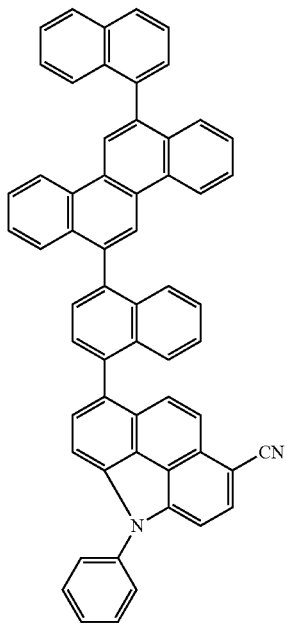
37

38
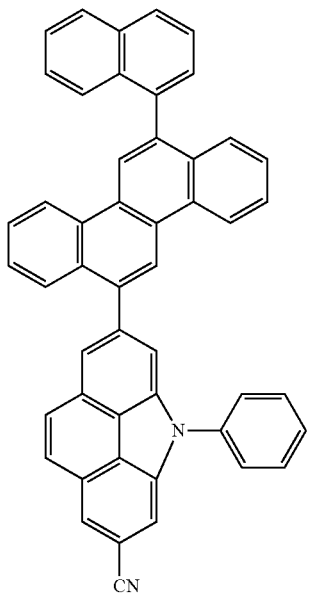
39
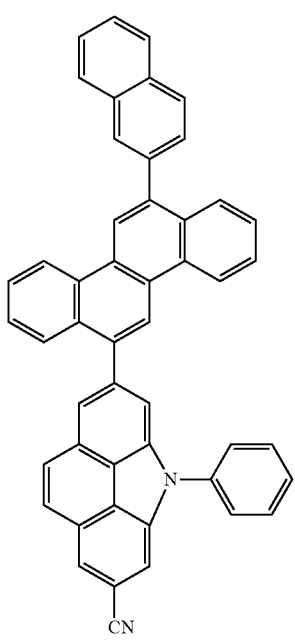
40
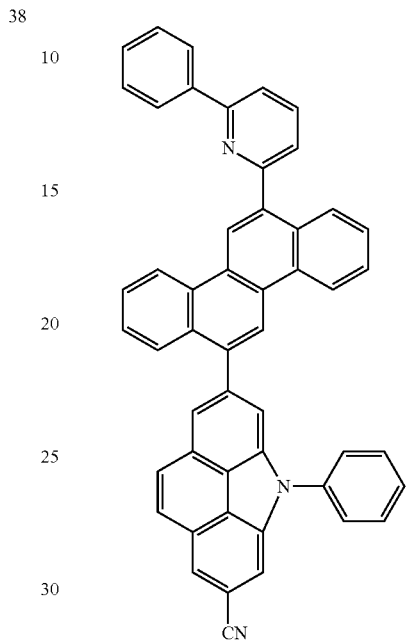
41
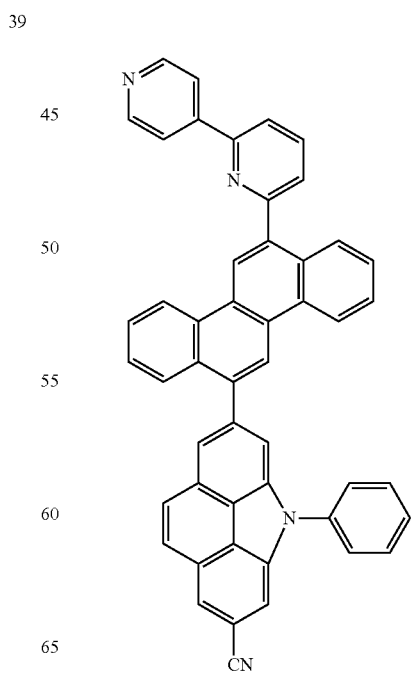

193
-continued
42 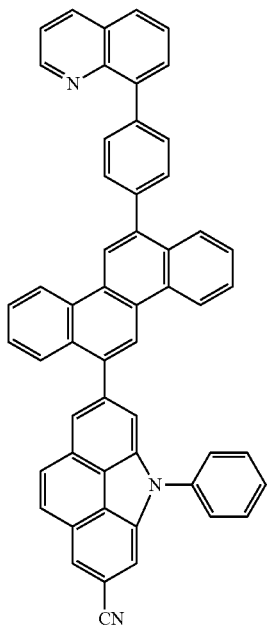
43 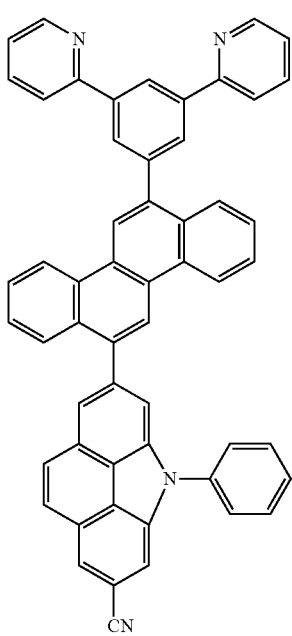
194
-continued
44 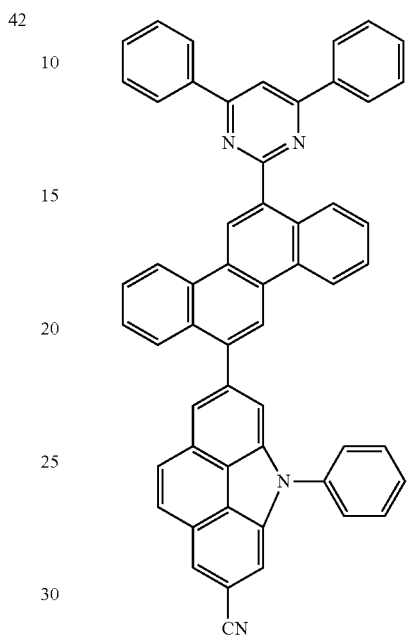
45 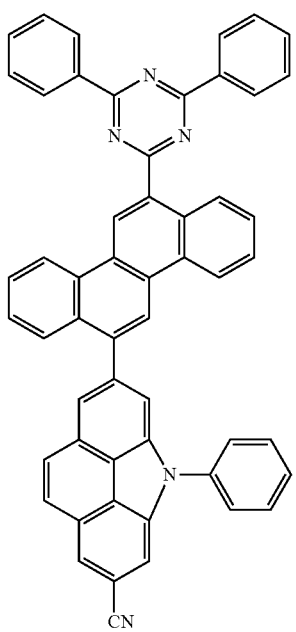

-continued
46
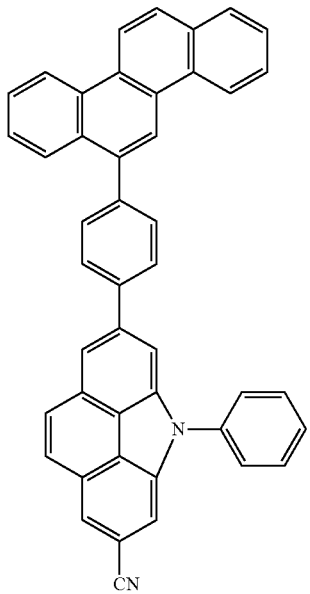
48
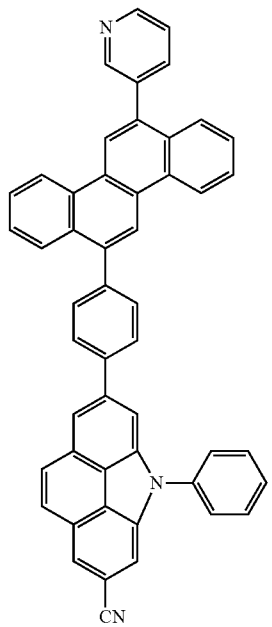
47
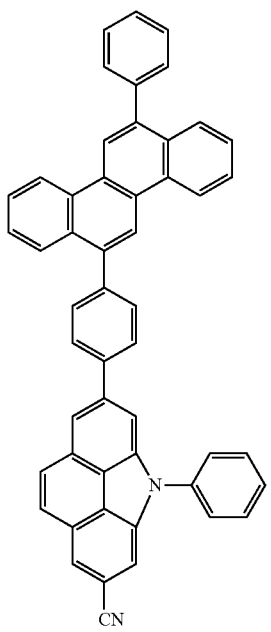
49
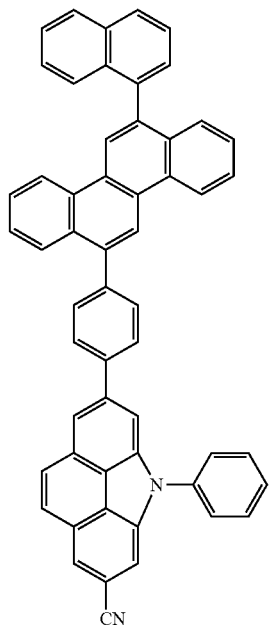

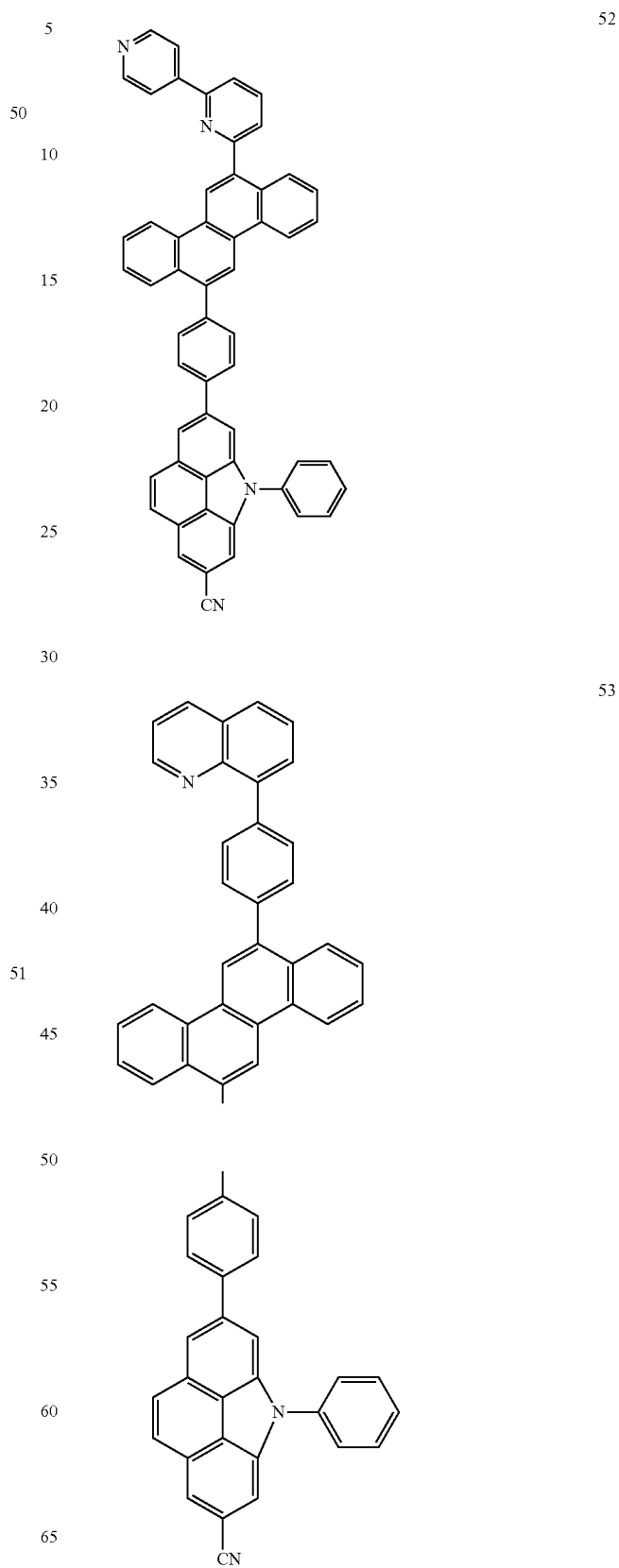

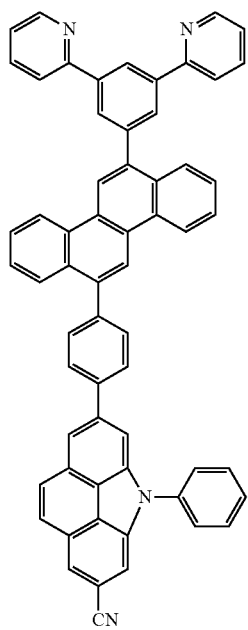
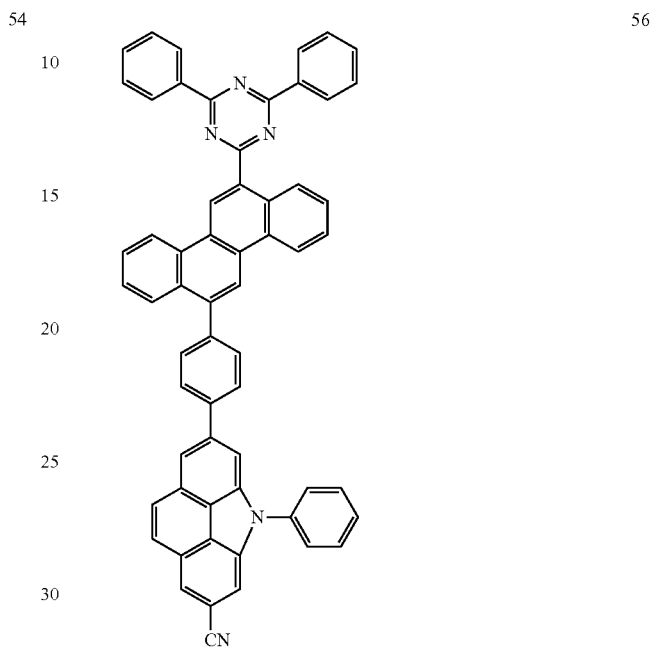
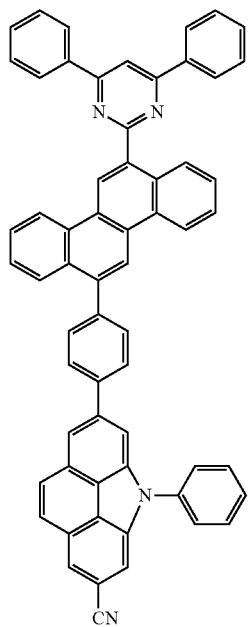
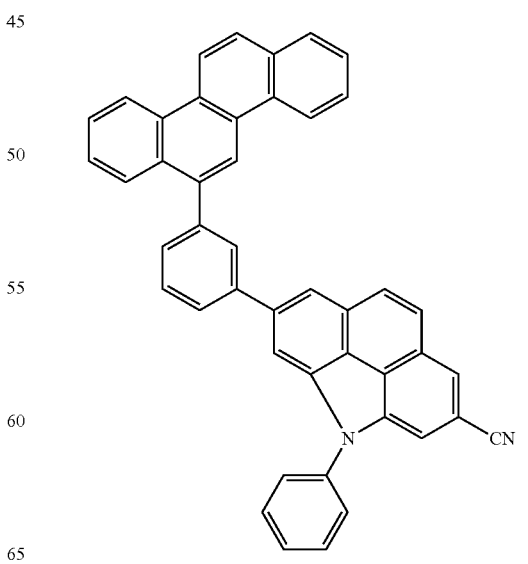

201
-continued
202
-continued
58
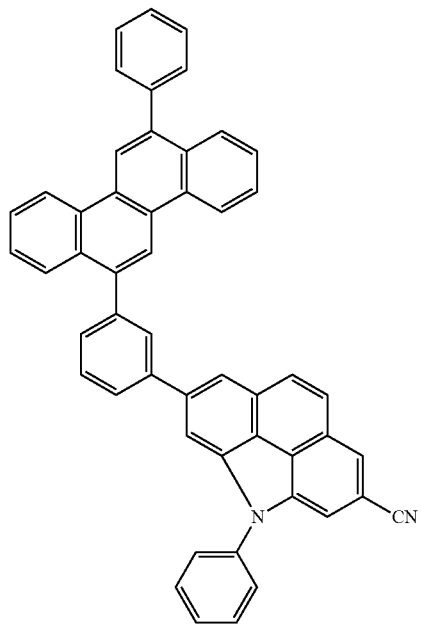
60
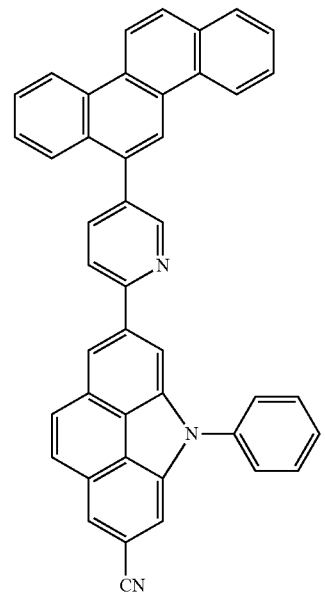
59
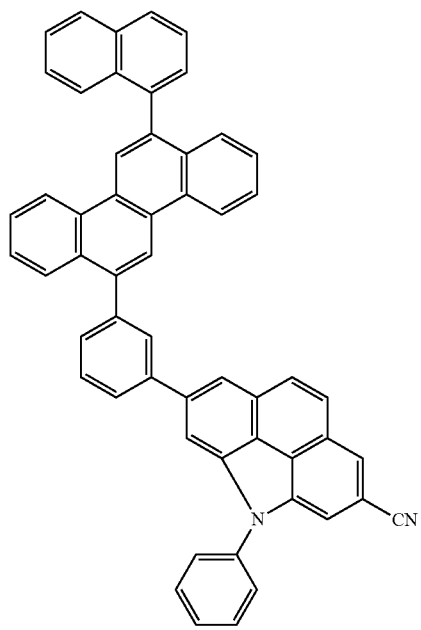
61
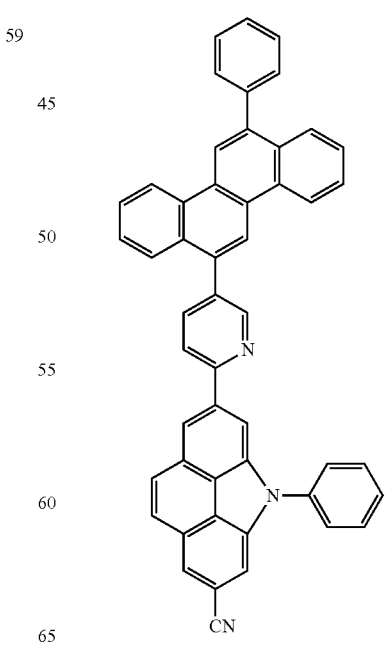

203
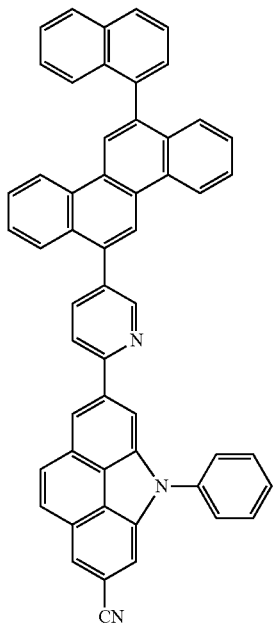
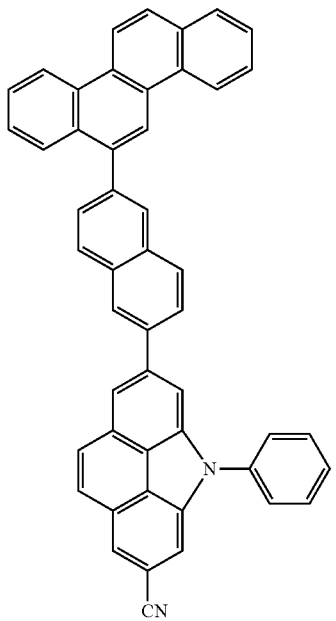
204
62
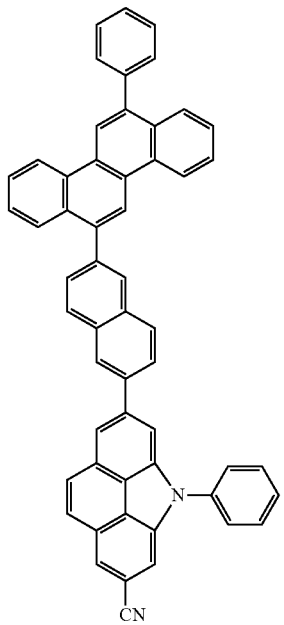
63
64
65
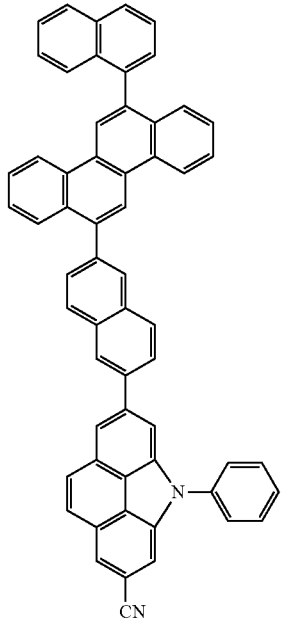

205
-continued
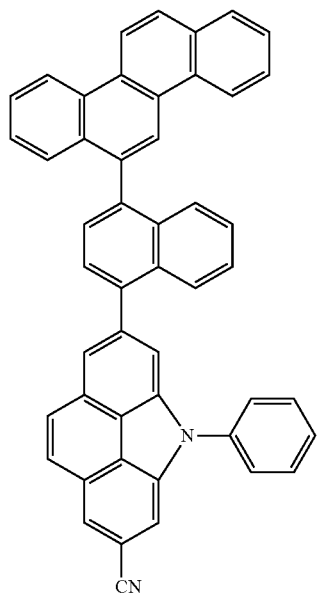
66
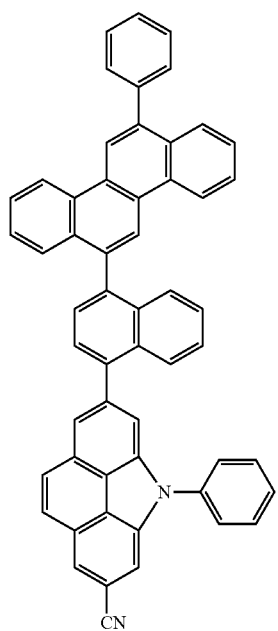
206
-continued
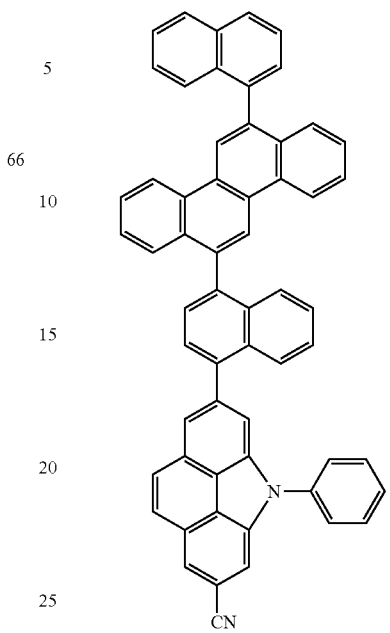
5
67
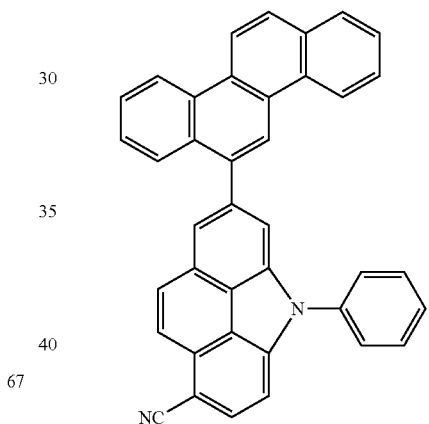
68
69
70
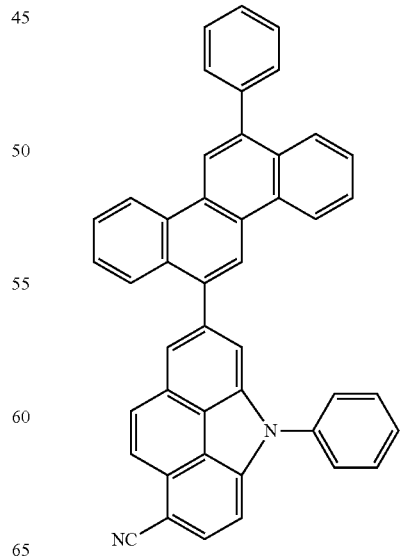

207
-continued

208
-continued

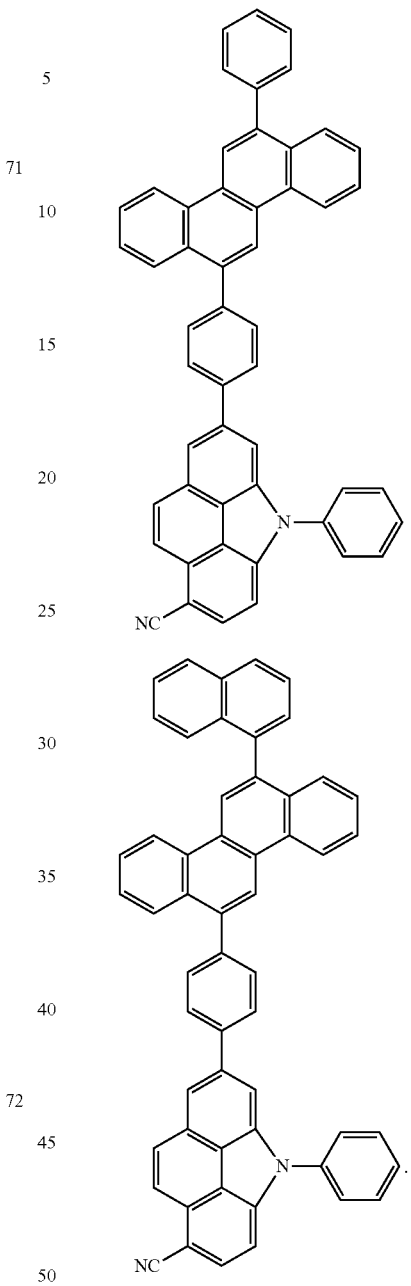

17. An organic light-emitting device, comprising:
   a first electrode;
   a second electrode opposite to the first electrode; and
   an organic layer between the first electrode and the second electrode, the organic layer including an emission layer, wherein the organic layer includes the chrysene-based compound as claimed in claim 1.

18. The organic light-emitting device as claimed in claim 17, wherein:
   the organic layer includes an electron transport region between the emission layer and the second electrode, and
   the electron transport region includes the chrysene-based compound.

19. The organic light-emitting device as claimed in claim 18, wherein:

the electron transport region includes an electron transport layer, and the electron transport layer includes the chrysene-based compound.

20. The organic light-emitting device as claimed in claim 17, wherein the organic layer includes a hole transport region between the first electrode and the emission layer.

* * * * *